(12) United States Patent
Boyer et al.

(10) Patent No.: US 11,904,049 B2
(45) Date of Patent: *Feb. 20, 2024

(54) PHARMACEUTICAL FORMULATION

(71) Applicant: Klaria Pharma Holding AB, Uppsala (SE)

(72) Inventors: Scott Boyer, Uppsala (SE); Fredrik Hübinette, Uppsala (SE); Leif Ingemarsson, Uppsala (SE); Susan Suchdev, Uppsala (SE)

(73) Assignee: Klaria Pharma Holding AB, Uppsala (SE)

( * ) Notice: Subject to any disclaimer, the term of this patent is extended or adjusted under 35 U.S.C. 154(b) by 110 days.

This patent is subject to a terminal disclaimer.

(21) Appl. No.: 17/457,460

(22) Filed: Dec. 3, 2021

(65) Prior Publication Data

US 2022/0160618 A1    May 26, 2022

Related U.S. Application Data

(63) Continuation of application No. 16/607,892, filed as application No. PCT/EP2018/065223 on Jun. 8, 2018, now Pat. No. 11,219,600.

(30) Foreign Application Priority Data

Jun. 8, 2017 (GB) .................................... 1709141

(51) Int. Cl.
    *A61K 9/00* (2006.01)
    *A61K 9/70* (2006.01)
    *A61K 31/439* (2006.01)
    *A61K 45/06* (2006.01)

(52) U.S. Cl.
    CPC ............ *A61K 9/006* (2013.01); *A61K 9/7007* (2013.01); *A61K 31/439* (2013.01); *A61K 45/06* (2013.01)

(58) Field of Classification Search
    CPC .... A61K 9/006; A61K 9/7007; A61K 31/439; A61K 45/06
    See application file for complete search history.

(56) References Cited

U.S. PATENT DOCUMENTS

| | | |
|---|---|---|
| 5,288,497 A | 2/1994 | Stanley et al. |
| 5,288,498 A | 2/1994 | Stanley et al. |
| 5,785,989 A | 7/1998 | Stanley et al. |
| 8,759,282 B2 | 6/2014 | Stenberg et al. |
| 9,192,570 B2 | 11/2015 | Wyse et al. |
| 9,833,461 B2 | 12/2017 | Modi |
| 10,039,710 B2 | 8/2018 | Potta et al. |
| 11,007,144 B2 | 5/2021 | Boyer et al. |
| 11,219,600 B2 | 1/2022 | Boyer et al. |
| 2004/0247649 A1 | 12/2004 | Pearce et al. |
| 2005/0031675 A1 | 2/2005 | Spence Leung et al. |
| 2006/0039959 A1 | 2/2006 | Wessling |
| 2006/0110331 A1 | 5/2006 | Dang et al. |
| 2008/0269347 A1 | 10/2008 | Bruss et al. |
| 2009/0186107 A1 | 7/2009 | Haber et al. |
| 2009/0221489 A1* | 9/2009 | Stenberg ................ A61P 25/34 514/4.8 |
| 2009/0246273 A1 | 10/2009 | Al-Ghananeem |
| 2010/0112050 A1 | 5/2010 | Ryoo et al. |
| 2011/0033542 A1 | 2/2011 | Myers et al. |
| 2014/0005218 A1* | 1/2014 | Myers ..................... A61K 47/10 514/282 |
| 2014/0178473 A1 | 6/2014 | Lim et al. |
| 2014/0256823 A1 | 9/2014 | McCarty |
| 2014/0271788 A1 | 9/2014 | Myers et al. |
| 2015/0005356 A1 | 1/2015 | Fleming |
| 2015/0224070 A1 | 8/2015 | Boudy et al. |
| 2015/0297653 A1 | 10/2015 | Speier |
| 2016/0051510 A1 | 2/2016 | Allen et al. |
| 2016/0206627 A1 | 7/2016 | Gosselin et al. |
| 2017/0079907 A1 | 3/2017 | Potta et al. |
| 2017/0165315 A1* | 6/2017 | Karavas ................. A61K 47/36 |
| 2017/0290776 A1 | 10/2017 | Schobel et al. |
| 2017/0290870 A1 | 10/2017 | Schaneville |
| 2017/0348251 A1 | 12/2017 | Schobel et al. |
| 2018/0104195 A1 | 4/2018 | Schobel et al. |

(Continued)

FOREIGN PATENT DOCUMENTS

| | | |
|---|---|---|
| CA | 2487882 A1 | 12/2003 |
| CN | 101081218 | 12/2007 |

(Continued)

OTHER PUBLICATIONS

Harding, S.E., et al., "Molecular Weidht Determination of Polysaccharides", Advances in Carbohydrate Analysis, 1991, vol. 1, pp. 69-73.

Martinsen, A., et al., "Comparision of Different Methods for Determination of Molecular Weight and Molecular Weight Distribution of Alginates", Carbohydrate Polymers 15 (1991) 171-193.

Non-Final Office Action for U.S. Appl. No. 17/054,941 "Pharmaceutical Formulation" dated Dec. 13, 2021.

Non-Final Office Action for U.S. Appl. No. 17/054,945 "Pharmaceutical Formulation" dated Dec. 13, 2021.

Third Party Observation for EP Application No. 3793517 "Pharmaceutical Formulation" dated Aug. 23, 2021.

"More Solutions to Sticky Problems", Brookfield AMETEK, accessed at https: / /www.brookfieldengineeri ng. com/ - / media/ ametekbrookfield / tech%20sheets/ more%20solutions%202017. pdf? la=en, 2017, 31 pages.

(Continued)

*Primary Examiner* — Snigdha Maewall

(74) *Attorney, Agent, or Firm* — Hamilton, Brook, Smith & Reynolds, P.C.

(57) ABSTRACT

The present invention relates to a film comprising an alginate salt of a monovalent cation or a mixture of alginate salts containing at least one alginate salt of a monovalent cation, and an antagonist of an opioid receptor, an inverse agonist of an opioid receptor, or a prodrug thereof. The present invention further relates to methods for manufacturing such a film, and the use of such a film in the treatment of a human patient, in particular the use of such a film in the treatment of the effects of acute opioid overdose, or the use of such a film in reducing the risk of opioid abuse.

20 Claims, 16 Drawing Sheets

(56) References Cited

U.S. PATENT DOCUMENTS

| | | |
|---|---|---|
| 2018/0117019 A1 | 5/2018 | Wang et al. |
| 2018/0125977 A1 | 5/2018 | Schobel et al. |
| 2020/0054550 A1 | 2/2020 | Boyer et al. |
| 2020/0246253 A1 | 8/2020 | Boyer et al. |
| 2021/0283047 A1 | 9/2021 | Boyer et al. |
| 2021/0346277 A1 | 11/2021 | Boyer et al. |
| 2021/0369601 A1 | 12/2021 | Boyer et al. |
| 2022/0273584 A1 | 9/2022 | Boyer et al. |
| 2022/0280453 A1 | 9/2022 | Boyer et al. |
| 2023/0018732 A1 | 1/2023 | Boyer et al. |

FOREIGN PATENT DOCUMENTS

| | | |
|---|---|---|
| CN | 101574330 | 11/2009 |
| CN | 102871984 | 1/2013 |
| CN | 102961365 | 3/2013 |
| CN | 105878171 A | 8/2016 |
| CN | 107080745 A | 8/2017 |
| EP | 1897543 A1 | 3/2008 |
| EP | 2431028 A2 | 3/2012 |
| EP | 1976562 B1 | 2/2018 |
| GB | 933462 | 8/1963 |
| IN | 351KOL2006 | 4/2006 |
| KR | 20080023873 | 3/2008 |
| KR | 20140110778 | 9/2014 |
| WO | WO 91/03236 | 3/1991 |
| WO | WO 98/01134 | 1/1998 |
| WO | WO 98/02182 | 1/1998 |
| WO | WO 01/87276 | 11/2001 |
| WO | WO 2003/101357 A1 | 5/2003 |
| WO | WO 2004/012720 A1 | 2/2004 |
| WO | WO 2004/045305 | 6/2004 |
| WO | WO 2004/075877 | 9/2004 |
| WO | WO 2005/004989 | 1/2005 |
| WO | WO 2005/018323 A1 | 3/2005 |
| WO | WO 2005/048980 A1 | 6/2005 |
| WO | WO 2006/023976 | 3/2006 |
| WO | WO 2006/095267 | 9/2006 |
| WO | WO 2006/096913 A1 | 9/2006 |
| WO | WO 2007/028247 | 3/2007 |
| WO | WO 2007/049102 | 5/2007 |
| WO | WO 2007/073346 A1 | 6/2007 |
| WO | WO 2007/125533 A2 | 11/2007 |
| WO | WO 2007/143674 | 12/2007 |
| WO | WO 2008/034881 | 3/2008 |
| WO | WO 2008/073918 A1 | 6/2008 |
| WO | WO 2008/095144 | 8/2008 |
| WO | WO 2008/098195 A2 | 8/2008 |
| WO | WO 2009/126132 | 10/2009 |
| WO | WO 2010/029374 | 3/2010 |
| WO | WO 2011036521 A2 | 3/2011 |
| WO | WO 2011/053251 | 5/2011 |
| WO | WO 2012/117257 | 9/2012 |
| WO | WO 2012/121461 A1 | 9/2012 |
| WO | WO 2013/015545 A1 | 1/2013 |
| WO | WO 2013/019187 A1 | 2/2013 |
| WO | WO 2013/052770 | 4/2013 |
| WO | WO 2013/059629 | 4/2013 |
| WO | WO 2013/171146 A1 | 11/2013 |
| WO | 2014/144241 A1 | 9/2014 |
| WO | WO 2014/160404 | 10/2014 |
| WO | WO 2014/202088 A1 | 12/2014 |
| WO | WO 2015/025324 | 2/2015 |
| WO | WO 2015/074663 A1 | 5/2015 |
| WO | WO 2015/160941 | 10/2015 |
| WO | WO 2015/195708 | 12/2015 |
| WO | WO 2016/024008 A1 | 2/2016 |
| WO | WO 2016/201286 | 12/2016 |
| WO | WO 2017003935 A1 | 1/2017 |
| WO | WO 2017/020125 | 2/2017 |
| WO | WO 2017/120492 | 7/2017 |
| WO | WO 2017/132410 | 8/2017 |
| WO | WO 2017/135195 A1 | 8/2017 |
| WO | WO 2017/180707 A1 | 10/2017 |
| WO | WO 2018/091473 A1 | 11/2017 |
| WO | WO 2018/224674 A1 | 12/2018 |
| WO | WO 2019219773 A1 | 11/2019 |
| WO | WO 2019224323 A1 | 11/2019 |
| WO | WO 2021028578 | 2/2021 |
| WO | WO 2021/037960 | 3/2021 |
| WO | 2021090309 A1 | 5/2021 |
| WO | WO 2017/218918 | 12/2021 |

OTHER PUBLICATIONS

Abdelkader et al., "Novel in situ gelling ocular films for the opioid growth factor-receptor antagonist-naltrexone hydrochloride: Fabrication, mechanical properties, mucoadhesion, tolerability and stability studies", *Int J Pharmaceutics*, 2014, 477(1-2), 631-642.

Abd El Azim, H., et al., "Liposomal buccal mucuadhesive film for improved delivery and permeation of water-soluble vitamins", International Journal of Pharmaceutics, 2015, 488(1):78-85.

Alzheimer's Association: 10 Early Signs and Symptoms of Alzheimer's, 2018, accessed at https://www.alz.org/10-signs-symptoms-alzheimers-dementia.asp.

Asthana et al., "Formulation and Evaluation of Alginate-Based Mucoadhesive Buccal Patch for Delivery of Antimigraine Drug", *Asian J Pharm Clin Res*, 2018, 11(4), 185-191.

Bachelor et al. "Organotypic human oral tissue models for evaluation of oral care products", presented at Society of Toxicology 2014 annual meeting, 2014, 1, 3-7; only abstract available via https://www.mattek.com/referencelibrary/organotypic-human-oral-tissue-models-for-evaluation-of-oral-careproducts/.

Bachynsky et al., "Factors Affecting the Efficiency of a Self-Emulsifying Oral Delivery System", *Drug Dev Ind Pharm*, 1997, 23, 809-816.

Basu et al., "Cannabinoid Receiptor 2 is Critical for the Homing and Retention of Marginal Zone B Lineage Cells and for Efficient T-Independent Immune Responses", *J Immunol*, 2011, 187(11), 5720-5732.

Begg et al., "Evidence for novel cannabinoid receptors", *Pharmacology Et Therapuetics*, 2005, 106(2), 133-145.

Ben Amar, M., "Cannabinoids in medicine: A review of their therapeutic potential", *J Ethnopharmacol*, 2006, 105(1-2), 1-25.

Bhagwati et al., "Bioavailability Enhancement of Rizatriptan Benzoate by Oral Disintegrating Strip: In Vitro and In vivo Evaluation", *Current Drug Delivery*, 2016, 13(3), 462-470.

Bouhassira et al., "Prevalence of chronic pain with neuropathic characteristics in the general population", *Pain*, 2008, 136(3), 380-387.

Bourassa et al., "Label-Free Monitoring of µ-Opioid Receptor-Mediated Signaling", *Mot Pharmacol*, 2014, 86(2), 138-149.

Chey, "Irritable Bowel Syndrome A Clinical Review", *JAMA*, 2015, 313(9), 949-958.

Date et al., "Self-nanoemulsifying drug delivery systems" formulation insights, applications and advances, *Nanomedicine*, 2010, 5(10), 1595-1616.

Davis and Brewster, "Cyclodextrin-Based Pharmaceutics: Past, Present and Future", *Nat Rev Drug Discovery*, 2004, 3, 1023-1035.

Davis and Dickey, "Regulated Airway Goblet Cell Mucin Secretion", *Annu Rev Physiol*, 2008, 70, 487-512.

Dawson et al., "The In Vitro Cell Association of Invasin Coated Polylactide-Co-Glycolide Nanoparticles", *Pharm Res*, 2000, 17(11), 1420-1425.

Dechant et al., "Sumatriptan A Review of its Pharmacodynamic and Pharmacokinetic Properties, and Therapeutic Efficacy in the Acute Treatment of Migraine and Cluster Headache", *Drugs*, 1992, 43(5), 776-798.

Derry et al., "Sumatriptan (all routes of administration) for acute migraine attacks in adults—overview of Cochrane reviews (Review)", *Cochrane Database of Systematic Reviews*, 2014, 5, CD009108.

Dowling et al., "Population Phamacokinetics of Intravenous, Intramuscular, and Intranasal Naloxone in Human Volunteers", *Ther Drug Monit*, 2008, 30(4), 490-496.

Dusquesnoy et al.,"Comparative clinical pharmacokinetics of single doses of sumatriptan following subcutaneous, oral, rectal and intranasal administration", *Eur J Pharm Sci*, 1998, 6(2), 99-104.

(56) References Cited

OTHER PUBLICATIONS

ElSohly and Slade, "Chemical constituents of marijuana: The complex mixture of natural cannabinoids" *Life Sciences*, 2005, 78, 539-548.
European Pharmacopoeia, 2013, 2, 1490-1492.
Ferrari et al., "Interindividual variability of oral sumatriptan pharmacokinetics and of clinical response in migraine patients", *Eur J Clin Pharmacol*, 2008, 64, 489-495.
FMC Biopolymer, Product Specification Bulletin for Protanal® LFR 5/60, version 3, Oct. 12, 2013.
FMC Biopolymer, Product Specification for Manucol® LB, 2013.
Fowler et al., "The Clinical Pharmacology, Pharmacokinetics and Metabolism of Sumatriptan", *Eur Neural*, 1991, 31, 291-294.
Friedl et al.,"Development and Evaluation of a Novel Mucus Diffusion Test System Approved by Self-Nanoemulsifying Drug Delivery systems", *Pharmaceutics, drug delivery and pharmaceutical technology*, 2013, 102, 4406-4413.
Gizurason et al., "Anatomical and Histological Factors Affecting Intranasal Drug and Vaccine Delivery", *Current Drug Delivery*, 2012, 9, 566-582.
Grubstein and Milano, "Stabilization of epinephrine in a local anesthetic injectable solution using reduced levels of sodium metabisulfite and edta", *Drug Development and Industrial Pharmacy*, 1992, 18(14), 1549-1566.
Gupta et al.,"Design and Development of Oral Transmucosal Film for Delivery of Salbutamol Sulphate", *Journal of Pharmaceutical, Chemical and Biological Sciences*, 2014, 2(2), 118-129.
Haas and Harper, "Ketamine: A Review of Its Pharmacologic Properties and Use in Ambulatory Anesthesia", *Anesth Prag*, 1992, 39, 61-68.
He et al., "Adapting liposomes for oral drug delivery", *Acta Pharmaceutica Sinica B*, 2019, 36-48.
https://pubchem.ncbi.nlm.nih.gov/compound/naloxone, C19H21NO497 4 pages, downloaded on Aug. 13, 2019.
Hussain et al, "Utilizing Bacterial Mechanisms of Epithelial Cell Entry: Invasin-induced Oral Uptake of Latex Nanoparticles", *Pharm Res*, 1998, 15(1), 153-156.
Imigran 10mg Nasal Spray, Summary of Product Characteristics updated Feb. 26, 2015, https://www.medicines.org.uk/emc/product/2214/smpc.
Imigran Injection, Subject, Summary of Product Characteristics updated May 4, 2018, https://www.medicines.org.uk/emc/product/944/smpc.
Imigran Tablets, Injection and Nasal Spray. SmPC, 2007, 24.
Imigran Tablets 50 mg, Summary of Product Characteristics updated Oct. 6, 2020, https://www.medicines.org.uk/emc/product/945/smpc.
Imigran Tablets 50 mg, Summary of Product Characteristics updated Oct. 3, 2016, https://www.medicines.org.uk/emc/product/945/smpc.
International Preliminary Report on Patentability for International Application No. PCT/EP2018/065223, "Pharmaceutical Formulation", dated Dec. 10, 2019.
International Search Report for International Application No. PCT/EP2018/065223, "Pharmaceutical Formulation", dated Aug. 10, 2018.
Kaminski, "Inhibition of the cAMP signaling cascade via cannabinoid receptors: a putative mechanism of immune modulation by cannabinoid compounds", *Toxicology Lett*, 1998, 102-103, 59-63.
Klaria press releases dated Oct. 29, 2015, Feb. 24, 2016, Apr. 19, 2016, May 11, 2016, Jul. 1, 2016 and Aug. 15, 2016.
Lee and Mooney, "Alginate: properties and biomedical applications", *Prag Polym Sci*, 2012, 37(1 ), 106-126.
Lim, K., et al., "a Systematic Review of the Effectiveness of Medical Cannabis for Psychiatric, Movement and Neurodegenertive Disorders", Clinical Psychopharmacology and Neuroscience 2017; 15(4): 301-312.
Maas et al., "A model-based approach to treatment comparison in acute migraine", *Br J Clin Pharm*, 2007, 62(5), 591-600.
Managaro and Wertz, "The Effects of Permeabilizers on the In Vitro Penetration of Propranolol Through Porcine Buccal Epithelium", *Mil Med*, 1996, 161 (11 ), 669-672.
Manfredi, P.L., et al., "Sumatriptan for Headache Caused by Head and Neck Cancer", Headache 2000; 40:758-760.
Marasini et al., "Development and Optimization of Self-Nanoemulsifying Drug Delivery system with Enhanced Bioavailability by Box-Behnken Design and Desirability Function", *J Pharm Sci*, 2012, 101, 4584-4596.
Market Size and Demand for Marijuana in Colorado http://www.cannabisconsumer.org/uploads/9/7 /9/6/97962014/market size and demand studyJuly 9 2014%5B1%5D.pdf.
Marttin et al., "The effect of methylated β-cyclodextrins on the tight junctions of the rat nasal respiratory epithelium: Electron Microscopic and confocal laser scanning microscopic visualization studies", *J Control Release*, 1999, 57, 205-213.
McLean-Tooke et al., "Adrenaline in the treatment of anaphylaxis: what is the evidence?" *BMJ*, 2003, 327(7427), 1332-1335.
Mechoulam et al., "Cannabidiol—Recent Advances" *Chemistry Et Biodiversity*, 2007, 4, 1678-1692.
Merkus et al., "Cyclodestrins in nasal drug delivery", *Adv Drug Del Rev*, 1999, 36, 41-57.
Muller et al., "Ketamine enantiomers in the rapid and sustained antidepressant effects", *Ther Adv Psychopharmacol*, 2016, 6, 185-192.
Nadel, "Acute effects of inhalation of cigarette smoke on airway conductance", *J Appl Physiol*, 1961, 16, 713-716.
Nicholson, Ulcerative Colitis Statistics, 2016, accessed at InflammatoryBowelDisease.net, Sep. 30, 2019, 2 pages.
NIDDK, Definition and Facts for Crohn's Disease, 2017, accessed at https: / /www. niddk. nih. gov/ health-information/ digestive-diseases/ crohnsdisease/ definition-facts.
Oesterling, "The adverse effect of ascorbic acid on the stability of adrenaline and noadrenaline solutions", *Biochim Biophys Acta*, 1957, 24(1), 178-187.
Owen et al., "The Preclinical toxicological evaluation of sumatriptan", *Human Et Experimental Toxicology*, 1995, 14, 959-973.
Ozaki et al., "Inhibition of Crystal Nucleation and Growth by Water-Soluble Polymers and its Impact on the Supersaturation Profiles of Amorphous Drugs", *J Pharm Sci*, 2013, 102, 2273-2281.
Parish et al.,"A systematic review of epinephrine degradation with exposure to excessive heat or cold", *Annals of Allergy, Asthma Et Immunology*, 2016, 117(1), 79-87.
Paudel et al., "Cannabidiol bioavailability after nasal and transdermal application: effect of permeation enhancers", *Drug Dev Ind Pharm*, 2010, 36, 1088-1097.
Pertwee, "The pharmacology of cannabinoid receptors and their ligands: an overview", *IntJObesity*, 2006, 30, S13-S18.
Pouton, "Formulation of poorly water-soluble drugs for oral administration: Physicochemical and physiological issues and the lipid formulation classification system", *European Journal of Pharmaceutical Sciences*, 2006, 29(3-4), 278-287.
Prachayasittikul et al., "EDTA-induced Membrane Fluidization and Destabilization: Biophysical Studies on Artificial Lipid Membranes", *Acta biochimica et biophysica Sinica*, 2007, 39(11 ), 901-913.
Pradhan et al., "Fabrication of a uniformly sized fenofibrate microemulsion by membrane emulsification", *J Microencapsul*, 2013, 30, 42-48.
Sayed et al., "Fast-Dissolving Sublingual Films of Terbutaline Sulfate: Formulation and In Vitro/In Vivo Evaluation", *Mot Pharmaceutics*, 2013, 10(8), 2942-2947.
Shannon, R.D. "Revised Effective Ionic Radii and Systematic Studies of Interatomic in Halides and Chalcogenides", Act Cryst. (1976) A 22, 751.
Sharma et al., "Development and Characterization of Self Emulsifying Drug Delivery system of a Poorly Water Soluble Drug Using Natural Oil", *Acta Pol Pharm*, 2012, 69, 713-717.
Shojaei, "Buccal Mucosa As a Route for Systemic Drug Delivery: A Review", *J Pharmaceut Sci*, 1998, 1 (1) 15-30.
Shtenberg et al, "Mucoadhesive alginate pastes with embedded liposomes for local oral drug delivery", *Int J Biol Macromol*, 2018, 111, 62-69.
Simons, "Epinephrine absorption in children with a history of anaphylaxis", *J Clin Immunol*, 1998, 101, 33-37.

(56) References Cited

OTHER PUBLICATIONS

Sinner and Graf, "Ketamine" in *Modern Anesthetics: Handbook of Experimental Pharmacoogy*. Eds. Schuttler and Schwilden, 182, 313-333 (2008).
Skulason et al., "Evaluation of polymeric films for buccal drug delivery", *Pharmazie*, 2009, 64(3), 197-201.
Sperger et al., "Analysis of Composition, Molecular Weight, and Water Content Variations in Sodium Alginate Using Solid-State NMR Spectroscopy", *J Pharmaceut Sci*, 2011, 100, 3441-3452.
Squier and Wertz. "Structure and function of the oral mucosa and implications for drug delivery" in *Oral mucosa[ drug delivery*. Ed. Rathbone; pub. Dekker, 1996, 1-25.
Stepensky et al., "Long-Term Stability Study of [-Adrenaline Injections: Kinetics of Sulfonatation and Racemization Pathways of Drug Degradation", *J Pharmaceut Sci*, 2004, 93(4), 969-980.
Stout and Cimino, "Analysis of Composition, Molecular Weight, and Water Content Variations in Sodium Alginate Using Solid-State NMR Spectroscopy", *Drug Met Rev*, 2014, 46(1), 86-95.
Tashkin, "Acute Effects of Smoked Marijuana and Oral $\Delta^\circ$-Tetrahydrocannabinol on Specific Airway Conductance in Asthmatic Subjects[1-3]", *Am Rev Respir Dis*, 1974, 109, 420-428.
Tayel et al., "Sumatriptan succinate sublingual fast dissolving thin films: formulation and in vitro/invivo evaluation", *Pharm Dev Technol*, 2016, 31, 328-337.
Thakur et al., "Transdermal and Buccal Delivery of Methylxanthines Through Human Tissue in Vitro", *Drug Dev. Ind. Pharm.*, 2007, 33(5), 513-521.
Tuleu et al., "Short term stability of pH-adjusted lidocaine-adrenaline epidural solution used for emergency caesarean section", *International Journal of Obstetric Anesthesia*, 2008, 17(2), 118-122.
Tylleskar et al., "Pharmacokinetics of a new, nasal formulation of naloxone", *Eur J Clin Pharmacol*, 2017, 73, 555-562.
www.drugs.com/imitrex.html, downloaded Aug. 13, 2019, 6 pages.
www.drugs.com/monograph/sumatriptan.html, downloaded Aug. 13, 2019, 28 pages.
www.drugs.com/naloxone.html. (downloaded on Aug. 13, 2019).
www.epipen.com/hcp/media/files/epipen/prescribing information. pdf Aug. 2012, 2 pages.
www.mannamolecular.com/2016/09/forms-of-cannabis-intake, downloaded Aug. 13, 2019, 6 pages.
www.migraine.com/migraine-treatment/nasal-spray, downloaded Aug. 13, 2019, 6 pages.
www.niddk.nih.gov/health-information/digestive-diseases/chrons-disease, downloaded Aug. 13, 2019, 3 pages.
Zgair et al., "Development of a simple and sensitive HPLC-UV method for the simultaneous determination of cannabidiol and $\Delta^9$-tetrahydrocannabinol in rat plasma" *J Pharmaceut Biomed Anal*, 2015, 114, 145-151.
Written Opinion for International Application No. PCT/EP2018/065223, "Pharmaceutical Formulation", dated Aug. 10, 2018.
International Search Report for International Application No. PCT/EP2017/079217, "Pharmaceutical Formulation", dated Jan. 30, 2019.
International Preliminary Report on Patentability for International Application No. PCT/EP2017/079217, "Pharmaceutical Formulation", dated May 21, 2019.
Written Opinion for International Application No. PCT/EP2017/079217, "Pharmaceutical Formulation", dated May 21, 2019.
International Search Report for International Application No. PCT/EP2019/063376, "Pharmaceutical Formulation" dated Jul. 29, 2019.
Written Opinion of the International Searching Authority for International Application No. PCT/EP2019/063376, "Pharmaceutical Formulation" dated Jul. 29, 2019.
International Preliminary Report on Patentability for International Application No. PCT/EP2019/063376, "Pharmaceutical Formulation" dated Jul. 29, 2019.
Written Opinion of the International Searching Authority for International Application No. PCT/EP2019/062534, "Pharmaceutical Formulation" dated Jul. 29, 2019.
International Search Report for International Application No. PCT/EP2019/062534, "Pharmaceutical Formulation" dated Aug. 26, 2019.
International Preliminary Report on Patentability for International Application No. PCT/EP2019/062534, "Pharmaceutical Formulation" dated Nov. 17, 2020.
Notice of Allowance for U.S. Appl. No. 16/349,840 "Pharmaceutical Formulation" dated Jan. 14, 2021.
Non-Final Office Action for U.S. Appl. No. 16/349,840 "Pharmaceutical Formulation" dated Oct. 6, 2020.
Notice of Allowance for U.S. Appl. No. 16/607,892 "Pharmaceutical Formulation" dated Oct. 1, 2021.
Office Action for U.S. Appl. No. 16/607,892, "Pharmaceutical Formulation" dated Feb. 25, 2021.
Alayoubi, A., et al., "Development of a fast dissolving film of epinephrine hydrocholoride as a potential anaphylactic treatment for pediatrics", harm Dev Technol, Jan. 6, 2016, 7 pages.
Non-Final Office Action for U.S. Appl. No. 17/054,945, "Pharmaceutical Formulation", dated Apr. 20, 2023.
Non-Final Office Action for U.S. Appl. No. 17/054,941 "Pharmaceutical Formulation" dated Apr. 27, 2023.
Dixit, et al., "Iontophoresis—An Approach for Controlled Drug Delivery: A Review", Current Drug Delivery, 2007, 4, 1-10.
Rawas-Qalaji, ct al., "Fast-disintegrating Sublingual Tablets: Effect of Epinephrine Load on Tablet Characteristics", AAPS PharmSciTech 2006; 7 (2) Article 41.
International Preliminary Report on Patentability for international application No. PCT/EP2020/072894, entitled "Film Formulation Comprising Carriers," dated Feb. 24, 2022.
International Search Report for international application No. PCT/EP2020/072894, entitled "Film Formulation Comprising Carriers," dated Oct. 26, 2020.
Written Opinion for international application No. PCT/EP2020/072894, entitled "Film Formulation Comprising Carriers," dated Oct. 26, 2020.
International Search Report for international application No. PCT/EP2020/073940, entitled "Film Formulation Comprising Carriers," dated Dec. 6, 2020.
Written Opinion for international application No. PCT/EP2020/073940, entitled "Pharmaceutical Formulation," dated Dec. 6, 2020.
International Preliminary Report on Patentability for international application No. PCT/EP2020/073940, entitled "Film Formulation Comprising Carriers," dated Mar. 1, 2022.
Klaria Pharma Holding AB, Experimental Report filed on Jul. 28, 2020 in relation to European patent application No. 17804124.0.
Non-Final Office Action for U.S. Appl. No. 17/215,963, "Pharmaceutical Formulation", dated Apr. 13, 2022.
Final Office Action for U.S. Appl. No. 17/054,941 "Pharmaceutical Formulation" dated Aug. 2, 2022.
Final Office Action for U.S. Appl. No. 17/054,945 "Pharmaceutical Formulation" dated Aug. 26, 2022.
Murata, Y., et al., Preparation of Fast Dissolving Films for Oral Dosage from Natural Polysaccharides, Materials, 2010, 3, 4291-4299.

\* cited by examiner

FIG. 1A
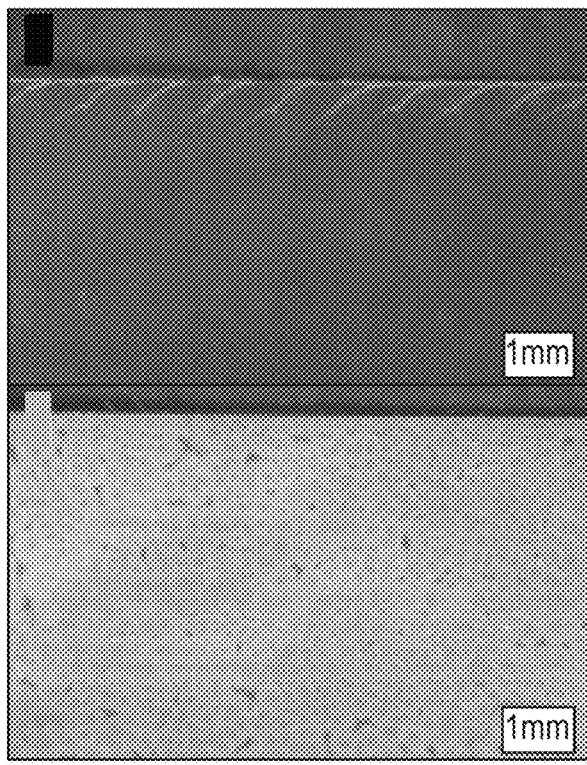
FIG. 1B
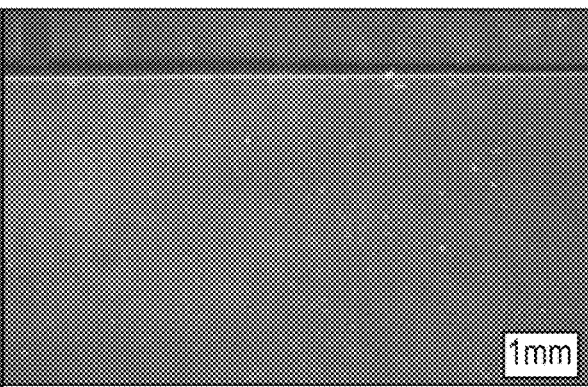
FIG. 1C
FIG. 2
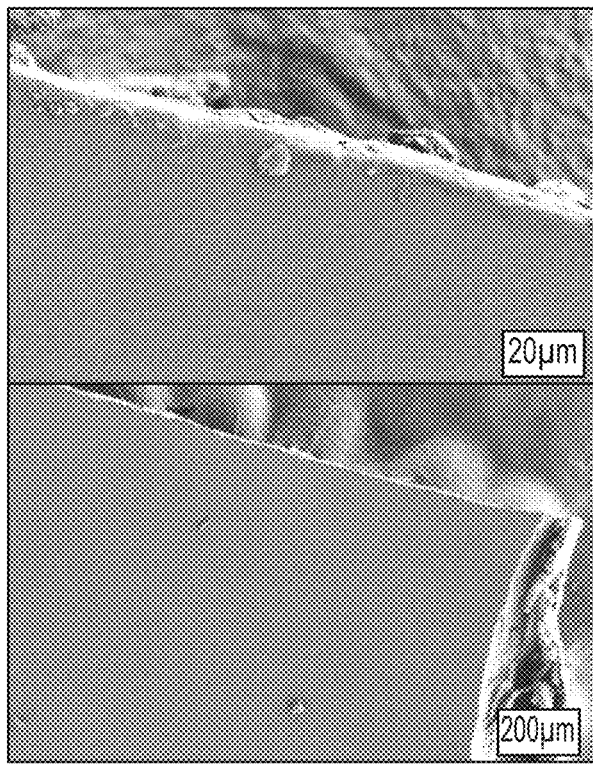
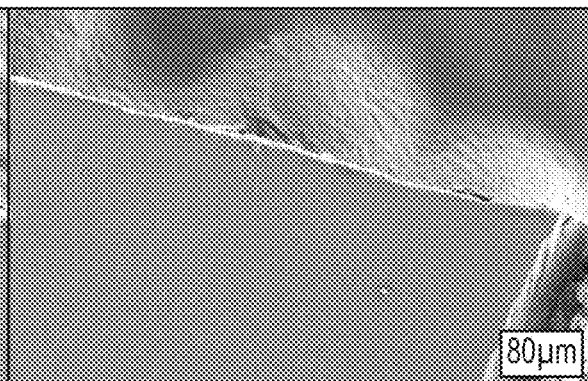

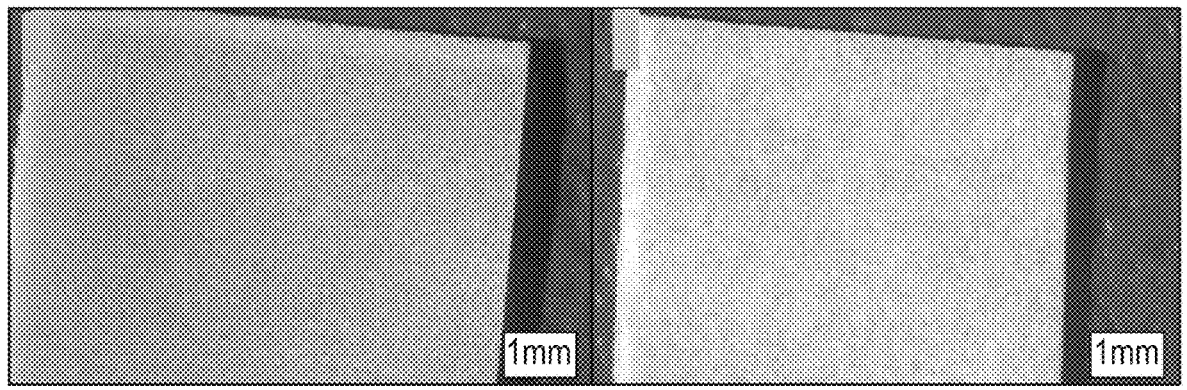
FIG. 4A  FIG. 4B
FIG. 5A
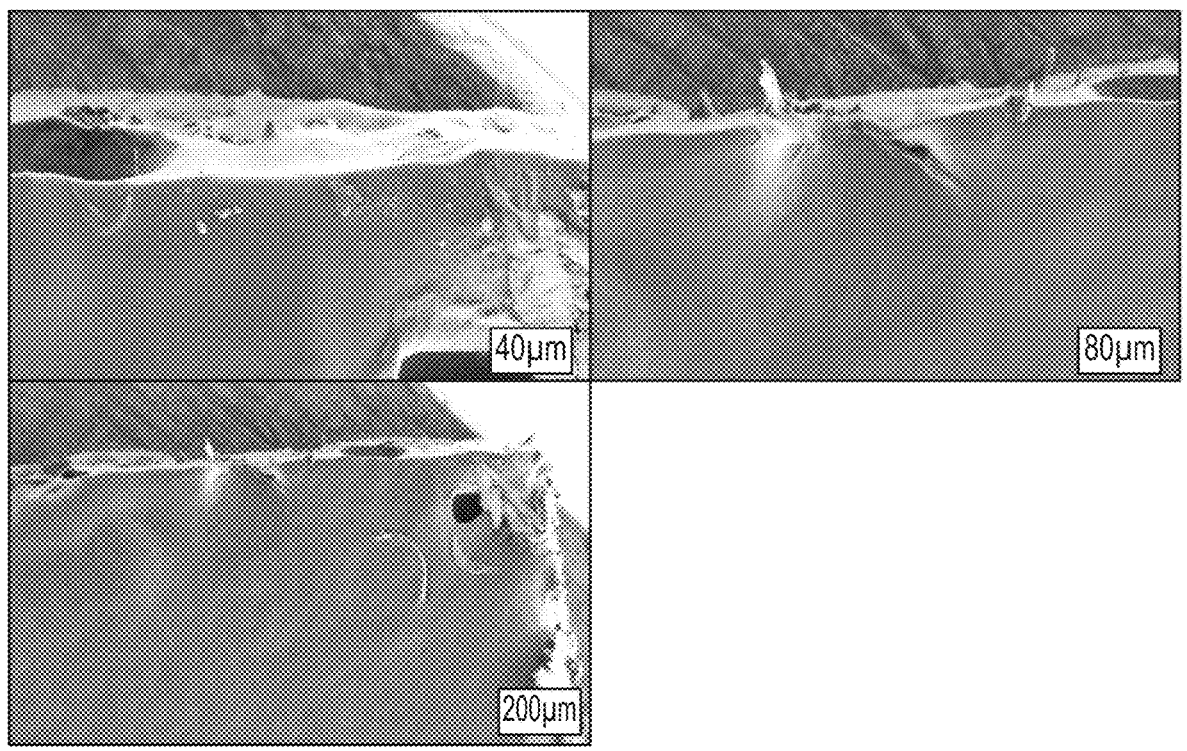

PHARMACEUTICAL FORMULATION

RELATED APPLICATIONS

This application is a continuation of U.S. application Ser. No. 16/607,892 filed on Oct. 24, 2019, which is the U.S. National Stage of International Application No. PCT/EP2018/065223, filed on Jun. 8, 2018, which claims priority under 35 U.S.C. § 119 or 365(c) to Great Britain Application No. 1709141.4, filed on Jun. 8, 2017. The entire teachings of the above applications are incorporated herein by reference.

FIELD OF THE INVENTION

The present invention relates to a film comprising an alginate salt of a monovalent cation or a mixture of alginate salts containing at least one alginate salt of a monovalent cation, and an antagonist of an opioid receptor, an inverse agonist of an opioid receptor, or a prodrug thereof. The present invention further relates to methods for manufacturing such a film, and the use of such a film in the treatment of disease, in particular to reverse the effects of acute opioid overdose or, in combination with an opioid, to lower the risk of opioid abuse.

BACKGROUND TO THE INVENTION

Naloxone may act as a specific antagonist and/or inverse agonist of the opioid receptors. Naloxone acts on the μ-opioid receptor (MOR) with the greatest affinity, followed by the κ-opioid receptor (KOR) and δ-opioid receptor (DOR). In some ligand displacement assays on isolated receptors in membrane preparations, naloxone behaves like an antagonist (i.e. it exhibits no receptor activity in the presence of morphine), and in other assays that measure receptor behaviour after binding in whole cells, naloxone functionally reduces the availability of the receptor to activation, apparently by reducing the levels of functional receptor on the cell surface (i.e. it acts as an inverse agonist) [1]. Currently, naloxone is used therapeutically to reverse the effects of acute opioid overdose and is available as an intravenous injection, intramuscular injection, subcutaneous injection and as a nasal spray. Naloxone is also used in combination with opioids in formulations designed to lower the risk of opioid abuse by formulating naloxone such that intentionally tampering with opioid formulations would release naloxone and diminish the desired effect of the opioid.

In opioid overdose, naloxone is given at a recommended intravenous starting dose of 0.5 mg to 2 mg and can be given at cumulative doses up to 10 mg. Physicians are normally instructed to start therapy at the lowest recommended naloxone dose and titrate the patient every 2 to 3 minutes until the desired response (regaining consciousness) is achieved. The onset of action of intravenous naloxone is 1-3 minutes while intramuscular and nasal formulations may take between 5 and 10 minutes before onset of action occurs. Guidance for constant infusion therapy is also available. The dosing recommendations for constant infusion are 2.5 to 160 mg/kg/hr [2].

The particular advantage of intranasal administration of naloxone is that it can be administered without the use of an injection needle. Injection-free formulations of naloxone can lower the risk of needle-stick injuries in first responders and caregivers. However nasal sprays have thus far shown relatively low (approximately 4%) bioavailability, suggested by trials in human volunteers [3]. New formulations which administer a more highly concentrated solution intranasally in order to improve bioavailability are being investigated [4].

While the onset of action after either intramuscular and intranasal administration is somewhat slower than intravenous administration, the delay in absorption is acceptable due to the total time required to achieve pharmacological effect when the time necessary for intravenous intubation is considered. Intramuscular administration however involves the training and monitoring of first responders/caregivers in the risks of needle-stick injuries. Nasal sprays, while offering a needle-free administration give somewhat lower and more variable absorption which may not achieve pharmacologically adequate levels in all patients. Therefore, a needle-free alternative to nasal administration for naloxone in acute opioid overdose would be advantageous for both patient and caregiver.

In summary, no formulation of naloxone is currently available which can be administered in a non-invasive fashion, is needle-free and which results in acceptable bioavailability and blood plasma concentrations of naloxone with low variability between patients.

SUMMARY OF THE INVENTION

The present invention is based on the unexpected finding that formulations of an antagonist of an opioid receptor, an inverse agonist of an opioid receptor, or a prodrug thereof, in a film suitable for administration to an oral cavity can provide a desirable balance of properties for use in the treatment of the effects of acute opioid overdose, or in reducing the risk of opioid abuse. In particular, where the antagonist of an opioid receptor is naloxone or a pharmaceutically acceptable salt thereof, it is an unexpected finding of the present invention that the properties of a naloxone-containing film compare favourably with those of other naloxone-containing formulations, for example intravenous, intramuscular or nasal spray formulations. In particular, it is a surprising finding of the present invention that when films as herein defined containing (−)-naloxone are administered to beagle dogs in a test study, desirable plasma concentrations of (−)-naloxone above 1 ng/mL were reached within a few minutes, and peak plasma concentrations of (−)-naloxone were reached within 30 minutes.

Hence, the invention provides for the first time a film suitable for administration to an oral cavity comprising an antagonist of an opioid receptor, an inverse agonist of an opioid receptor, or a prodrug thereof, its use in the treatment of patients suffering from the effects of acute opioid overdose, and its use in reducing the risk of opioid abuse in a human subject.

In one aspect, the present invention provides a film suitable for administration to an oral cavity comprising:
(i) an alginate salt of a monovalent cation or a mixture of alginate salts containing at least one alginate salt of a monovalent cation; and
(ii) an active pharmaceutical ingredient (API) which is an antagonist of an opioid receptor, an inverse agonist of an opioid receptor, or a prodrug thereof;
wherein the alginate salt of a monovalent cation (a) comprises from 25 to 35% by weight of β-D-mannuronate and/or from 65 to 75% by weight of α-L-guluronate, and (b) has a mean molecular weight of from 30,000 g/mol to 90,000 g/mol.

In another aspect, the present invention provides a film according to the invention for use in the treatment of a human patient.

In another aspect, the present invention provides a film according to the invention for use in the treatment of the effects of acute opioid overdose, or for use in reducing the risk of opioid abuse, in a human patient.

In a further aspect, the present invention provides a method of treating the effects of acute opioid overdose in a human patient, or for reducing the risk of opioid abuse in a human patient, wherein said method comprises administration of at least one film according to the invention to the human patient.

In another aspect, the present invention provides the use of a film according to the invention for the manufacture of a medicament for the treatment of the effects of acute opioid overdose in a human patient, or for reducing the risk of opioid abuse in a human patient.

In another aspect, the present invention provides a method of manufacturing a film according to the invention, said method comprising the following steps:

(A) either the steps of:
  (a) optionally, mixing one or more preservatives in water;
  (b) either: (i) mixing the API as defined in any one of claims 1 to 16 and, optionally, at least one buffering component in water, or in the solution obtained in step (a), and subsequently adjusting the pH of the resultant solution to the desired level by addition of an appropriate acid or base, typically a diluted aqueous acid or alkali, and preferably adjusting the pH of the solution to from 3.0 to 12.0; or
  (ii) adjusting the pH of water, or the solution obtained in step (a), to the desired level by addition of an appropriate acid or base, typically a diluted aqueous acid or alkali, and preferably adjusting the pH to from 3.0 to 12.0, and subsequently mixing the API as defined in any one of claims 1 to 16 and, optionally, at least one buffering component in the pH-adjusted solution;
  (c) optionally, adding further water and/or one or more plasticizers under further mixing;
  (d) adding the alginate salt of monovalent cation under suitable conditions to result in the formation of a viscous cast;
  or alternatively the steps of:
    (i) mixing one or more excipients and one or more preservatives in an acidic aqueous solution;
    (ii) separately, dissolving the API in water;
    (iii) mixing the solution obtained in step (i) with the alginate salt of monovalent cation;
    (iv) adding the solution obtained in step (ii) to the solution obtained in step (iii) under suitable conditions to result in the formation of a viscous cast;
    (v) optionally, adding a chelating agent to the cast;
(B) optionally, leaving the cast to de-aerate;
(C) pouring the cast onto a surface and spreading the cast out to the desired thickness;
(D) drying the cast layer, typically at a temperature of from 40 to 70° C. until the residual water content of the film is from 5 to 15% by weight and a solid film is formed; and
(E) optionally, cutting the solid film into pieces of the desired size, further optionally placing these pieces into pouches, preferably wherein the pouches are made from PET-lined aluminium, sealing the pouches and further optionally, labelling them.

BRIEF DESCRIPTION OF THE DRAWINGS

FIGS. 1A-1C: Light microscope images of low pH (−)-naloxone buccal films. The films were formulated from a film formulation mixture comprising (−)-naloxone hydrochloride dihydrate. (FIG. 1A) 2 mg/dose film (pH 4.2); (FIG. 1B) 10 mg/dose film (pH 5.2); (FIG. 1C) 20 mg/dose film (pH 5.2).

FIG. 2: Scanning electron micrograph images of 10 mg low pH (−)-naloxone buccal film. The films were formulated from a film formulation mixture comprising (−)-naloxone hydrochloride dihydrate at a pH of 4.2.

FIGS. 4A-4B: Light microscope images of high pH (−)-naloxone buccal films. The films were formulated from a film formulation mixture comprising 10 mg (−)-naloxone at a pH of 9. (FIG. 4A) Batch #2; (FIG. 4B) Batch #3.

FIGS. 5A-5C: Scanning electron micrograph images of 10 mg high pH (−)-naloxone buccal film. (FIG. 5A) Batch #2; (FIG. 5B) Batch #3; (FIG. 5C) Batch #26. The films were formulated from a film formulation mixture comprising (−)-naloxone at a pH of 9.

(FIG. 8B) citric acid and EDTA (batch #15). The films were formulated from a film formulation mixture comprising (−)-naloxone at a pH of 4.2.

(FIG. 9B) oleic acid as part of SNEDDS, and EDTA (batch #20).

Sol=control solution. The flux from Formulations A and D was slightly higher compared with the other formulations.

Figure 13:
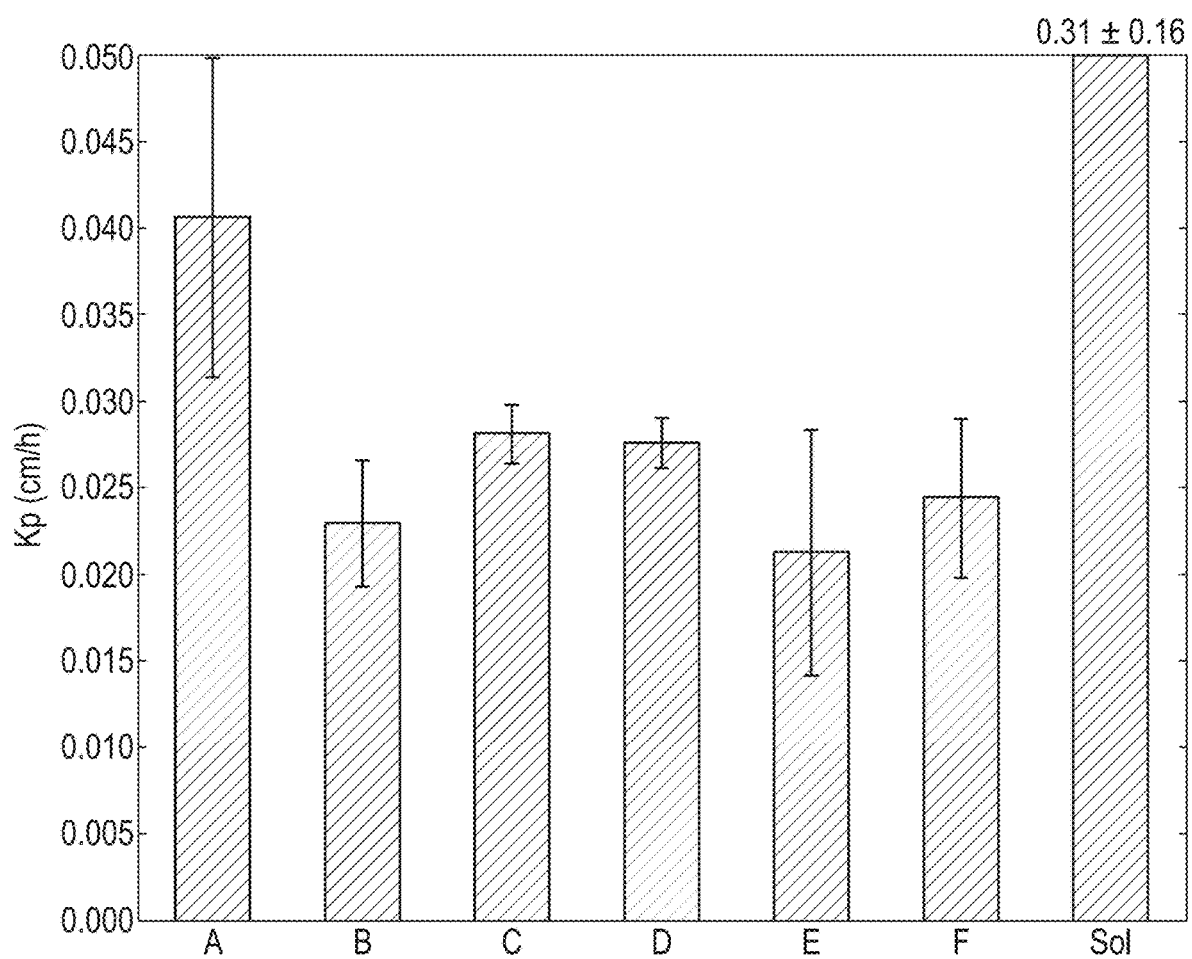
Figure 14A:
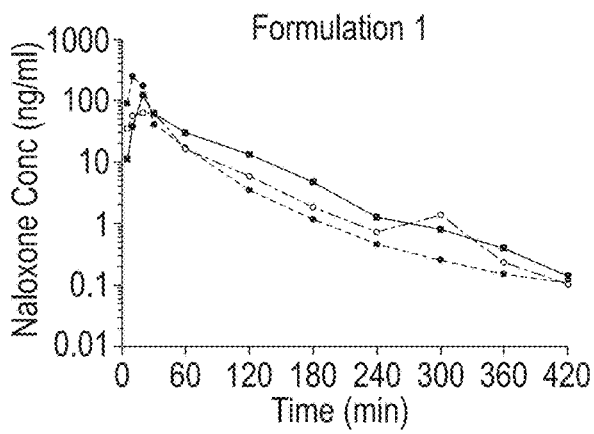
Figure 14B:
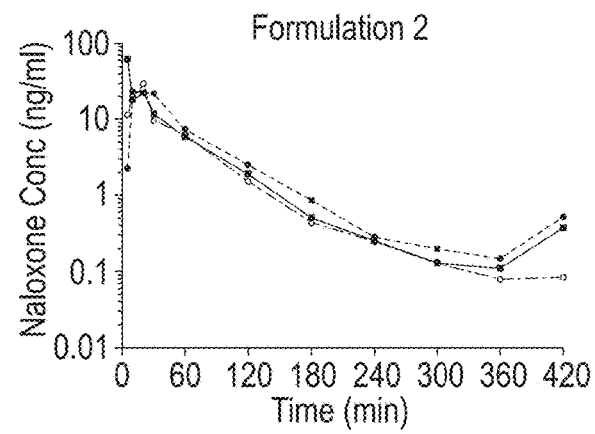
Figure 14C:
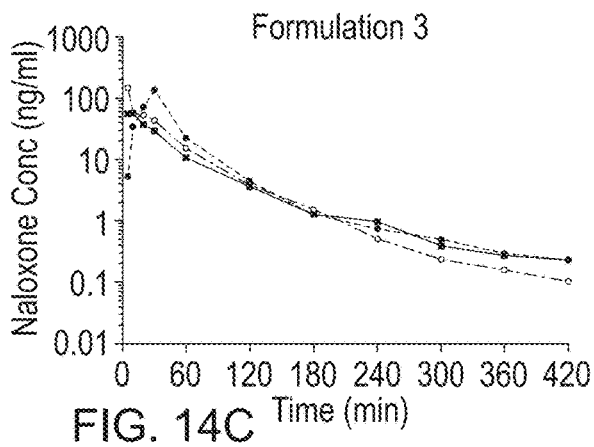
Figure 14D:
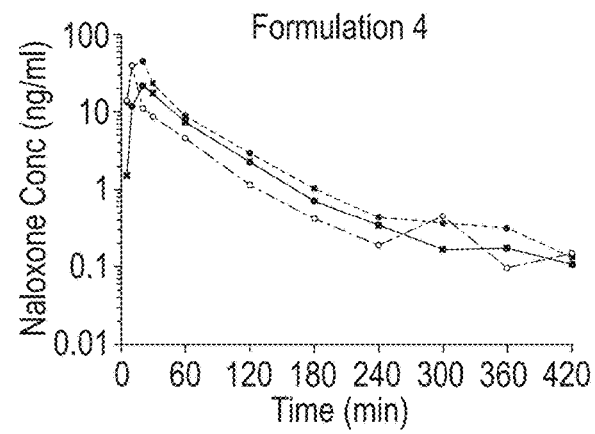
Figure 14E:
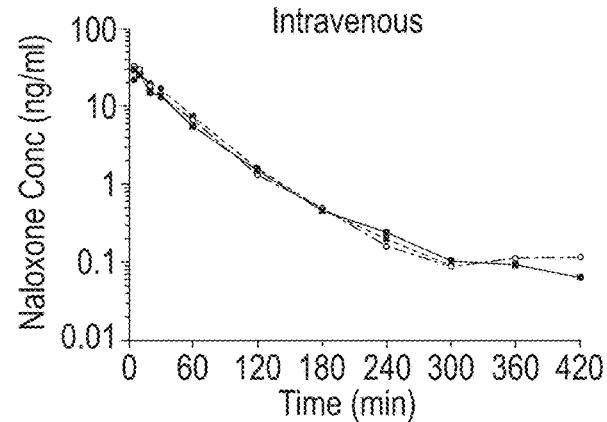

FIG. 13: Permeation coefficient (Kp) values for the studied (−)-naloxone Formulations A-F and the control solution. The values are presented as mean±standard deviation. For the control solution, the bar extends off the scale illustrated: the control solution has a measured Kp value of 0.31±0.16 cm/h.

FIGS. 14A-14E: Individual plasma naloxone concentration versus time curves for 3 Beagle dogs given (−)-naloxone film Formulations 1~4 (10 mg) or intravenous naloxone (0.143 mg/kg). It should be noted that the Y-axis scale is 0.01 to 1000 ng/mL for Formulations 1 and 3, whilst the Y-axis scale is 0.01 to 100 ng/mL for the remaining formulations. The earliest time point at which blood samples were taken is 5 minutes after initial application of the buccal film, or after injection, and the last time point is 420 minutes after dosing in all cases.

Figure 15:
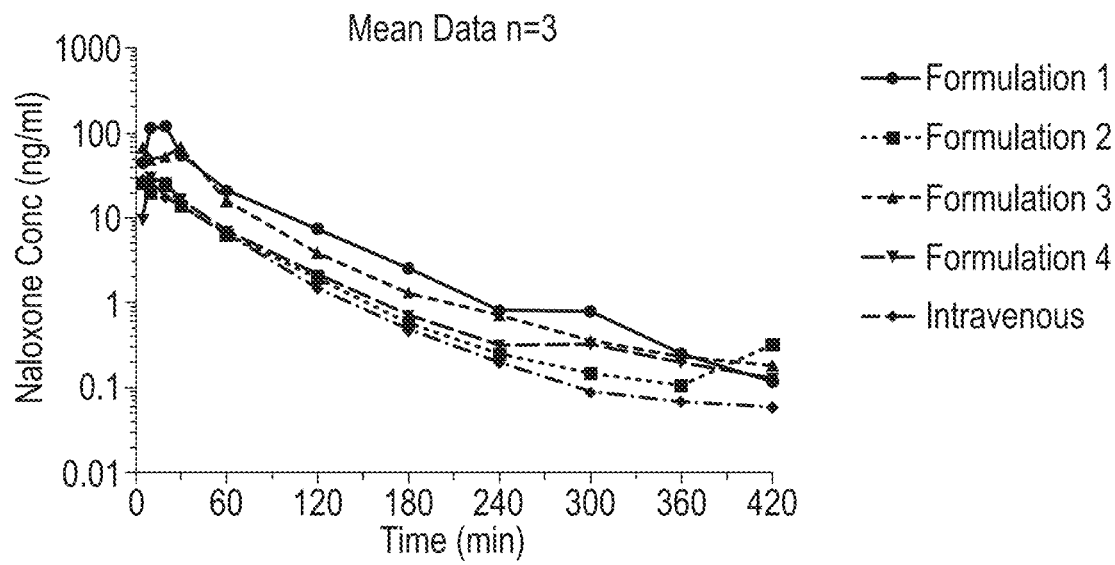

FIG. 15: Mean plasma naloxone concentration versus time curve for the four buccal film formulations studied in the Beagle dog screen. Mean plasma levels are also given after a single intravenous dose. All buccal film formulations contained 10 mg total dose and the intravenous dose was given at 0.143 mg/kg body weight (mean total i.v. dose given was 1.92 mg).

Figure 16:
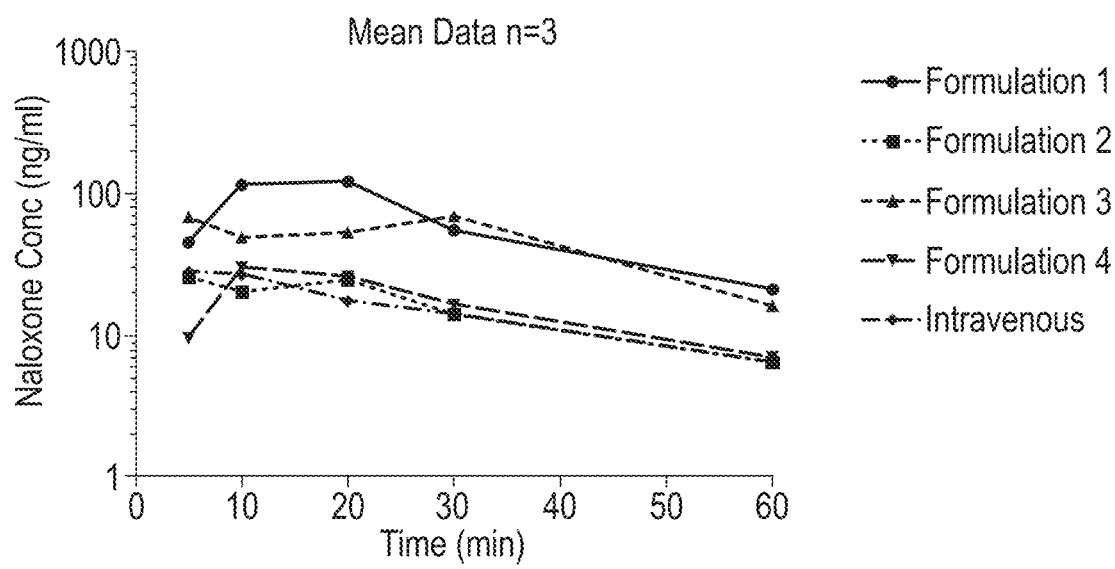

FIG. 16: Mean plasma naloxone concentration versus time curves for the first 60 minutes after administration for the four buccal film formulations studied in the Beagle dog screen.

Figure 17:
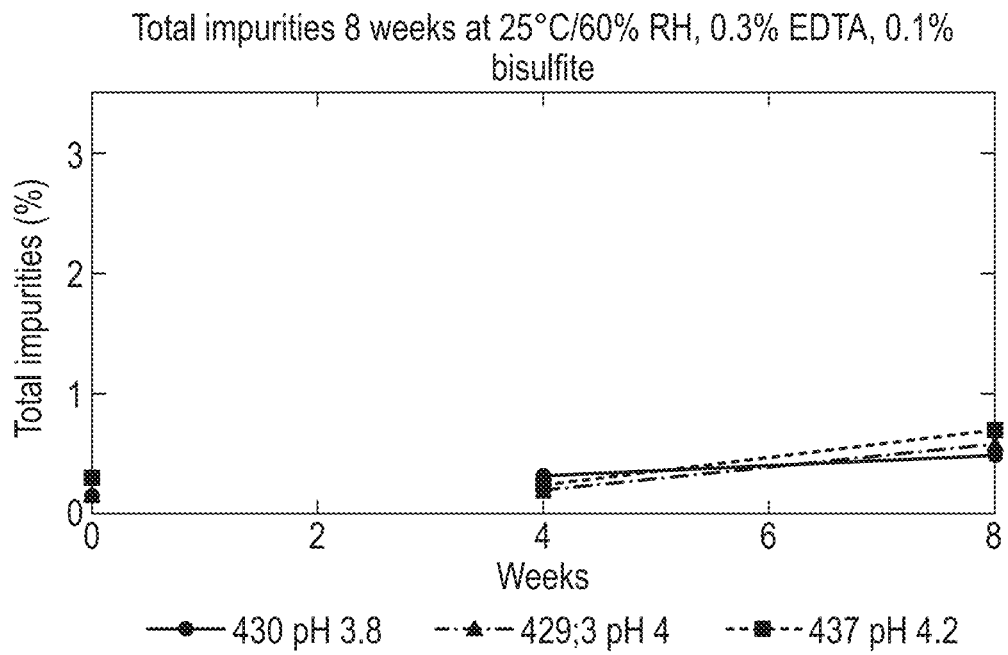

FIG. 17: Total amount of impurities present (in weight %) for films comprising naloxone as the API, 0.3% by weight of EDTA and 0.1% by weight of sodium bisulfite, which were stored in PET-lined aluminium pouches at 25° C. and 60% relative humidity. Analysis was carried out after storage at 0, 4 and 8 weeks. Square data points: film formulations having a pH of 4.2 prior to drying and coating. Triangular data points: film formulations having a pH of 4.0 prior to drying and coating. Circular data points: film formulations having a pH of 3.8 prior to drying and coating.

Figure 18:
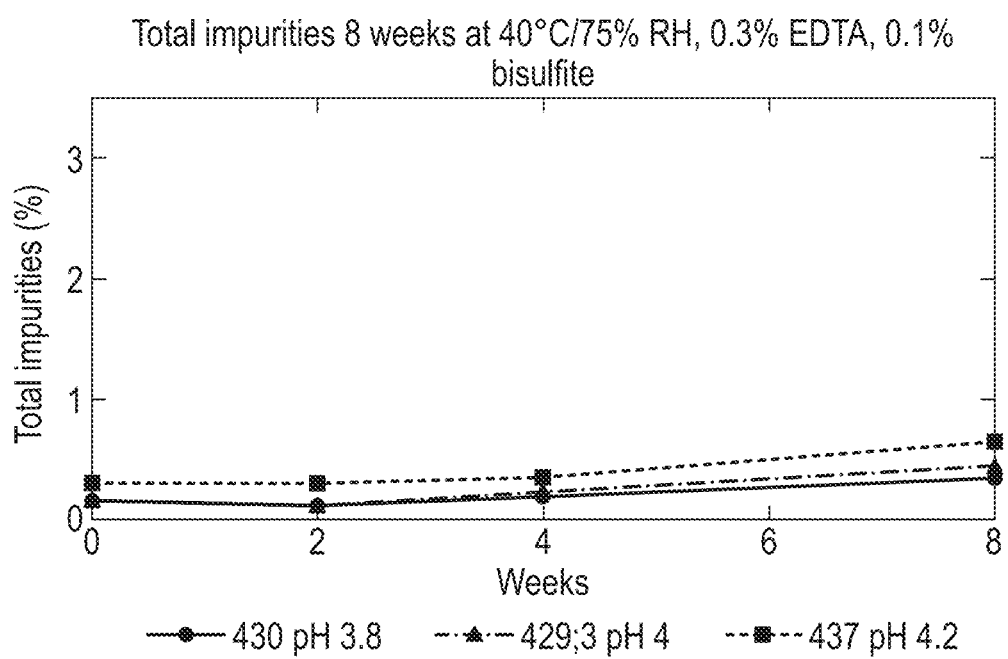

FIG. 18: Total amount of impurities present (in weight %) for films comprising naloxone as the API, 0.3% by weight of EDTA and 0.1% by weight of sodium bisulfite, which were stored in PET-lined aluminium pouches at 40° C. and 75% relative humidity. Analysis was carried out after storage at 0, 4 and 8 weeks. Square data points: film formulations having a pH of 4.2 prior to drying and coating. Triangular data points: film formulations having a pH of 4.0 prior to drying and coating. Circular data points: film formulations having a pH of 3.8 prior to drying and coating.

Figure 19:
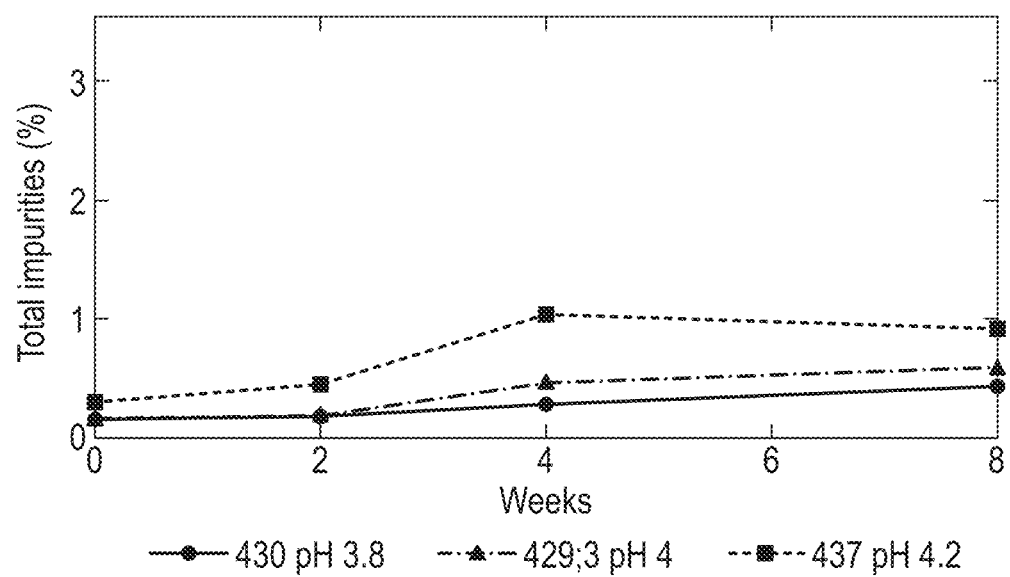

FIG. 19: Total amount of impurities present (in weight %) for films comprising naloxone as the API, 0.3% by weight of EDTA and 0.1% by weight of sodium bisulfite, which were stored in PET-lined aluminium pouches at 50° C. and 75% relative humidity. Analysis was carried out after storage at 0, 4 and 8 weeks. Square data points: film formulations having a pH of 4.2 prior to drying and coating. Triangular data points: film formulations having a pH of 4.0 prior to drying and coating. Circular data points: film formulations having a pH of 3.8 prior to drying and coating.

DETAILED DESCRIPTION

The present invention is concerned with a film, suitable for administration to an oral cavity, which can be used for delivery of an antagonist of an opioid receptor, an inverse agonist of an opioid receptor, or a prodrug thereof to a human patient. Such a film may also be referred to as an oral dissolvable film (ODF) and/or an oral transmucosal film (OTF). The film is typically an alginate film which is applied by the patient themselves or another person, e.g. a medical practitioner, a nurse, a carer, a social worker, or a family member of the patient, to the mucosa of the oral cavity. The film is bioadhesive and adheres to the surface of the oral cavity upon application. After application, the alginate film begins to dissolve, releasing the active pharmaceutical ingredient. The present invention is useful in particular in treatment of the effects of acute opioid overdose, or for use in reducing the risk of opioid abuse.

For the avoidance of doubt, all alternative and preferred features relating to the film per se apply equally to the use of said film in the treatment of a human patient.

Definitions

As defined herein, the term "alkyl" refers to a linear or branched saturated monovalent hydrocarbon radical having the number of carbon atoms indicated in the prefix. Thus, the term "$C_{1-4}$ alkyl" refers to a linear saturated monovalent hydrocarbon radical of one to four carbon atoms or a branched saturated monovalent hydrocarbon radical of three or four carbon atoms, e.g. methyl, ethyl, n-propyl, iso-propyl, n-butyl, iso-butyl and tert-butyl.

As defined herein, the term "acyl" refers to a —COR radical, wherein R is alkyl, haloalkyl, cycloalkyl, cycloalkylalkyl, aryl, aralkyl, heteroaryl, heteroaralkyl, heterocyclyl, or heterocyclylalkyl, each as defined herein, or poly(ethylene glycol), and wherein R is optionally further substituted with one, two, three, four or more substituents independently selected from alkyl, alkoxy, halo, haloalkoxy, —OH, —NH$_2$, alkylamino, —COOH, or alkoxycarbonyl.

As defined herein, the term "alkoxy" refers to an —OR radical where R is alkyl as defined above, e.g., methoxy, ethoxy, n-propoxy, iso-propoxy, n-butyl, iso-butyl, tert-butyl and the like.

As defined herein, the term "alkoxycarbonyl" or "ester" refers to a —C(O)OR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, or poly(ethylene glycol), and wherein R is optionally further substituted with one, two, three, four or more substituents independently selected from alkyl, alkoxy, halo, haloalkoxy, —OH, —NH$_2$, alkylamino, —COOH, or alkoxycarbonyl.

As defined herein, the term "alkylamino" refers to an —NHR radical where R is alkyl as defined above, e.g. methylamino, ethylamino, n-propylamino, iso-propylamino, and the like.

As defined herein, the term "aryl" refers to a monovalent monocyclic or bicyclic aromatic hydrocarbon radical of 6 to 10 ring atoms, e.g. phenyl or naphthyl, and the like.

As defined herein, the term "aralkyl" refers to an -(alkylene)-R radical where R is aryl as defined above.

As defined herein, the term "carbamyl" refers to a —C(O)NR$^x$R$^y$ radical where R$^x$ and R$^y$ are independently hydrogen, alkyl, haloalkyl, cycloalkyl, cycloalkylalkyl, aryl, aralkyl, heteroaryl, heteroaralkyl, heterocyclyl, or heterocyclylalkyl, each as defined herein, or poly(ethylene glycol), and wherein R$^x$ and R$^y$ are optionally further substituted with one, two, three, four or more substituents independently selected from alkyl, alkoxy, halo, haloalkoxy, —OH, —NH$_2$, alkylamino, —COOH, or alkoxycarbonyl.

As defined herein, the term "cycloalkyl" refers to a cyclic saturated monovalent hydrocarbon radical of three to ten carbon atoms wherein one or two carbon atoms may be replaced by an oxo group, e.g. cyclopropyl, cyclobutyl, cyclopentyl, or cyclohexyl, and the like.

As defined herein, the term "cycloalkylalkyl" refers to an -(alkylene)-R radical where R is cycloalkyl as defined above, e.g. cyclopropylmethyl, cyclobutylmethyl, cyclopentylethyl, or cyclohexylmethyl, and the like.

As defined herein, the term "film-forming agent" refers to a compound or group of compounds that form a pliable, cohesive and continuous covering when applied to a surface.

As defined herein, the term "halo" refers to fluoro, chloro, bromo, or iodo, preferably fluoro or chloro.

As defined herein, the term "haloalkyl" refers to an alkyl radical as defined above, which is substituted with one or more halogen atoms, preferably one to five halogen atoms, preferably fluorine or chlorine, including those substituted with different halogens, e.g. —$CH_2Cl$, -$CF_3$, —$CHF_2$, —$CH_2CF_3$, —$CF_2CF_3$, —$CF(CH_3)_2$, and the like.

As defined herein, the term "haloalkoxy" refers to an —OR radical where R is haloalkyl as defined above, e.g. —$OCF_3$, —$OCHF_2$, and the like.

As defined herein, the term "heteroaryl" refers to a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

As defined herein, the term "heteroaralkyl" refers to an -(alkylene)-R radical where R is heteroaryl as defined above.

As defined herein, the term "heterocycyl" refers to a saturated or unsaturated monovalent monocyclic group of 4 to 8 ring atoms in which one or two ring atoms are heteroatoms selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds, provided that the ring is not aromatic.

As defined herein, the term "heterocycloalkyl" refers to an -(alkylene)-R radical where R is heterocyclyl ring as defined above, e.g. tetraydrofuranylmethyl, piperazinylmethyl, morpholinylethyl, and the like.

The term "oral cavity" is understood to mean the cavity of the mouth, and includes the inner upper and lower lips, all parts of the inner cheek, the sublingual area under the tongue, the tongue itself, as well as the upper and lower gums and the hard and soft palate.

The term "oral mucosa" is understood to mean the mucous membrane lining the inside of the mouth, and includes (but does not exclusively refer to) mucosa in the buccal, labial, sublingual, gingival or lip areas, the soft palate and the hard palate.

Films of the Present Invention

The present invention provides a film suitable for administration to an oral cavity comprising:

(i) an alginate salt of a monovalent cation or a mixture of alginate salts containing at least one alginate salt of a monovalent cation; and (ii) an active pharmaceutical ingredient (API) which is an antagonist of an opioid receptor, an inverse agonist of an opioid receptor, or a prodrug thereof.

The function of said alginate salt of a monovalent cation or mixture of alginate salts containing at least one alginate salt of a monovalent cation within the film is to act as a film-forming agent.

Alginate, the salt of alginic acid, is a linear polysaccharide naturally produced by brown seaweeds (Phaeophyceae, mainly *Laminaria*). Typically the alginate employed in the present invention comprises from 100 to 3000 monomer residues linked together in a flexible chain. These residues are of two types, namely β-(1,4)-linked D-mannuronic acid (M) residues and α-(1,4)-linked L-guluronic acid (G) residues. Typically, at physiological pH, the carboxylic acid group of each residue in the polymer is ionised. The two residue types are epimers of one another, differing only in their stereochemistry at the C5 position, with D-mannuronic acid residues being enzymatically converted to L-guluronic acid residues after polymerization. However, in the polymer chain the two residue types give rise to very different conformations: any two adjacent D-mannuronic acid residues are $^4C_1$-diequatorially linked whilst any two adjacent L-guluronic acid residues are $^4C_1$-diaxially linked, as illustrated in Formula (I) below.

Formula (I)

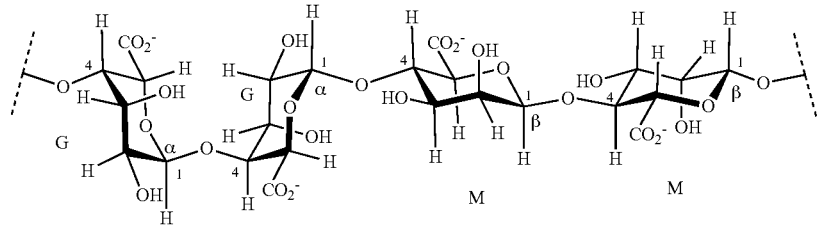

Typically in the alginate polymer, the residues are organised in blocks of identical or strictly alternating residues, e.g. MMMMM . . . , GGGGG . . . or GMGMGM . . . . Different monovalent and polyvalent cations may be present as counter ions to the negatively-charged carboxylate groups of the D-mannuronic acid and L-guluronic acid residues of the alginate polymer. Typically, the film comprises an alginate salt wherein the counter ions of the alginate polymer are monovalent cations. The cations which are the counterions of a single alginate polymer molecule may all be the same as one another or may be different to one another. Preferably, the counterions of the alginate polymer are selected from the group consisting of Na$^+$, K$^+$ and NH$_4^+$. More preferably, the counterions of the alginate polymer are Na$^+$. Alternatively, the film may comprise a mixture of alginate salts containing at least one alginate salt of a monovalent cation. The mixture of alginate salts may comprise an alginate salt of a cation selected from the group consisting of Na$^+$, K$^+$ and NH$_4^+$.

Typically, the film comprises an alginate composition which has a dynamic viscosity, as measured on a 10% aqueous solution (w/w) thereof at a temperature of 20° C. with a Brookfield LVF viscometer (obtained from Brookfield Engineering Laboratories, Inc.), using a spindle No. 2 at a shear rate of 20 rpm, of 100-1000 mPa·s, or 200-800 mPa·s, or 300-700 mPa·s.

Preferably, the film comprises an alginate composition having a mean guluronate (G) content of from 50 to 85%, more preferably from 60 to 80%, and most preferably from 65 to 75% by weight. Preferably, the film comprises an alginate composition having a mean maluronate (M) content of from 15 to 50%, more preferably from 20 to 40%, and most preferably from 25 to 35% by weight. Typically, the film comprises an alginate composition having a mean molecular weight ranging from 20,000 g/mol to 90,000 g/mol. Preferably, the film comprises an alginate composition having a mean molecular weight ranging from 30,000 g/mol to 90,000 g/mol, such as from 35,000 g/mol to 85,000 g/mol, preferably from 40,000 g/mol to 70,000 g/mol, more preferably from 40,000 to less than 60,000 g/mol and even more preferably from 40,000 g/mol to 50,000 g/mol. Preferably, the film comprises an alginate composition having a mean guluronate (G) content of from 50 to 85%, a mean maluronate (M) content of from 15 to 50%, and a mean molecular weight ranging from 30,000 g/mol to 90,000 g/mol. More preferably, the film comprises an alginate composition having a mean guluronate (G) content of from 60 to 80%, a mean maluronate (M) content of from 20 to 40%, and a mean molecular weight ranging from 30,000 g/mol to 90,000 g/mol. Even more preferably, the film comprises an alginate composition having a mean guluronate (G) content of from 65 to 75%, a mean maluronate (M) content of from 25 to 35%, and a mean molecular weight ranging from 30,000 g/mol to 90,000 g/mol. Most preferably, the film comprises an alginate composition having a mean guluronate (G) content of from 65 to 75%, a mean maluronate (M) content of from 25 to 35%, and a mean molecular weight ranging from 40,000 g/mol to 50,000 g/mol.

The alginate salt of a monovalent cation or the mixture of alginate salts containing at least one alginate salt of a monovalent cation may be the sole film-forming agent present in the film. Alternatively, the film may comprise one or more further film-forming agents in addition to the alginate salt of a monovalent cation or the mixture of alginate salts containing at least one alginate salt of a monovalent cation.

It is preferred that the film comprises Protanal® LFR 5/60 or Protanal® LF 10/60 (both commercially available sodium alginate products from FMC BioPolymer) as the alginate salt. Protanal® LFR 5/60 is a low molecular weight and low viscosity sodium alginate extracted from the stem of *Laminaria hyperborean*. Protanal® LF 10/60 is a sodium alginate having a G/M % ratio of 65-75/25-35 and a viscosity of from 20-70 mPas as measured on a 1% aqueous solution thereof at a temperature of 20° C. with a Brookfield LVF viscometer, using a spindle No. 2 at a shear rate of 20 rpm. Protanal® LF 10/60 has both a higher mean molecular weight and a higher viscosity than Protanal® LFR 5/60.

Without wishing to be bound by any particular theory, a film comprising a higher viscosity alginate salt is believed to have a longer residence time (i.e. dissolving time) after application to the oral cavity via adhesion to a mucous membrane of said cavity than a film comprising a lower viscosity alginate salt of a similar thickness. It is contemplated that the viscosity of the alginate composition within the film may be adjusted by mixing any number of alginates having different viscosities. Typically, a film of about 1 mm thickness comprising Protanal® LFR 5/60 as the sole alginate component has a residence time of approximately 3-10 minutes after adhesion to a mucous membrane of the oral cavity. In contrast, a film of about 1 mm thickness comprising Protanal® LF 10/60 as the sole alginate component has a residence time of approximately 30 minutes after adhesion to a mucous membrane of the oral cavity.

Therefore, if a long residence time of the film within the oral cavity is desired, it is generally preferred that the film comprises Protanal® LF 10/60 as the alginate salt. However, compared to films comprising Protanal® LFR 5/60 as the alginate salt, films comprising Protanal® LF 10/60 as the alginate salt typically exhibit inferior adhesion properties when applied to a mucous membrane of the oral cavity. Without wishing to be bound by any particular theory, it is believed that better mucoadhesion of a film to the mucous membrane of the oral cavity enables a more efficient delivery of any active ingredients contained within the film to their site of action. Therefore, if a long residence time of the film within the oral cavity is not particularly necessary, it may be preferable to use Protanal® LFR 5/60 as the alginate salt.

It is particularly preferred that the film comprises Protanal® LFR 5/60 as the alginate salt.

Without wishing to be bound by any particular theory, it is believed that both the ratio of mannuronate to guluronate in the alginate salt and the molecular weight of the alginate salt may have an effect on the mucoadhesion properties of the film. In particular, it is believed that an increase in molecular weight of the alginate polymer may lead to a decrease in adhesive properties.

Preferably, the film does not comprise any, or substantially any, Manucol® LB as the alginate salt of a monovalent cation.

The film may also comprise a film-forming agent other than the alginate salt of a monovalent cation or the mixture of alginate salts containing at least one alginate salt of a monovalent cation. Such other film-forming agents include agents such as poly(vinyl pyrrolidone) (PVP), hydroxypropylmethylcellulose (HPMC), pullulan, starch and so forth. However, if any other film-forming agent is present in the film in addition to the alginate salt of a monovalent cation or the mixture of alginate salts containing at least one alginate salt of a monovalent cation, then typically the alginate salt of a monovalent cation or the mixture of alginate salts containing at least one alginate salt of a monovalent cation will be present in the film in excess over any other film-forming agent present. Preferably, the ratio (by weight) of the alginate salt of a monovalent cation or the mixture of alginate salts containing at least one alginate salt of a monovalent cation present in the film to the combined total of all other film-forming agents (such as PVP, HPMC, pullulan and/or starch) present in the film is 1:1 or greater, or 2:1 or greater, or 3:1 or greater, or 4:1 or greater, or 5:1 or greater, or 10:1 or greater, or 20:1 or greater, or 50:1 or greater, or 100:1 or greater, or 500:1 or greater, or 1000:1 or greater, or 10000:1 or greater. Preferably, the alginate salt of a monovalent cation or the mixture of alginate salts containing at least one alginate salt of a monovalent cation will constitute at least 50% by weight of the total of the film-forming agents present in the film, more preferably at least 60% by weight, at least 70% by weight, at least 80% by weight, at least 90% by weight, at least 95% by weight, at least 98% by weight, at least 99% by weight, at least 99.5% by weight, at least 99.9% by weight, at least 99.95% by weight, or at least 99.99% by weight of the total of the film-forming agents present in the film.

Preferably, the alginate salt of a monovalent cation or the mixture of alginate salts containing at least one alginate salt of a monovalent cation is substantially the only film-forming agent present in the film. More preferably, the alginate salt of a monovalent cation or the mixture of alginate salts containing at least one alginate salt of a monovalent cation is the only film-forming agent present in the film. Alternatively, the film preferably does not comprise any, or substantially any, poly(vinyl pyrrolidone). Alternatively, the film preferably does not comprise any, or substantially any, hydroxypropylmethylcellulose. Alternatively, the film preferably does not comprise any, or substantially any, pullulan. Alternatively, the film preferably does not comprise any, or substantially any, starch.

As used herein, a reference to a film that does not comprise "substantially any" of a specified component refers to a film that may contain trace amounts of the specified component, provided that the specified component does not materially affect the essential characteristics of the film. Typically, therefore, a film that does not comprise substantially any of a specified component contains less than 5 wt % of the specified component, preferably less than 1 wt % of the specified component, most preferably less than 0.1 wt % of the specified component.

It is a finding of the present invention that the use of an alginate salt of a monovalent cation or a mixture of alginate salts containing at least one alginate salt of a monovalent cation as the film-forming agent has benefits over the use of alternative film-forming agents, such as PVP, HPMC, pullulan and/or starch. In particular, the use of alginate as the primary film-forming agent ensures that the films of the present invention have superior adhesive properties over films comprising primarily other film-forming agents such as PVP, HPMC, pullulan and/or starch. The films of the present invention are bioadhesive; that is to say that the films of the present invention can firmly adhere to a moist surface (i.e. mucosa) in the oral cavity of a mammal subject before it has fully dissolved. Films in which alginate is not the primary film-forming agent do not generally have this desirable property. A further advantageous finding of the present invention is that the choice of alginate as the primary film-forming agent enables therapeutically effective doses of an active pharmaceutical ingredient (e.g. naloxone) to be loaded into the films whilst retaining homogeneity and other desirable physical properties of the films.

Typically, the film comprises from 25% to 99% by weight of the alginate salt of a monovalent cation or the mixture of alginate salts containing at least one alginate salt of a monovalent cation, preferably from 27% to 95% by weight, more preferably from 29% to 93% by weight, still more preferably from 30% to 91% by weight, and most preferably from 35% to 90% by weight.

The film according to the present invention may also contain a residual water content. Typically, the film comprises from 0% to 20% by weight of residual water. More typically, the film comprises from 5% to 15% by weight of residual water. Preferably, the film comprises from 9% to 11% by weight of residual water. Most preferably, the film comprises about 10% by weight of residual water.

The film according to the present invention also comprises an active pharmaceutical ingredient (API) which is an antagonist of an opioid receptor, an inverse agonist of an opioid receptor, or a prodrug thereof. Preferably the API is an antagonist of an opioid receptor or an inverse agonist of an opioid receptor. The antagonist of an opioid receptor, inverse agonist of an opioid receptor, or the prodrug thereof is present in a therapeutically effective amount in the film. Typically, the API is an antagonist of an opioid receptor. Alternatively, the API is an inverse agonist of an opioid receptor. Alternatively, the API may act as either an antagonist or an inverse agonist of an opioid receptor. Alternatively, the API may be a prodrug of an antagonist of an opioid receptor. Alternatively, the API may be a prodrug of an inverse agonist of an opioid receptor. Alternatively, the API may be a prodrug of a species that may act as either an antagonist or an inverse agonist of an opioid receptor. The antagonist or inverse agonist of an opioid receptor may act on any one or more than one of the classes of opioid receptor, e.g. the μ-opioid receptor (MOR), the κ-opioid receptor (KOR), the δ-opioid receptor (DOR), the nociceptin receptor (NOR) and/or the ζ-opioid receptor (ZOR). Typical assays for determining whether a compound acts as an antagonist and/or an inverse agonist of an opioid receptor include: ligand displacement assays on isolated receptors in membrane preparations (e.g. by measuring the levels of receptor activity when both the test compound and morphine are present in varying concentrations); and assays that measure receptor behaviour after binding in whole cells (e.g. the assays described in reference [1], the contents of which are herein incorporated by reference in their entirety). The term "prodrug" of an antagonist or inverse agonist of an opioid receptor, as used herein, refers to any compound or pharmaceutically acceptable salt thereof which, after administration to the human body, may be metabolised in vivo to a compound which acts as an antagonist or inverse agonist of an opioid receptor. Typical prodrugs include acyl, ester and carbamyl derivatives of the compound which acts as an antagonist or inverse agonist of an opioid receptor.

Typically, the API is naloxone or naltrexone, or a pharmaceutically acceptable salt or prodrug thereof. Preferably, the API is naloxone or a pharmaceutically acceptable salt or prodrug thereof. More preferably, the API is naloxone, a 3-O-acyl derivative of naloxone, a 3-O-ester derivative of naloxone, a 3-O-carbamyl derivative of naloxone, or a pharmaceutically acceptable salt of any of the foregoing. Even more preferably, the API is naloxone or a pharmaceutically acceptable salt of naloxone. Still more preferably, the API is naloxone. Alternatively, the API may be a pharmaceutically acceptable salt of naloxone. The API may be the free base form of naloxone. The API may be a pharmaceutically acceptable polymorph, co-crystal, hydrate or solvate of naloxone or a pharmaceutically acceptable salt thereof.

Typically, the API is (−)-naloxone or a pharmaceutically acceptable salt thereof. In that case, (−)-naloxone or the pharmaceutically acceptable salt thereof is present in a therapeutically effective amount in the film. Typically, the API is (−)-naloxone. Alternatively, the API may be a pharmaceutically acceptable salt of (−)-naloxone. The API may be the free base form of (−)-naloxone. The API may be a pharmaceutically acceptable polymorph, co-crystal, hydrate or solvate of (−)-naloxone or a pharmaceutically acceptable salt thereof.

Alternatively, the API is (+)-naloxone or a pharmaceutically acceptable salt thereof. In that case, (+)-naloxone or the pharmaceutically acceptable salt thereof is present in a therapeutically effective amount in the film. Typically, the API is (+)-naloxone. Alternatively, the API may be a pharmaceutically acceptable salt of (+)-naloxone. The API may be the free base form of (+)-naloxone. The API may be a pharmaceutically acceptable polymorph, co-crystal, hydrate or solvate of (+)-naloxone or a pharmaceutically acceptable salt thereof.

Alternatively, the API is a mixture of (−)-naloxone and (+)-naloxone or a mixture of pharmaceutically acceptable salts thereof. In that case, (−)-naloxone and (+)-naloxone, or the pharmaceutically acceptable salts thereof, are present in a therapeutically effective amount in the film. Typically, the API is a mixture of (−)-naloxone and (+)-naloxone. Alternatively, the API may be a mixture of a pharmaceutically acceptable salt of (−)-naloxone and a pharmaceutically acceptable salt of (+)-naloxone. The API may be a mixture of the free base form of (−)-naloxone and the free base form of (+)-naloxone. The API may be a mixture of a pharmaceutically acceptable polymorph, co-crystal, hydrate or solvate of (−)-naloxone or a pharmaceutically acceptable salt thereof, and a pharmaceutically acceptable polymorph, co-crystal, hydrate or solvate of (+)-naloxone or a pharmaceutically acceptable salt thereof. Any of the foregoing mixtures may be a racemic mixture. Alternatively, any of the foregoing mixtures may contain an excess of (−)-naloxone or a pharmaceutically acceptable salt thereof over (+)-naloxone or a pharmaceutically acceptable salt thereof. Alternatively, any of the foregoing mixtures may contain an excess of (+)-naloxone or a pharmaceutically acceptable salt thereof over (−)-naloxone or a pharmaceutically acceptable salt thereof. Preferably, the foregoing mixtures contain an excess of (−)-naloxone or a pharmaceutically acceptable salt thereof over (+)-naloxone or a pharmaceutically acceptable salt thereof.

Most preferably, the API is (−)-naloxone or a pharmaceutically acceptable salt thereof. The API may preferably be the free base form of (−)-naloxone.

The structures of the enantiomers of naloxone are provided in Formulae (II) and (III) below.

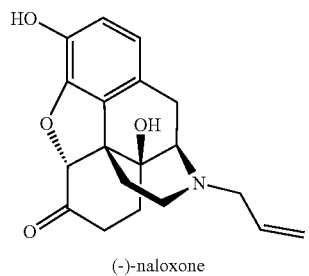

Formula (II)

(−)-naloxone

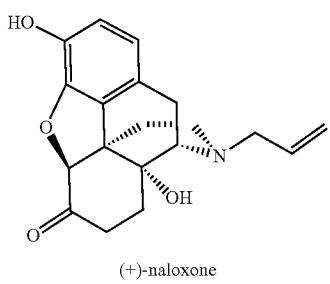

Formula (III)

(+)-naloxone

As defined herein, the term "naloxone" refers to the form of naloxone in which the naloxone molecules are present in neutral (i.e. unionized) form. The term "pharmaceutically acceptable salt of naloxone" refers to any salt of naloxone in which the tertiary amine group of naloxone is protonated, or in which one or both of the hydroxyl groups in naloxone are deprotonated. Preferably, the term "pharmaceutically acceptable salt of naloxone" refers to any salt of naloxone in which the tertiary amine group is protonated. The term "free base form of naloxone" refers to any form of naloxone in which the tertiary amine group is uncharged, i.e. in which naloxone can act as a base via the tertiary nitrogen atom. The term "free base form of naloxone" therefore encompasses both (i) naloxone molecules that are present in neutral (i.e. unionized) form, and (ii) any salt of naloxone in which one or both of the hydroxyl groups in naloxone are deprotonated and in which the tertiary amine group remains unprotonated. Typically, the term "free base form of naloxone" refers to naloxone molecules that are present in neutral (i.e. unionized) form.

Typically, the pharmaceutically acceptable salt of naloxone is selected from the group consisting of succinate, tartrate, citrate, fumarate, malonate, maleate, adipate, dimesylate, sulfate, benzenesulfonate, hydrochloride, and phosphate salts of naloxone. Preferred salt forms of naloxone include dicarboxylic acid salts, hydrochloric acid salts, phosphoric acid salts, sulfuric acid salts or benzenesulfonic acid salts of naloxone. Most preferably, the pharmaceutically acceptable salt of naloxone is the hydrochloric acid salt of naloxone.

Typically, the pharmaceutically acceptable salt of (−)-naloxone is selected from the group consisting of succinate, tartrate, citrate, fumarate, malonate, maleate, adipate, dimesylate, sulfate, benzenesulfonate, hydrochloride, and phosphate salts of (−)-naloxone. Preferred salt forms of (−)-naloxone include dicarboxylic acid salts, hydrochloric acid salts, phosphoric acid salts, sulfuric acid salts or benzenesulfonic acid salts of (−)-naloxone. Most preferably, the pharmaceutically acceptable salt of (−)-naloxone is the hydrochloric acid salt of naloxone.

Typically, the pharmaceutically acceptable polymorph, co-crystal, hydrate or solvate of naloxone or a pharmaceutically acceptable salt thereof is a pharmaceutically acceptable hydrate of naloxone or a pharmaceutically acceptable salt thereof. The pharmaceutically acceptable hydrate of naloxone may be a pharmaceutically acceptable salt of the free base form of naloxone. Preferred hydrate forms of naloxone or a pharmaceutically acceptable salt thereof include monohydrates and dihydrates of naloxone or a pharmaceutically acceptable salt thereof. More preferably, the hydrate form of naloxone or a pharmaceutically acceptable salt thereof is a dihydrate of naloxone or a pharmaceutically acceptable salt thereof. The hydrate form of naloxone or a pharmaceutically acceptable salt thereof may be a dihydrate of the free base form of naloxone. Even more preferably, the hydrate form of naloxone or a pharmaceutically acceptable salt thereof is a dihydrate of a pharmaceutically acceptable salt of naloxone. Most preferably, the hydrate form of naloxone or a pharmaceutically acceptable salt thereof is a dihydrate of naloxone hydrochloride.

Typically, the pharmaceutically acceptable polymorph, co-crystal, hydrate or solvate of (−)-naloxone or a pharmaceutically acceptable salt thereof is a pharmaceutically acceptable hydrate of (−)-naloxone or a pharmaceutically acceptable salt thereof. Preferred hydrate forms of (−)-naloxone or a pharmaceutically acceptable salt thereof include monohydrates and dihydrates of (−)-naloxone or a pharmaceutically acceptable salt thereof. More preferably, the hydrate form of (−)-naloxone or a pharmaceutically acceptable salt thereof is a dihydrate of (−)-naloxone or a pharmaceutically acceptable salt thereof. Even more preferably, the hydrate form of (−)-naloxone or a pharmaceutically acceptable salt thereof is a dihydrate of a pharmaceutically acceptable salt of (−)-naloxone. Most preferably, the hydrate form of (−)-naloxone or a pharmaceutically acceptable salt thereof is a dihydrate of (−)-naloxone hydrochloride.

The API may be present within the film in varying amounts. Typically, the film comprises from 0.001% to 75% by weight of the API, preferably from 0.01% to 60% by weight of the API, more preferably from 0.15% to 50% by weight of the API, still more preferably from 0.2% to 45% by weight of the API and most preferably from 0.25% to 40% by weight of the API.

Typically, the antagonist of an opioid receptor, inverse agonist of an opioid receptor, or a prodrug thereof is the only API present in the film. However, the film may alternatively comprise one or more further active pharmaceutical ingredients in addition to the antagonist of an opioid receptor, inverse agonist of an opioid receptor, or a prodrug thereof. In this case, the film typically comprises an opioid or a pharmaceutically acceptable salt thereof, in addition to naloxone or a pharmaceutically acceptable salt thereof. Preferably, the opioid is selected from the group consisting of morphine, dimorphine, fentanyl, tramadol, 2,4-dinitrophenylmorphine, 6-MDDM, chlornaltrexamine, desomorphine, dihydromorphine, hydromorphinol, methyldesorphine, N-phenethylnormorphine, RAM-378, acetylpropionylmorphine, dihydroheroin, dibenzoylmorphine, dipropanoylmorphine, heroin, nicomorphine, codeine, 6-MAC, benzylmorphine, codeine methylbromide, dihydroheterocodeine, ethylmorphine, heterocodeine, pholcodine, myrophine, 14-cinnamoyloxycodeinone, 14-ethoxymetopon, 14-methoxymetopon, PPOM, 7-spiroindanyloxymorphone, acetylmorphone, codeinone, conorphone, codoxime, thebacon, hydrocodone, hydromorphone, metopon, morphinone, N-phenethyl-14-ethoxymetopon, oxycodone, oxymorphone, pentamorphone, semorphone, chloromorphide, 14-hydroxydihydrocodeine, acetyldihydrocodeine, dihydrocodeine, nalbuphine, nicocodeine, nicodicodeine, oxymorphazone, 1-iodomorphine, M6G, 6-MAM, norcodeine, normorphine, morphine-N-oxide, cyclorphan, DXA, levorphanol, levophenacylmorphan, levomethorphan, norlevorphanol, oxilorphan, phenomorphan, furethylnorlevorphanol, xorphanol, butorphanol, cyprodime, drotebanol, 7-PET, acetorphine, BU-48, buprenorphine, cyprenorphine, dihydroetorphine, etorphine, norbuprenorphine, and combinations thereof. More preferably, the opioid is buprenorphine.

Preferably, the film comprises from 25% to 99% by weight of the alginate salt of a monovalent cation or the mixture of alginate salts containing at least one alginate salt of a monovalent cation, from 0% to 20% by weight of water, and from 0.001% to 75% by weight of the API. More preferably, the film comprises from 29% to 93% by weight of the alginate salt of a monovalent cation or the mixture of alginate salts containing at least one alginate salt of a monovalent cation, from 5% to 15% by weight of water, and from 0.15% to 50% by weight of the API. Even more preferably, the film comprises from 30% to 91% by weight of the alginate salt of a monovalent cation or the mixture of alginate salts containing at least one alginate salt of a monovalent cation, from 9% to 11% by weight of water, and from 0.2% to 45% by weight of the API.

A film according to the present invention may optionally further comprise other components in addition to the API, water and the film-forming agent. Typically, a film according to the present invention further comprises one or more of the following:
(i) at least one pharmaceutically acceptable solvent;
(ii) at least one buffering component;
(iii) at least one excipient;
(iv) at least one acidifying agent or basifying agent;
(v) at least one permeation enhancer;
(vi) a self-nanoemulsifying drug delivery system (SNEDDS); and
(vii) at least one preservative.

The film may additionally comprise any pharmaceutically acceptable solvent. Such a solvent may be a non-aqueous solvent, or a combination of water and a non-aqueous solvent. Examples of non-aqueous solvents should be non-toxic and include, but are not limited to, ethanol, acetone, benzyl alcohol, diethylene glycol monoethyl ether, glycerine, hexylene glycol, isopropyl alcohol, polyethylene glycols, methoxypolyethylene glycols, diethyl sebacate, dimethyl isosorbide, propylene carbonate, and dimethyl sulfoxide.

The film may additionally comprise any suitable buffering component. A "buffering component", as defined herein, refers to any chemical entity, which when dissolved in solution, enables said solution to resist changes in its pH following the subsequent addition of either an acid or a base. A suitable buffering component for use in the film of the present invention would be a buffering component which is an effective buffer within a pH range of from 3.0 to 12.0. Typically, said buffering component is an effective buffer within a pH range of from 3.0 to 7.0, preferably within a pH range of from 3.5 to 5.5, more preferably within a pH range of from 3.5 to 4.5, even more preferably within a pH range of from 3.8 to 4.5, yet more preferably within a pH range of from 3.8 to 4.2, and still more preferably at a pH of about 4.0. In that case, if the API is naloxone, the naloxone is present within the buccal film in a salt form, e.g. as naloxone hydrochloride. Alternatively, said buffering component is an effective buffer within a pH range of from 7.0 to 11.0, preferably within a pH range of from 7.84 to 10.07, more preferably within a pH range of from 8.0 to 10.0, even more preferably within a pH range of from 8.5 to 9.5 and still more preferably at a pH of about 9.0. In the case where the pH is greater than 7.84, if the API is naloxone, the naloxone is present within the buccal film in its free base form. In the case where the pH is between 7.84 and 10.07, the naloxone is present within the buccal film in its neutral form. Examples of suitable buffering components include, but are not limited to: phosphates, sulfates, citrates and acetates. The buffer may be a salt of a monovalent cation, such as sodium, potassium or ammonium salts. Particularly preferred buffering components include citric acid and sodium dihydrogen phosphate.

The film may comprise from 0.1% to 10% by weight of the buffering component, typically 0.2% to 8% by weight, typically from 0.3% to 6% by weight, typically from 0.5% to 5% by weight. Alternatively, the film may not additionally comprise a buffering component.

The film may additionally comprise any suitable excipient, such as one or more fillers or plasticizers. The film may comprise both a plasticizer and a filler. Alternatively, the film may comprise just one of a plasticizer or a filler. It is preferred that the film comprises a plasticizer. Under some circumstances it may be desirable that the film does not comprise a filler. It is particularly preferred that the film comprises a plasticizer but does not comprise a filler. The film may additionally include a taste-masking agent or a flavouring agent. The taste-masking agent may be a sweetener. The film may additionally include a colourant.

The plasticizer, when present, may be selected from the group consisting of polyethylene glycol, glycerol, sorbitol, xylitol, and a combination thereof. Typically, the film comprises a plasticizer which is selected from the group consisting of glycerol, sorbitol, xylitol, and a combination thereof. Preferably, the film comprises a plasticizer which is selected from the group consisting of glycerol, sorbitol, and a combination thereof. More preferably, the film comprises both glycerol and sorbitol as plasticizers. Alternatively, the film may comprise glycerol, sorbitol and xylitol as plasticizers. The film may comprise from 0% to 40% by weight of each plasticizer present, preferably from 1% to 35% by weight of each plasticizer, more preferably from 2% to 30% by weight of each plasticizer, and most preferably from 3% to 25% by weight of each plasticizer.

The filler, when present, may be e.g. microcrystalline cellulose or titanium dioxide. A suitable amount of filler may be from 0% to 20% by weight, e.g. from 5% to 10% by weight, of the total pharmaceutical composition.

Titanium dioxide may be present in a film according to the present invention either as a filler or as a colourant. Typically, if titanium dioxide is present, the titanium dioxide acts as both a filler and a colourant.

The film may additionally comprise an acidifying agent or a basifying agent. An "acidifying agent", as defined herein, refers to a chemical compound that alone or in combination with other compounds can be used to acidify a pharmaceutical composition. A "basifying agent", as defined herein, refers to a chemical compound that alone or in combination with other compounds can be used to basify a pharmaceutical composition.

Typically, the film comprises an basifying agent which is a base having a $pK_a$ of 7.84 or greater, more preferably having a $pK_a$ of 9.0 or greater, and most preferably having a $pK_a$ of 10.07 or greater. Typically, the basifying agent is an alkali. Examples of suitable basifying agents include, but are not limited to: sodium hydroxide, lithium hydroxide, potassium hydroxide, magnesium hydroxide, and calcium hydroxide. Preferably, in this case the film comprises an basifying agent which is sodium hydroxide. Alternatively, the film comprises an acidifying agent which is an acid having a $pK_a$ of 10.07 or less, more preferably having a $pK_a$ of 7.0 or less, and most preferably having a $pK_a$ of 5.0 or less. Examples of suitable acidifying agents include, but are not limited to: acetic acid, dehydro acetic acid, ascorbic acid, benzoic acid, boric acid, citric acid, edetic acid, hydrochloric acid, isostearic acid, lactic acid, nitric acid, oleic acid, phosphoric acid, sorbic acid, stearic acid, sulfuric acid, tartaric acid, and undecylenic acid. Preferably, in this case the film comprises an acidifying agent which is phosphoric acid.

A film according to the present invention is produced via the drying of a film-forming solution (vide infra). Typically, a sufficient amount of acidifying agent or basifying agent is added to adjust the pH of the film-forming solution (before this is dried to form the film) to a pH of from 3.0 to 12.0. Typically, a sufficient amount of acidifying or basifying agent is added to adjust the pH of the film-forming solution (before this is dried to form the film) to a pH of from 3.0 to 7.0, preferably a pH of from 3.5 to 5.5, more preferably a pH of from 3.5 to 4.5, even more preferably within a pH range of from 3.8 to 4.5, yet more preferably within a pH range of from 3.8 to 4.2, and still more preferably a pH of about 4.0. Alternatively, a sufficient amount of acidifying or basifying agent is added to adjust the pH of the film-forming solution (before this is dried to form the film) to a pH of from 7.0 to 11.0, preferably a pH of from 7.84 to 10.07, more preferably a pH of from 8.0 to 10.0, even more preferably a pH of from 8.5 to 9.5, and still more preferably a pH of about 9.0.

The film may additionally comprise any suitable permeation enhancer. A "permeation enhancer", as defined herein, refers to a chemical compound that alone or in combination with other compounds can be used to aid the uptake of a further substance across an epithelium or other biological membrane. In particular, the term "permeation enhancer" is used herein to refer to a chemical compound that alone or in combination with other compounds can be used to aid the uptake of a further substance across the buccal mucosa. Permeation enhancers can typically be divided into two different categories, paracellular (para) or transcellular (trans) permeability enhancers, according to their mechanism of action. Paracellular permeation enhancers are those which aid the uptake of a further substance through the intercellular space between the cells in an epithelium or other biological membrane. Transcellular permeation enhancers are those which aid the uptake of a further substance through the cells in an epithelium or other biological membrane, wherein the further substance passes through both the apical and basolateral cell membranes in the epithelium or other biological membrane.

Typically, the film may comprise one or more paracellular permeation enhancers. Alternatively, the film may comprise one or more transcellular permeation enhancers. Alternatively, the film may comprise at least one paracellular permeation enhancer and at least one transcellular permeation enhancer.

Typically, the permeation enhancer is one or more compounds selected from the group consisting of: non-ionic, cationic, anionic or zwitterionic surfactants (e.g. caprylocaproyl polyoxyl-8 glyceride, sodium lauryl sulfate, cetyltrimethyl ammonium bromide, decyldimethyl ammonio propane sulfonate); bile salts (e.g. sodium deoxycholate); fatty acids (e.g. hexanoic acid, heptanoic acid, oleic acid); fatty amines; fatty ureas; fatty acid esters (e.g. methyl laurate, methyl palmitate); substituted or unsubstituted nitrogen-containing heterocyclic compounds (e.g. methyl pyrrolidone, methyl piperazine, azone); terpenes (e.g. limonene, fenchone, menthone, cineole); sulfoxides (e.g. dimethylsulfoxide, DMSO); ethylenediaminetetraacetic acid (EDTA); and combinations thereof. Preferably, the permeation enhancer is selected from the group consisting of EDTA, oleic acid, and combinations thereof.

Typically, the film may comprise EDTA. Without wishing to be bound by any particular theory, EDTA is believed to act as a paracellular permeation enhancer by transiently affecting tight junctions interconnecting membrane cells, and subsequently increasing paracellular or pore transport. EDTA is also believed to act as a transcellular permeation enhancer by interaction with phospholipid headgroups and increasing membrane fluidity [5]. Alternatively, the film may comprise oleic acid. Without wishing to be bound by any particular theory, oleic acid is believed to act as a transcellular permeation enhancer by interacting with the polar head groups of phospholipids in or on cell membranes, and increasing cell membrane flexibility, thereby promoting transcellular drug permeability. Oleic acid has been shown to demonstrate enhanced permeability with porcine buccal epithelium at a concentration of 1-10% [6].

The film may additionally comprise a self-nanoemulsifying drug delivery system (SNEDDS) or resulting emulsion thereof. Self-nanoemulsifying drug delivery systems are nanoemulsion preconcentrates or anhydrous forms of nanoemulsion. These systems are typically anhydrous isotropic mixtures of oil (e.g. tri-, di- or mono-glycerides or mixtures thereof) and at least one surfactant (e.g. Span, Tween), which, when introduced into aqueous phase under conditions of gentle agitation, spontaneously form an oil-in-water (O/W) nanoemulsion, typically with a globule size less than 200 nm [7]. SNEDDS may also contain coemulsifier or cosurfactant and/or solubilizer in order to facilitate nanoemulsification or improve the drug incorporation into the SNEDDS. Typically, the SNEDDS components is selected from the group consisting of: a mixture of Tween with one or more glycerides and a hydrophilic cosolvent; a mixture of Tween with a low HLB cosurfactant and a hydrophilic cosolvent; a mixture of a polyethyleneglycol (PEG), Labrasol and Chremophore EL; a mixture of polyethyleneglycol (PEG), Labrasol and Kolliphore EL; and a mixture of polyethyleneglycol (PEG), Labrasol, Chremophore EL and Chremophore RH40. The PEG may be any suitable polyethyleneglycol such as PEG with an average molecular weight of from 100 to >1000 Da, preferably from 200 to 800 Da, more preferably from 300 to 600 Da, and most preferably about 400. The term "glyceride", as defined herein, refers to any ester formed between glycerol and one or more fatty acids. The term "glyceride" may be used interchangeably with the term "acylglycerol". Typically, the glyceride is a monoglyceride, a diglyceride or a triglyceride. Preferably, the glyceride is a triglyceride. Typically, the glyceride is a simple glyceride. The term "simple glyceride" refers to a diglyceride in which the two fatty acids are the same as one another, or a triglyceride in which the three fatty acids are the same as one another. Alternatively, the glyceride is a mixed glyceride. The term "mixed glyceride" refers to a diglyceride in which the two fatty acids are different one another, or a triglyceride in which either one of the three fatty acids is different to the other two, or all three of the fatty acids are different to one another. Therefore, the glyceride is typically a monoglyceride, a simple diglyceride, a simple triglyceride, a mixed diglyceride, or a mixed triglyceride. Preferably, the glyceride is a simple triglyceride or a mixed triglyceride. A "hydrophilic cosolvent", as defined herein, is any solvent that is miscible with water. Examples of suitable hydrophilic cosolvents include, but are not limited to: glycerol, ethanol, 2-(2-ethoxyethoxyethanol), PEG-400 and propylene glycol. The term "low HLB cosurfactant", as defined herein, refers to any lipid falling within class IIIA, IIIB or IV of the lipid formulation classification system described by C. W. Pouton [8], the contents of which are herein incorporated by reference in their entirety.

Typically, the film may additionally comprise any suitable preservative. A "preservative", as defined herein, may refer to: (i) a chelating agent; (ii) an antioxidant; or (iii) an antimicrobial agent.

Preferably, the preservative is any suitable chelating agent. A "chelating agent", as defined herein, refers to a chemical compound that is a multidentate ligand that is capable of forming two or more separate bonds to a single central atom, typically a metal ion. Examples of suitable chelating agents include, but are not limited to: ethylenediaminetetraacetic acid (EDTA), ethylene glycol-bis(β-aminoethyl ether)-N,N,N',N'-tetraacetic acid (EGTA), 1,2-bis(ortho-aminophenoxy)ethane-N,N,N',N'-tetraacetic acid (BAPTA), citric acid, phosphonic acid, glutamic acid, histidine, malate, and derivatives thereof. Preferably, the chelating agent, if present, is ethylenediaminetetraacetic acid (EDTA). The film may comprise from 0.001% to 4% by weight of each chelating agent present. Preferably, the film may comprise from 0.001% to 0.1% by weight of each chelating agent present.

Alternatively, the preservative may be any suitable antioxidant. An "antioxidant", as defined herein, is any compound that inhibits the oxidation of other chemical species. Examples of suitable antioxidants include, but are not limited to: ascorbic acid; citric acid; sodium bisulfite; sodium metabisulfite; and butyl hydroxytoluene. Preferably, the antioxidant, if present, is ascorbic acid. Alternatively, preferably the antioxidant, if present, is sodium bisulfite. Alternatively, preferably the film may comprise both ascorbic acid and sodium bisulfite as antioxidants. The film may comprise from 0.001% to 4% by weight of each antioxidant present. Preferably, the film may comprise from 0.001% to 0.1% by weight of each antioxidant present.

Alternatively, the preservative may be any suitable antimicrobial agent. An "antimicrobial agent", as defined herein, is any compound that kills microorganisms or prevents their growth. Examples of suitable antimicrobial agents include, but are not limited to: benzyl alcohol; benzalkonium chloride; benzoic acid; methyl-, ethyl- or propyl-paraben; and quaternary ammonium compounds. The film may comprise from 0.001% to 4% by weight of each antimicrobial agent present. Preferably, the film may comprise from 0.001% to 0.1% by weight of each antimicrobial agent present.

EDTA may therefore be present in a film according to the present invention either as a permeation enhancer or as a chelating agent. Typically, if EDTA is present, the EDTA acts as both a permeation enhancer and a chelating agent. Alternatively, if EDTA is present, the EDTA may act only as a permeation enhancer. Alternatively, if EDTA is present, the EDTA may act only as a chelating agent.

Typically, the film may additionally comprise at least one excipient, at least one basifying agent or acidifying agent, optionally at least one permeation enhancer, optionally at least one preservative, optionally at least one pharmaceutically acceptable solvent, optionally at least one buffering component, and optionally a SNEDDS. For example, the film may comprise at least one excipient, at least one basifying agent or acidifying agent, at least one permeation enhancer, optionally at least one preservative, and optionally at least one buffering component. Preferably, the film may comprise glycerol, sorbitol, at least one basifying agent or acidifying agent, at least one permeation enhancer, optionally, at least one preservative, and, optionally, at least one buffering component. More preferably, the film may comprise glycerol, sorbitol, at least one basifying agent or acidifying agent, a permeation enhancer selected from the group consisting of EDTA, oleic acid and combinations thereof, optionally, at least one chelating agent, and, optionally, at least one buffering component. Even more preferably, the film may comprise: glycerol; sorbitol; sodium hydroxide; a permeation enhancer selected from the group consisting of EDTA, oleic acid and combinations thereof; and, optionally, citric acid or sodium dihydrogen phosphate. Alternatively, even more preferably, the film may comprise: glycerol; sorbitol; phosphoric acid; a permeation enhancer selected from the group consisting of EDTA, oleic acid and combinations thereof; and, optionally, citric acid or sodium dihydrogen phosphate. Alternatively, the film may comprise at least one excipient, at least one basifying agent or acidifying agent, at least one permeation enhancer, and optionally a SNEDDS. Preferably, the film may comprise glycerol, sorbitol, at least one basifying agent or acidifying agent, at least one permeation enhancer and, optionally, a SNEDDS. More preferably, the film may comprise glycerol, sorbitol, at least one basifying agent or acidifying agent, a permeation enhancer selected from the group consisting of EDTA, oleic acid and combinations thereof, and, optionally, a SNEDDS. Even more preferably, the film may comprise: glycerol; sorbitol; sodium hydroxide; a permeation enhancer selected from the group consisting of EDTA, oleic acid and combinations thereof; and, optionally, a SNEDDS selected from the group consisting of a mixture of Tween with one or more glycerides and a hydrophilic cosolvent, a mixture of Tween with a low HLB cosurfactant and a hydrophilic cosolvent, and a mixture of PEG 400, Labrasol and Kolliphore EL. Alternatively, even more preferably, the film may comprise: glycerol; sorbitol; phosphoric acid; a permeation enhancer selected from the group consisting of EDTA, oleic acid and combinations thereof; and, optionally, a SNEDDS selected from the group consisting of a mixture of Tween with one or more glycerides and a hydrophilic cosolvent, a mixture of Tween with a low HLB cosurfactant and a hydrophilic cosolvent, and a mixture of PEG 400, Labrasol and Kolliphore EL. Alternatively, the film may comprise at least one excipient and at least one basifying agent or acidifying agent. Preferably, the film may comprise glycerol, sorbitol and at least one basifying agent or acidifying agent. More preferably, the film may comprise glycerol, sorbitol, and sodium hydroxide. Alternatively, more preferably the film may comprise glycerol, sorbitol, and phosphoric acid.

Preferably, the film according to the present invention comprises from 25% to 99% by weight of the alginate salt of a monovalent cation or the mixture of alginate salts containing at least one alginate salt of a monovalent cation, from 0% to 20% by weight of water, from 0.001% to 75% by weight of the API, from 0% to 40% by weight of glycerol, from 0% to 40% by weight of sorbitol, a basifying agent or an acidifying agent, optionally from 0.01% to 5% by weight of a permeation enhancer, optionally from 0.1% to 10% by weight of a SNEDDS, optionally from 0.001% to 4% by weight of an antioxidant, and optionally from 0.001% to 4% by weight of a chelating agent. More preferably, the film according to the present invention comprises from 30% to 91% by weight of the alginate salt of a monovalent cation or the mixture of alginate salts containing at least one alginate salt of a monovalent cation, from 9% to 11% by weight of water, and from 0.2% to 45% by weight of the API, from 10% to 20% by weight of glycerol, from 10% to 20% by weight of sorbitol, a basifying agent or an acidifying agent, from 0.001% to 4% by weight of a chelating agent, optionally from 0.01% to 5% by weight of a permeation enhancer, and optionally from 0.1% to 10% by weight of a SNEDDS.

Alternatively, the film according to the present invention consists of from 25% to 99% by weight of the alginate salt of a monovalent cation or the mixture of alginate salts containing at least one alginate salt of a monovalent cation, from 0% to 20% by weight of water, from 0.001% to 75% by weight of the API, from 0% to 40% by weight of glycerol, from 0% to 40% by weight of sorbitol, a basifying agent or an acidifying agent, optionally from 0.01% to 5% by weight of a permeation enhancer, and optionally from 0.1% to 10% by weight of a SNEDDS, optionally from 0.001% to 4% by weight of an antioxidant, and optionally from 0.001% to 4% by weight of a chelating agent. Alternatively, the film according to the present invention consists of from 30% to 91% by weight of the alginate salt of a monovalent cation or the mixture of alginate salts containing at least one alginate salt of a monovalent cation, from 9% to 11% by weight of water, and from 0.2% to 45% by weight of the API, from 10% to 20% by weight of glycerol, from 10% to 20% by weight of sorbitol, a basifying agent or an acidifying agent, from 0.001% to 4% by weight of a chelating agent, optionally from 0.01% to 5% by weight of a permeation enhancer, and optionally from 0.1% to 10% by weight of a SNEDDS.

It is desirable that a film according to the present invention contains less than 3.5% by weight of undesirable impurities after 12 weeks of storage, e.g. at 25° C. at 60% relative humidity in a PET-lined aluminium pouch.

A film according to the invention preferably has a thickness before drying of 200 to 2000 µm, more preferably from 300 to 1750 µm, even more preferably from 400 to 1500 µm, and most preferably about 1000 µm.

A film according to the invention preferably has a surface area on each of its two largest faces of from 0.1 to 20 $cm^2$, more preferably from 0.5 to 15 $cm^2$, even more preferably from 1 to 10 $cm^2$ and most preferably from 2 to 6 $cm^2$. Preferably, the surface area of each of the two largest faces of the film is about 3 $cm^2$.

A film according to the invention preferably comprises the API and each of components (i)-(vii) described above, if present, in a single layer. Thus, typically, a film according to the present invention does not comprise two or more distinct layers. Typically, the components in a film according to the invention are distributed in a uniform, or substantially uniform, way throughout a single layer.

The skilled person, having regard for the desired time of dissolution for a given application, will be able to select a suitable film thickness and surface area by simply preparing films of a range of different thicknesses and surface areas and testing the resultant films to measure the dissolution time.

The mechanical properties of a film according to the invention are very satisfactory. In particular, the film is flexible (i.e. it permits bending and folding without breaking), and has a high tensile strength. Importantly, the film of the present invention is not a gel, since the alginate polymer strands are not cross-linked with one another. The film of the invention is bioadhesive; that is to say that the film comprises a natural polymeric material (alginate) which can act as an adhesive. The film is adhesive to moist surfaces, such as mucosa. In particular, the film is adhesive to mucosa of the oral cavity, such as mucosa in the buccal, labial, sublingual, gingival or lip areas, the soft palate and the hard palate.

The film according to the invention may be provided with printed text matter or printed images thereon, e.g. a brand name, a trade mark, a dosage indication or a symbol.

Administration and Uses of the Films in Treatment

In general, films of the present invention are administered to a human patients so as to deliver to the patient a therapeutically effective amount of the active pharmaceutical ingredient (API), preferably (−)-naloxone or a pharmaceutically acceptable salt thereof, contained therein.

As used herein, the term "therapeutically effective amount" refers to an amount of the API which is sufficient to reduce or ameliorate the severity, duration, progression, or onset of a disorder being treated, prevent the advancement of a disorder being treated, cause the regression of, prevent the recurrence, development, onset or progression of a symptom associated with a disorder being treated, or enhance or improve the prophylactic or therapeutic effect(s) of another therapy. The precise amount of API administered to a patient will depend on the type and severity of the disease or condition and on the characteristics of the patient, such as general health, age, sex, body weight and tolerance to drugs. It will also depend on the degree, severity and type of the disorder being treated. The skilled artisan will be able to determine appropriate dosages depending on these and other factors.

As used herein, the terms "treat", "treatment" and "treating" refer to the reduction or amelioration of the progression, severity and/or duration of a disorder being treated, or the amelioration of one or more symptoms (preferably, one or more discernible symptoms) of a disorder being treated resulting from the administration of a film according to the invention to a patient.

Typically, a film according to the present invention is provided for use in the treatment of a human patient. Preferably, the film according to the invention is provided for use in the treatment of the effects of acute opioid overdose, or for use in reducing the risk of opioid abuse. More preferably, the film according to the invention is provided for use in the treatment of the effects of acute opioid overdose.

The term "opioid" refers to any substance, natural or synthetic, that acts on the opioid receptor. Opioid receptors are G-protein coupled receptors that act through a number of pathways to suppress pain perception.

Examples of opioids include morphine, dimorphine, fentanyl, tramadol, 2,4-dinitrophenylmorphine, 6-MDDM, chlornaltrexamine, desomorphine, dihydromorphine, hydromorphinol, methyldesorphine, N-phenethylnormorphine, RAM-378, acetylpropionylmorphine, dihydroheroin, dibenzoylmorphine, dipropanoylmorphine, heroin, nicomorphine, codeine, 6-MAC, benzylmorphine, codeine methylbromide, dihydroheterocodeine, ethylmorphine, heterocodeine, pholcodine, myrophine, 14-cinnamoyloxycodeinone, 14-ethoxymetopon, 14-methoxymetopon, PPOM, 7-spiroindanyloxymorphone, acetylmorphone, codeinone, conorphone, codoxime, thebacon, hydrocodone, hydromorphone, metopon, morphinone, N-phenethyl-14-ethoxymetopon, oxycodone, oxymorphone, pentamorphone, semorphone, chloromorphide, 14-hydroxydihydrocodeine, acetyldihydrocodeine, dihydrocodeine, nalbuphine, nicocodeine, nicodicodeine, oxymorphazone, 1-iodomorphine, M6G, 6-MAM, norcodeine, normorphine, morphine-N-oxide, cyclorphan, DXA, levorphanol, levophenacylmorphan, levomethorphan, norlevorphanol, oxilorphan, phenomorphan, furethylnorlevorphanol, xorphanol, butorphanol, cyprodime, drotebanol, 7-PET, acetorphine, BU-48, buprenorphine, cyprenorphine, dihydroetorphine, etorphine, norbuprenorphine, and combinations thereof.

The present invention provides a film according to the invention for use in the treatment of the effects of an acute opioid overdose. The effects of an acute opioid overdose in a patient may be severe. The effects of acute opioid overdose include respiratory depression, decreased consciousness, reduction in pupil size ("pinpoint pupils"), seizures, muscle spasms, hypoxia, hypoxia-induced injury including brain damage, spinal cord injury, lack of mobility and paralysis. In the most severe cases, the effects of acute opioid overdose can cause the patient to become comatose or can cause death of the patient. Typically, the effects of an acute opioid overdose include respiratory depression, decreased consciousness and/or a reduction in pupil size.

Therefore, the present invention provides a film according to the invention for use in the treatment of a condition or disease induced by an acute opioid overdose selected from the group consisting of respiratory depression, decreased consciousness, reduction in pupil size ("pinpoint pupils"), seizures, muscle spasms, hypoxia, hypoxia-induced injury including brain damage, spinal cord injury, lack of mobility and paralysis, and combinations thereof. Preferably, the film is for use in the treatment of a condition or disease induced by an acute opioid overdose selected from the group consisting of respiratory depression, decreased consciousness, reduction in pupil size, and combinations thereof.

Alternatively, the present invention provides a film according to the invention for use in the prevention of a condition or disease induced by an acute opioid overdose selected from the group consisting of respiratory depression, decreased consciousness, reduction in pupil size ("pinpoint pupils"), seizures, muscle spasms, hypoxia, hypoxia-induced injury including brain damage, spinal cord injury, lack of mobility and paralysis, and combinations thereof. Preferably, the film is for use in the prevention of a condition or disease induced by an acute opioid overdose selected from the group consisting of respiratory depression, decreased consciousness, reduction in pupil size, and combinations thereof.

An acute opioid overdose additionally associated with use of central nervous system (CNS) depressants such as alcohol, benzodiazepines, muscle relaxers, pain relievers, anti-convulsants, anxiolytics, psychoactive drugs, barbiturates can lead to a contraindicated condition. If the opioid overdose is additionally associated with use of a central nervous system depressant, the effects of the opioid overdose may be worsened and/or the chances of the patient making a recovery may be reduced.

Therefore, in an alternative embodiment of the invention, a film according to the invention is provided for use in the treatment of a condition or disease induced by an acute opioid overdose in combination with the effects of a CNS depressant, optionally wherein the CNS depressant is selected from the group consisting of alcohol, benzodiazepines, muscle relaxers, pain relievers, anti-convulsants, anxiolytics, psychoactive drugs, barbiturates, and combinations thereof.

In a further alternative embodiment of the invention, a film according to the invention is provided for use in the prevention of a condition or disease induced by an acute opioid overdose in combination with the effects of a CNS depressant, optionally wherein the CNS depressant is selected from the group consisting of alcohol, benzodiazepines, muscle relaxers, pain relievers, anti-convulsants, anxiolytics, psychoactive drugs, barbiturates, and combinations thereof.

Typically, the patient to be treated possesses an opioid dependency. Alternatively, the patient to be treated does not possess an opioid dependency. Typically, the patient to be treated is a frequent user of opioids or other narcotics. Alternatively, the patient may be a casual or infrequent user of narcotics. The patient may possess an alcohol dependency, or an addition to other CNS depressants such as a prescription medication. Typically, the patient to be treated is an adult. Alternatively, the patient to be treated may be a child. The patient to be treated may be an elderly patient.

The present invention also provides a film according to the invention for use in reducing the risk of opioid abuse. Herein, the term "opioid abuse" is used interchangeably with the term "opioid use disorder". The present invention therefore also provides a film according to the invention for use in reducing the risk of opioid use disorder.

Opioid abuse is a medical condition characterised by a pattern of opioid use that causes clinically significant impairment or distress. Opioid abuse often includes a strong desire to use opioids, increased tolerance to opioids, and withdrawal syndrome when opioids are abruptly discontinued. Addiction and dependence are components of opioid abuse and addiction represents the most severe form of the disorder. Opioid dependence can manifest as physical dependence, psychological dependence, or both.

Typically, when the film of the present invention is provided for use in reducing the effects of opioid abuse in a patient, the film is for use in reducing the desire of the patient to use opioids. The present invention also provides a film according to the invention for use in reducing the risk of opioid addiction, or the risk of opioid dependency, or both.

Typically, the film is administered to the oral cavity of the patient. The film is preferably applied to an oral mucosa in the buccal or labial or sublingual areas or to the soft palate. The film is typically applied by the patient themselves. Alternatively, the film is administered to the patient by another person, e.g. a medical practitioner, a nurse, a carer, a social worker, or a family member of the patient.

The film is bioadhesive and adheres to the surface of the oral cavity upon application. After application, the alginate film begins to dissolve, releasing the active pharmaceutical ingredient. Typically, the film fully dissolves in a time period of from 0.1 to 60 minutes or more after application to the mucosa of the oral cavity. Preferably, the film fully dissolves in a time period of from 0.5 to 30 minutes, more preferably from 1 to 20 minutes, still more preferably from 3 to 10 minutes, and most preferably from 3 to 5 minutes after application to the mucosa of the oral cavity.

Without wishing to be bound by any particular theory, it is believed that as the film dissolves within the oral cavity, the active pharmaceutical ingredient which is concomitantly released may enter the bloodstream by one or both of two different routes: (a) via absorption across the oral mucosa directly into the bloodstream (the "oral transmucosal route"); and (b) via swallowing into the stomach and subsequent absorption across the epithelium of the intestines into the bloodstream. When the API is (−)-naloxone or a pharmaceutically acceptable salt thereof, typically the peak plasma concentration of (−)-naloxone in a patient exceeds 1 ng/mL, which is the target threshold plasma concentration of (−)-naloxone for relief of the symptoms of acute opioid overdose in a patient. This peak plasma concentration may be achieved within 120 minutes from adhesion of the film to the mucosa of the oral cavity, preferably within 60 minutes from adhesion, more preferably within 45 minutes, even more preferably within 30 minutes or 20 minutes from adhesion, and most preferably within 10 minutes from adhesion.

Without wishing to be bound by any particular theory, where mucosal delivery is desired it is generally considered advantageous to ensure that the drug is primarily in an un-ionized form, as unionized drug species generally pass through cell membranes more easily than ionized species. Therefore, in one preferred embodiment of the invention, naloxone is formulated in an alginate based buccal film at a pH between its strongest acidic $pK_a$ (7.84) and strongest basic $pK_a$ (10.07), so that naloxone is un-ionized and suited for crossing the mucosa [9]. In that case, naloxone is preferably formulated in the film at a pH between 8.0 and 10.0, more preferably at a pH between 8.5 and 9.5, and most preferably at a pH of about 9.0. However, effective mucosal delivery of naloxone may also be achieved from an alginate based buccal film when naloxone is present in its ionized form. Naloxone is most stable in solution at a pH of about 4 in its ionized form, and naloxone nasal sprays available on the market are formulated at a pH of about 4 [10]. Therefore, in an alternative preferred embodiment of the present invention, naloxone is formulated in the film in its ionized form, typically at a pH between 3.0 and 5.0, preferably at a pH between 3.5 and 4.5, and more preferably at a pH of about 4.0.

Typically, a single film is applied to the patient, generally to the mucosa of the oral cavity, at a given time. However, in some cases it may be desirable to apply two films simultaneously to achieve the correct dose for an individual patient. When the API is (−)-naloxone, and it is being used to treat an acute opioid overdose, the recommended dosage for adults is between 0.1 and 25 mg (−)-naloxone per overdose event, more preferably between 0.5 and 10 mg naloxone per overdose event. When the API is (−)-naloxone, and it is being used to reduce the risk of opioid abuse, the recommended dosage for adults is between 0.01 and 2.5 mg (−)-naloxone per day, more preferably between 0.05 and 1.0 mg naloxone per day. In some cases it may be desirable to apply more than two films simultaneously to achieve the correct dose for an individual patient, for example, three, four, five, six, seven, eight, nine, ten or more.

The present invention also therefore provides a method of treating a condition in a human patient, wherein said method comprises administration of at least one film according to the invention to the oral cavity of the human patient, optionally wherein the condition to be treated is an acute opioid overdose, or the risk of opioid abuse.

The present invention also provides the use of a film according to the invention for the manufacture of a medicament for the treatment of a condition in a human patient, optionally wherein the condition to be treated is an acute opioid overdose, or the risk of opioid abuse.

The present invention also provides a product comprising one or more films according to the invention, and packaging. Each of the films may individually be wrapped within a pouch, or multiple films may be wrapped together within the same pouch. Optionally, said pouch is made from PET-lined aluminium. The product may further comprise instructions for use of the film. These instructions may contain information on the recommended frequency or timing of use of the film by a patient, how to use remove the film from its pouch or packaging, how to adhere the film to a mucous membrane, and where within the oral cavity to adhere the film to a mucous membrane.

Any film or films of the present invention may also be used in combination with one or more other drugs or pharmaceutical compositions in the treatment of disease or conditions for which the films of the present invention and/or the other drugs or pharmaceutical compositions may have utility.

The one or more other drugs or pharmaceutical compositions may be administered to the patient by any one or more of the following routes: oral, systemic (e.g. transdermal, intranasal, transmucosal or by suppository), or parenteral (e.g. intramuscular, intravenous or subcutaneous). Compositions of the one or more other drugs or pharmaceutical compositions can take the form of tablets, pills, capsules, semisolids, powders, sustained release formulations, solutions, suspensions, elixirs, aerosols, transdermal patches, bioadhesive films, or any other appropriate compositions. The choice of formulation depends on various factors such as the mode of drug administration (e.g. for oral administration, formulations in the form of tablets, pills or capsules are preferred) and the bioavailability of the drug substance.

Manufacture of the Films

The films according to the invention may be manufactured by preparing a film-forming solution by addition and mixing of the constituent components of the film, distributing this solution onto a solid surface, and permitting the solution to dry on the surface to form a film. To distribute a solution or composition onto a solid surface the solution or composition may simply be poured onto and/or spread evenly over the surface, e.g. by use of a draw-down blade or similar equipment.

A typical method includes the process steps of:
(a) optionally, mixing one or more preservatives in water;
(b) either: (i) mixing the API and, optionally, at least one buffering component in water, or in the solution obtained in step (a), and subsequently adjusting the pH of the solution to the desired level by addition of an appropriate acid or base, typically a diluted aqueous acid or alkali, and preferably adjusting the pH of the solution to from 3.0 to 12.0; or
(ii) adjusting the pH of water, or the solution obtained in step (a), to the desired level by addition of an appropriate acid or base, typically a diluted aqueous acid or alkali, and preferably adjusting the pH to from 3.0 to 12.0, and subsequently mixing the API and, optionally, at least one buffering component in the pH-adjusted solution;
(c) optionally, adding further water and/or one or more plasticizers under further mixing;
(d) adding the alginate salt of monovalent cation under suitable conditions to result in the formation of a viscous cast;
(e) optionally, leaving the cast to de-aerate;
(f) pouring the cast onto a surface and spreading the cast out to the desired thickness;
(g) drying the cast layer, typically at a temperature of from 40 to 70° C. until the residual water content of the film is from 5 to 15% by weight and a solid film is formed; and
(h) optionally, cutting the solid film into pieces of the desired size, further optionally placing these pieces into pouches, preferably wherein the pouches are made from PET-lined aluminium, sealing the pouches and further optionally, labelling them.

Accordingly, an exemplary method for making the films of the present invention includes the process steps of:
(a) mixing the API and, optionally, at least one buffering component in water; adjusting the pH of the solution to the desired level by addition of an appropriate acid or base, typically a diluted aqueous acid or alkali, and preferably adjusting the pH of the solution to from 3.0 to 12.0, or alternatively adjusting the pH to from 3.0 to 7.0, preferably from 3.5 to 5.5, more preferably from 3.5 to 4.5, even more preferably to about 4.0, or alternatively adjusting the pH to from 7.0 to 11.0, preferably from 7.84 to 10.07, more preferably from 8.0 to 10.0, even more preferably from 8.5 to 9.5, and even more preferably still to about 9.0;
(c) optionally, adding further water and/or one or more plasticizers and/or one or more fillers under further mixing;
(d) adding the alginate salt of monovalent cation under suitable conditions to result in the formation of a viscous cast, e.g. by mixing for about 30 minutes or until a lump free dispersion is achieved;
(e) optionally, leaving the cast to de-aerate;
(f) pouring the cast onto a surface, e.g. a plate, preferably a glass plate, and spreading the cast out to the desired thickness, typically by means of an applicator;
(g) drying the cast layer, typically at a temperature of from 40 to 70° C., and preferably from 45 to 55° C., until the residual water content of the film is from 0 to 20% by weight, preferably from 5 to 15% by weight, and more preferably from 9 to 11% by weight, and a solid film is formed; and
(h) optionally, cutting the solid film into pieces of the desired size, further optionally placing these pieces into pouches, preferably wherein the pouches are made from PET-lined aluminium, sealing the pouches and further optionally, labelling them.

In one variant of this exemplary method, suitable for making "low pH" films comprising naloxone present in a salt form, preferably naloxone hydrochloride, the method includes the process steps of:
(a) mixing the API and, optionally, at least one buffering component in water;
(b) adjusting the pH of the solution to the desired level by addition of an appropriate acid or base, typically a diluted aqueous alkali, and preferably adjusting the pH of the solution to from 3.0 to 7.0, preferably from 3.5 to 5.5, more preferably from 3.5 to 4.5, even more preferably to about 4.0;
(c) optionally, adding further water and/or one or more plasticizers and/or one or more fillers under further mixing;
(d) adding the alginate salt of monovalent cation under suitable conditions to result in the formation of a viscous cast, e.g. by mixing for about 30 minutes or until a lump free dispersion is achieved;
(e) optionally, leaving the cast to de-aerate;
(f) pouring the cast onto a surface, e.g. a plate, preferably a glass plate, and spreading the cast out to the desired thickness, typically by means of an applicator;
(g) drying the cast layer, typically at a temperature of from 40 to 70° C., and preferably from 45 to 55° C., until the residual water content of the film is from 0 to 20% by weight, preferably from 5 to 15% by weight, and more preferably from 9 to 11% by weight, and a solid film is formed; and
(h) optionally, cutting the solid film into pieces of the desired size, further optionally placing these pieces into pouches, preferably wherein the pouches are made from PET-lined aluminium, sealing the pouches and further optionally, labelling them.

In one variant of the above exemplary method, suitable for making "high pH" films comprising naloxone present in its free base form, the method includes the process steps of:
(a) mixing the API and, optionally, at least one buffering component in water;
(b) adjusting the pH of the solution to the desired level by addition of an appropriate acid or base, typically a diluted aqueous alkali, and preferably adjusting the pH of the solution to from 7.0 to 11.0, preferably from 7.84 to 10.07, more preferably from 8.0 to 10.0, even more preferably from 8.5 to 9.5, and even more preferably still to about 9.0;
(c) optionally, adding further water and/or one or more plasticizers and/or one or more fillers under further mixing;
(d) adding the alginate salt of monovalent cation under suitable conditions to result in the formation of a viscous cast, e.g. by mixing for about 30 minutes or until a lump free dispersion is achieved;
(e) optionally, leaving the cast to de-aerate;
(f) pouring the cast onto a surface, e.g. a plate, preferably a glass plate, and spreading the cast out to the desired thickness, typically by means of an applicator;
(g) drying the cast layer, typically at a temperature of from 40 to 70° C., and preferably from 45 to 55° C., until the residual water content of the film is from 0 to 20% by weight, preferably from 5 to 15% by weight, and more preferably from 9 to 11% by weight, and a solid film is formed; and (h) optionally, cutting the solid film into pieces of the desired size, further optionally placing these pieces into pouches, preferably wherein the pouches are made from PET-lined aluminium, sealing the pouches and further optionally, labelling them.

An alternative method for manufacturing a film according to the invention includes the process steps of:

(a) mixing one or more preservatives in water;
(b) adjusting the pH of the solution to the desired level by addition of an appropriate acid or base, typically a diluted aqueous acid or alkali, and preferably adjusting the pH of the solution to from 3.0 to 12.0, or alternatively adjusting the pH to from 3.0 to 7.0, preferably from 3.5 to 5.5, more preferably from 3.5 to 4.5, even more preferably to about 4.0, or alternatively adjusting the pH to from 7.0 to 11.0, preferably from 7.84 to 10.07, more preferably from 8.0 to 10.0, even more preferably from 8.5 to 9.5, and even more preferably still to about 9.0;
(c) mixing the API in the pH-adjusted solution;
(d) optionally, adding further water and/or one or more plasticizers and/or one or more fillers under further mixing;
(e) adding the alginate salt of monovalent cation under suitable conditions to result in the formation of a viscous cast, e.g. by mixing for about 30 minutes or until a lump free dispersion is achieved;
(f) optionally, leaving the cast to de-aerate;
(g) pouring the cast onto a surface, e.g. a plate, preferably a glass plate, and spreading the cast out to the desired thickness, typically by means of an applicator;
(h) drying the cast layer, typically at a temperature of from 40 to 70° C., and preferably from 45 to 55° C., until the residual water content of the film is from 0 to 20% by weight, preferably from 5 to 15% by weight, and more preferably from 9 to 11% by weight, and a solid film is formed; and
(i) optionally, cutting the solid film into pieces of the desired size, further optionally placing these pieces into pouches, preferably wherein the pouches are made from PET-lined aluminium, sealing the pouches and further optionally, labelling them.

In one variant of the above alternative method, suitable for making "low pH" films comprising naloxone present in a salt form, preferably naloxone hydrochloride, the method includes the process steps of:

(a) mixing one or more preservatives in water;
(b) adjusting the pH of the solution to the desired level by addition of an appropriate acid or base, typically a diluted aqueous alkali, and preferably adjusting the pH of the solution to from 3.0 to 7.0, preferably from 3.5 to 5.5, more preferably from 3.5 to 4.5, even more preferably to about 4.0;
(c) mixing the API in the pH-adjusted solution;
(d) optionally, adding further water and/or one or more plasticizers and/or one or more fillers under further mixing;
(e) adding the alginate salt of monovalent cation under suitable conditions to result in the formation of a viscous cast, e.g. by mixing for about 30 minutes or until a lump free dispersion is achieved;
(f) optionally, leaving the cast to de-aerate;
(g) pouring the cast onto a surface, e.g. a plate, preferably a glass plate, and spreading the cast out to the desired thickness, typically by means of an applicator;
(h) drying the cast layer, typically at a temperature of from 40 to 70° C., and preferably from 45 to 55° C., until the residual water content of the film is from 0 to 20% by weight, preferably from 5 to 15% by weight, and more preferably from 9 to 11% by weight, and a solid film is formed; and
(i) optionally, cutting the solid film into pieces of the desired size, further optionally placing these pieces into pouches, preferably wherein the pouches are made from PET-lined aluminium, sealing the pouches and further optionally, labelling them.

In one variant of the above alternative method, suitable for making "high pH" films comprising naloxone present in its free base form, the method includes the process steps of:

(a) mixing one or more preservatives in water;
(b) adjusting the pH of the solution to the desired level by addition of an appropriate acid or base, typically a diluted aqueous alkali, and preferably adjusting the pH of the solution to from 7.0 to 11.0, preferably from 7.84 to 10.07, more preferably from 8.0 to 10.0, even more preferably from 8.5 to 9.5, and even more preferably still to about 9.0;
(c) mixing the API in the pH-adjusted solution;
(d) optionally, adding further water and/or one or more plasticizers and/or one or more fillers under further mixing;
(e) adding the alginate salt of monovalent cation under suitable conditions to result in the formation of a viscous cast, e.g. by mixing for about 30 minutes or until a lump free dispersion is achieved;
(f) optionally, leaving the cast to de-aerate;
(g) pouring the cast onto a surface, e.g. a plate, preferably a glass plate, and spreading the cast out to the desired thickness, typically by means of an applicator;
(h) drying the cast layer, typically at a temperature of from 40 to 70° C., and preferably from 45 to 55° C., until the residual water content of the film is from 0 to 20% by weight, preferably from 5 to 15% by weight, and more preferably from 9 to 11% by weight, and a solid film is formed; and
(i) optionally, cutting the solid film into pieces of the desired size, further optionally placing these pieces into pouches, preferably wherein the pouches are made from PET-lined aluminium, sealing the pouches and further optionally, labelling them.

A yet further method, suitable for making "low pH" films comprises the following steps:

(a) mixing one or more excipients and one or more preservatives in an acidic aqueous solution, optionally at a temperature from 20 to 40° C.;
(b) separately, dissolving the API in water, optionally under mixing at a temperature from 20 to 40° C.;
(c) mixing the solution obtained in step (a) with the alginate salt of monovalent cation;
(d) adding the solution obtained in step (b) to the solution obtained in step (c) under suitable conditions to result in the formation of a viscous cast;
(e) optionally, adding a chelating agent to the cast;
(f) optionally, leaving the cast to de-aerate;
(g) pouring the cast onto a surface and spreading the cast out to the desired thickness;

(h) drying the cast layer, typically at a temperature of from 40 to 70° C. until the residual water content of the film is from 5 to 15% by weight and a solid film is formed; and (i) optionally, cutting the solid film into pieces of the desired size, further optionally placing these pieces into pouches, preferably wherein the pouches are made from PET-lined aluminium, sealing the pouches and further optionally, labelling them.

In an alternative variant of any of the above methods, after the viscous cast is poured onto a surface, it is first spread out to a thickness of about 2 mm by means of an applicator with a slit height of about 2 mm, and is then subsequently spread out to a thickness of about 1 mm by means of an applicator with a slit height of about 1 mm.

Typically, the alginate salt(s) are added to the API-containing water solution. Alternatively, the API and the alginate salt(s) are both dissolved together in solution. Alternatively, the API may be added to the alginate solution so as to give an emulsion or suspension of the API in the alginate solution. Alternatively, the film-forming composition of the invention may comprise both dissolved and non-dissolved active ingredients. For example, a film-forming composition may comprise a combination of active ingredient dissolved in the alginate solution and active ingredient suspended in the solution.

Additional API may be applied to the surface of the film before or after drying, e.g. as an aerosol spray onto a dry or wet film. An active ingredient may also be applied as a powder onto the surface of the film. A flavouring agent may additionally be applied in such a way.

The publications, patent publications and other patent documents cited herein are entirely incorporated by reference. Herein, any reference to a term in the singular also encompasses its plural. Where the term "comprising", "comprise" or "comprises" is used, said term may substituted by "consisting of", "consist of" or "consists of" respectively, or by "consisting essentially of", "consist essentially of" or "consists essentially of" respectively. Any reference to a numerical range or single numerical value also includes values that are about that range or single value. Any reference to naloxone also encompasses a physiologically acceptable salt thereof unless otherwise indicated. Any reference to alginate encompasses any physiologically acceptable salt thereof unless otherwise indicated. Unless otherwise indicated, any % value is based on the relative weight of the component or components in question.

EXAMPLES

The following are Examples that illustrate the present invention. However, these Examples are in no way intended to limit the scope of the invention. References to "naloxone" or a pharmaceutically acceptable salt thereof throughout this Examples section refer specifically to the (−) enantiomer of naloxone, i.e. (−)-naloxone, or the pharmaceutically acceptable salt thereof, unless it is stated otherwise.

Example 1: Preparation of Naloxone-Containing Films

Two basic film formulation protocols were developed. One film formulation protocol produced so-called "low pH" films, wherein the pH of the film formulation prior to coating and drying was about 4.2. The other film formulation protocol produced so-called "high pH" films, wherein the pH of the film formulation prior to coating and drying was about 9.

Preparation of Low pH Naloxone Buccal Films

Batch formulae comprising (−)-naloxone hydrochloride dihydrate as the API for each individual dose strength of low pH naloxone oral films are listed in Table 1. Calculations are based on yields of 1000 doses/batch (dose size=3 cm$^2$).

TABLE 1

Batch formulae for production of low pH naloxone films containing different dose strengths of the API.

| Component | Batch formulae for target dose strengths of low pH naloxone buccal films | | | Function |
|---|---|---|---|---|
| Target dose strength | 2 mg/dose | 10 mg/dose | 20 mg/dose | |
| Naloxone hydrochloride dihydrate (g) | 2.0 | 10.0 | 20.0 | API |
| Water (mL) | 200 | 200 | 200 | Solvent |
| Sorbitol (g) | 7 | 7 | 7 | Plasticizer |
| Glycerol (g) | 7 | 7 | 7 | Plasticizer |
| Sodium alginate (g) | 26.7 | 26.7 | 26.7 | Film-forming polymer |
| Sodium hydroxide (diluted) | q.s. to pH 4.2 | q.s. to pH 4.2 | q.s. to pH 4.2 | pH adjustment | q.s. = quantum satis.

The films were produced according to the following procedure:

The majority of the purified water was added to a vessel and naloxone hydrochloride dihydrate was added and dissolved under mixing.

The pH of the solution was adjusted to 4.2 by addition of a requisite quantity of diluted sodium hydroxide.

The batch volume was increased to the correct total amount by addition of the remainder of the purified water.

The glycerol and sorbitol liquid, partially dehydrated, were added under mixing.

The sodium alginate was added under mixing (in a food processor) for about 30 minutes or until a lump free dispersion was achieved, resulting in a viscous cast.

The cast was left overnight for de-aeration.

The cast was poured onto a glass plate and spread out to a thickness of 1 mm by means of an applicator.

The cast layer was dried in a drying cabinet heated to approximately 50° C. until a residual water content of from 9 to 11% by weight was achieved and a solid film was formed.

The solid film was cut into pieces measuring 15×20 mm with a knife.

The resulting films were placed individually into aluminium pouches, sealed with a heat sealer and labelled.

Preparation of High pH Naloxone Buccal Films

A batch formula comprising (−)-naloxone hydrochloride dihydrate as the API for a 10 mg dose strength of high pH naloxone oral films is provided in Table 2. Calculations are based on yields of 1000 doses/batch (dose size=3 cm$^2$).

TABLE 2

Batch formula for production of high pH naloxone films containing 10 mg dose strength of the API.

| Component Target dose strength | Batch formula for target dose strength of high pH naloxone buccal films 10 mg/dose | Function |
| --- | --- | --- |
| Naloxone hydrochloride dihydrate (g) | 10.0 | API |
| Water (mL) | 200 | Solvent |
| Sorbitol (g) | 7 | Plasticizer |
| Glycerol (g) | 7 | Plasticizer |
| Sodium alginate (g) | 26.7 | Film-forming polymer |
| Sodium hydroxide (1M) | q.s. to pH 9 | pH adjustment | q.s. = quantum satis.

The films were produced according to the following procedure:

The majority of the purified water was added to a vessel and naloxone hydrochloride dihydrate was added and dissolved under mixing.

1 M aqueous NaOH was added to raise the pH of the solution from about 4 to about 9, and naloxone was precipitated from the solution in its non-ionized form.

The glycerol and sorbitol liquid, partially dehydrated, were added under mixing.

The sodium alginate was added under mixing (in a food processor) for about 30 minutes or until a lump free dispersion was achieved, resulting in a viscous cast.

The cast was left overnight for de-aeration.

The cast was poured onto a glass plate and spread out to a thickness of 1 mm by means of an applicator.

The cast layer was dried in a drying cabinet heated to approximately 50° C. until a residual water content of from 9 to 11% by weight was achieved and a solid film was formed.

The solid film was cut into pieces measuring 15×20 mm with a knife.

The resulting films were placed individually into aluminium pouches, sealed with a heat sealer and labelled.

Preparation of Naloxone Buccal Films Containing Additional Components

Following the same basic protocols as described above, low pH and high pH films comprising additional components, such as one or more permeability enhancers, one or more buffering components, and one or more SNEDDS components. Batch formulae comprising (−)-naloxone hydrochloride dihydrate as the API for various formulations of buccal films, each comprising 10 mg/dose of the API, are listed in Table 3. Calculations are based on yields of 1000 doses/batch (dose size=3 cm$^2$).

TABLE 3

Batch formulae for production of low pH naloxone films containing different dose strengths of the API.

| | Batch formulae for naloxone 10 mg/dose films | | | | | |
| --- | --- | --- | --- | --- | --- | --- |
| Component | Low pH | High pH | Low pH with EDTA | High pH with EDTA | Low pH with EDTA and Citric acid | Function |
| Naloxone hydrochloride dihydrate (g) | 10 | 10 | 10 | 10 | 11.0 | API |
| Water (mL) | 200 | 200 | 200 | 200 | 200 | Solvent |
| Sorbitol (g) | 7 | 7 | 7 | 7 | 7 | Plasticizer |
| Glycerol (g) | 7 | 7 | 7 | 7 | 7 | Plasticizer |
| Sodium alginate (g) | 26.7 | 26.7 | 26.7 | 26.7 | 26.7 | Film-forming polymer |
| 1M NaOH | q.s. to pH 4.2 | q.s. to pH 9 | q.s. to pH 5.0 | q.s. to pH 9 | q.s. to pH 5.0 | pH adjustment |
| 0.1M EDTA-Na$_2$ (mL) | — | — | 18.5 | 18.5 | 18.5 | Permeability enhancer (para) |
| Citric acid (g) | — | — | — | — | 1.2 | Buffering |

| | Batch formulas for naloxone 10 mg/dose films | | | |
| --- | --- | --- | --- | --- |
| Component | Low pH with EDTA, Oleic acid and Tween 80 | Low pH with SNEDDS emulsion | Low pH with EDTA and SNEDDS emulsion | Function |
| Naloxone (g) | 10 | 10 | 10 | API |
| Water (mL) | 200 | 200 | 200 | Solvent |
| Sorbitol (g) | 7 | 7 | 7 | Plasticizer |
| Glycerol (g) | 7 | 7 | 7 | Plasticizer |
| Sodium alginate (g) | 26.7 | 26.7 | 26.7 | Viscosity modifier |
| 1M NaOH | q.s. to pH 4.2 | q.s. to pH 9 | q.s. to pH 4.2 | pH adjustment |
| 0.1M EDTA-Na (mL) | 18.5 | — | 18.5 | Permeability enhancer (para) |

TABLE 3-continued

| | | | | |
|---|---|---|---|---|
| Oleic acid (g) | 0.5 | — | 1.0 | Permeability enhancer (trans) |
| Tween 80 (g) | 0.25 | — | — | SNEDDS component |
| PEG 400 (g) | — | 1.34 | 1.34 | SNEDDS component |
| Labrasol (g) | — | 0.66 | 0.66 | SNEDDS component |
| Kolliphore EL (g) | — | 0.66 | 0.66 | SNEDDS component | q.s. = quantum satis.

Evaluation Criteria

After manufacture, each batch was evaluated with respect to the following criteria:

| Property | Control |
|---|---|
| 1. Cast texture: | lump free, homogenous viscous cast (visual inspection) free of bubbles prior to coating (visual inspection) |
| 2. Residual moisture**: | 9-11% (in process control) |
| 3. Film appearance**: | translucent and colour homogenous (visual inspection) smooth and flat surface structure (visual inspection) pliable and flexible (visual inspection) |
| 4. Dose weight homogeneity: | weighing of doses randomly selected within a film batch |
| 5. Naloxone content***: | target dose strength within ± 10% (RPC-HPLC (reverse phase high performance liquid chromatography) analysis) |

*Residual moisture: IR (infrared)-induced water vaporization combined with real-time weight measurement was used. Percentage of change in weight at start until no further change was observed as the measure of residual moisture.
**Some film batches were inspected and analysed with respect to surface structure with electron microscopy and light microscopy. Crystal content was investigated in some films with differential scanning calorimetry.
***Naloxone content and homogeneity: HPLC-RPC separation with detection at 220 and 282 nm was used. Amount naloxone/dose was calculated using a naloxone standard curve.

Evaluation of Low pH Naloxone Films

Lump free, homogenous viscous casts could be prepared with each individual batch formula/protocol for the low pH naloxone films. Naloxone HCl dihydrate was fully dissolved in the liquid (water) phase. Air bubbles generated during preparation of the casts and which introduce inhomogeneity in the films, were removed by leaving the cast overnight at room temperature for passive de-aeration prior to coating.

All prepared films had smooth, and flat surface structures with flexible properties when dried to a water content of 9-11%. The 2 mg films were transparent whilst the 10 and 20 mg films were homogenous in appearance, but more opaque (see light microscope images in FIGS. 1A-1C).

Scanning electron micrographs (SEM) of naloxone 10 mg/dose films (batch #1) showed that they are homogenous (FIG. 2). No sharp calorimetric changes were detected by Differential Scanning calorimetry (DSC) (FIG. 3) of 2 mg (yellow curve), 10 mg (upper blue curve) and 20 mg (lower blue curve) naloxone low pH films, suggesting absence of crystalline particles.

Dose weight and dosage homogeneity data from two low pH 10 mg naloxone films (batch #5 and batch #10) prepared during this study are shown in Table 4. These data indicate a formulation which is reproducible and gives low variation, both within and between batches.

TABLE 4

Weight, dose and homogeneity data from two batches of low pH 10 mg naloxone films.

| | Weight (mg) | Dose (mg/dose) | Homogeneity (mg Naloxone/mg film) |
|---|---|---|---|
| Low pH naloxone 10 mg (batch #5) | | | |
| Average | 46.6 | 10.1 | 0.216 |
| Standard deviation | 0.6 | 0.2 | 0.004 |
| RSD % | 1.2 | 2.0 | 1.7 |
| Number of samples analyzed | | 6 | |
| Low pH naloxone 10 mg (batch #10) | | | |
| Average | 44.1 | 9.7 | 0.218 |
| Standard deviation | 1.5 | 0.3 | 0.002 |
| RSD % | 3.5 | 3.1 | 0.8 |
| Number of samples analyzed | | 6 | |

RSD = relative standard deviation.

Evaluation of High pH Naloxone Films

Lump free, viscous casts as suspensions could be prepared using the batch formula/protocol for high pH naloxone films. Air bubbles generated during preparation of the casts and which introduce inhomogeneity in the films, were removed by leaving the cast overnight at room temperature for passive de-aeration prior to coating.

All prepared films had smooth, and flat surface structures with flexible properties when dried to a water content of 9-11%. The 2 mg films were transparent whilst the 10 and 20 mg films were homogenous and white.

During preparation of high pH films, it was observed that transfer of the ionized form to the non-ionized naloxone form by increasing the pH gradually to pH 9 needs to be done carefully so as not to exceed the target pH. The pH in the suspension decreases slightly with time and further adjustments may be needed to keep the solution at the correct pH. The pH needed to be controlled and adjusted after mixing with alginate and prior to coating.

An alternative method to prepare high pH films was tested on one batch (high pH 10 mg batch #3). This cast was prepared according to the process for low pH films followed by precipitation of naloxone in the mixed cast in presence of sodium alginate. Light microscopic images of this batch and batch #2, in which naloxone was precipitated in absence of alginate, is shown in FIGS. 4A-4B.

Figure 5B:
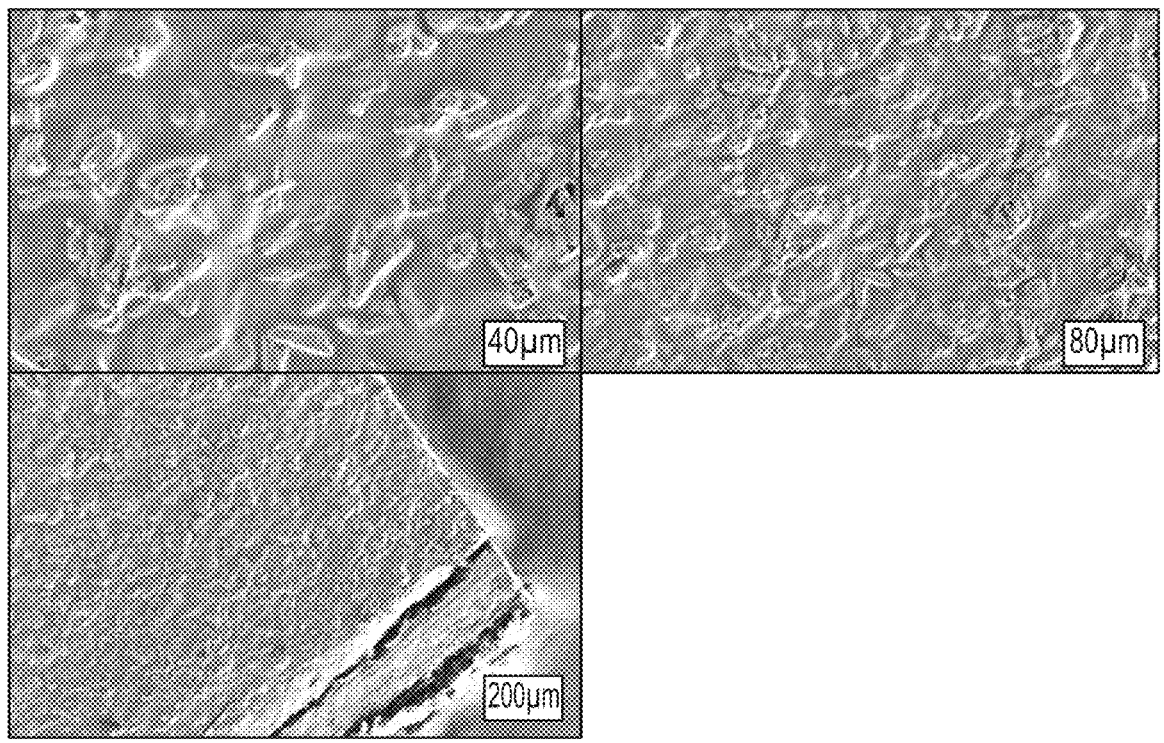
Figure 5C:
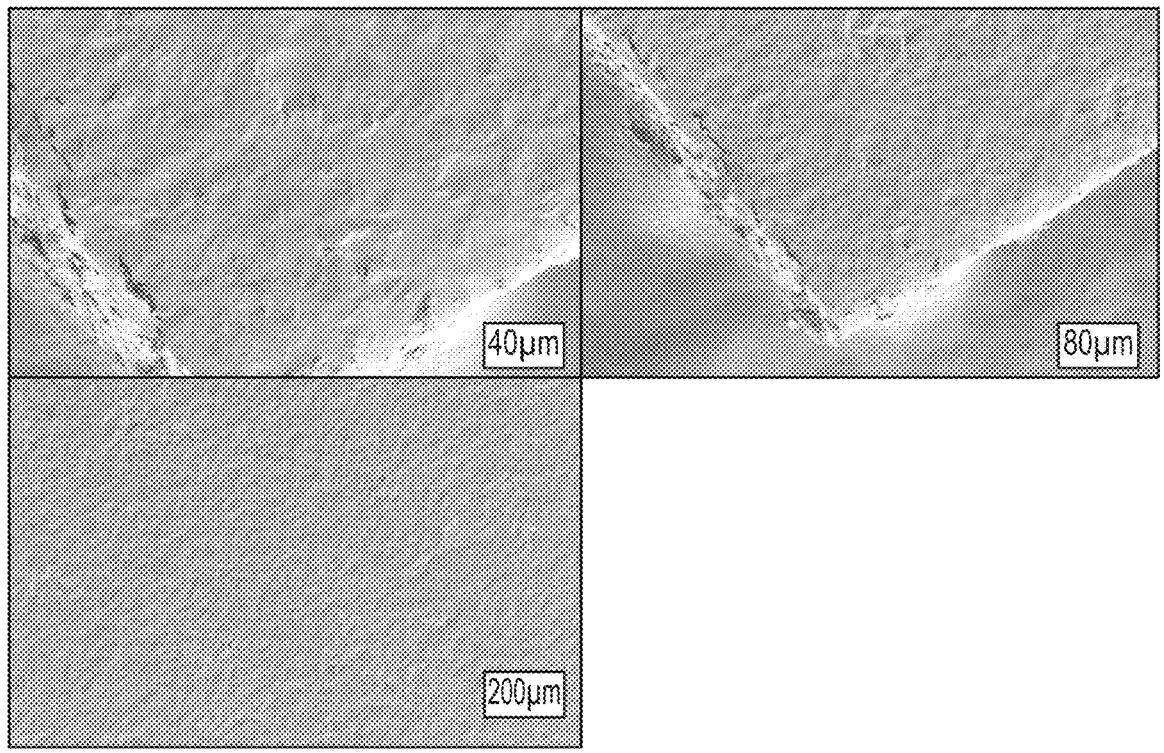

Electron micrographs of three high pH naloxone 10 mg film batches (batch #2, #3 and #10) shows presence of crystalline material (FIGS. 5A-5C).

Figure 3:
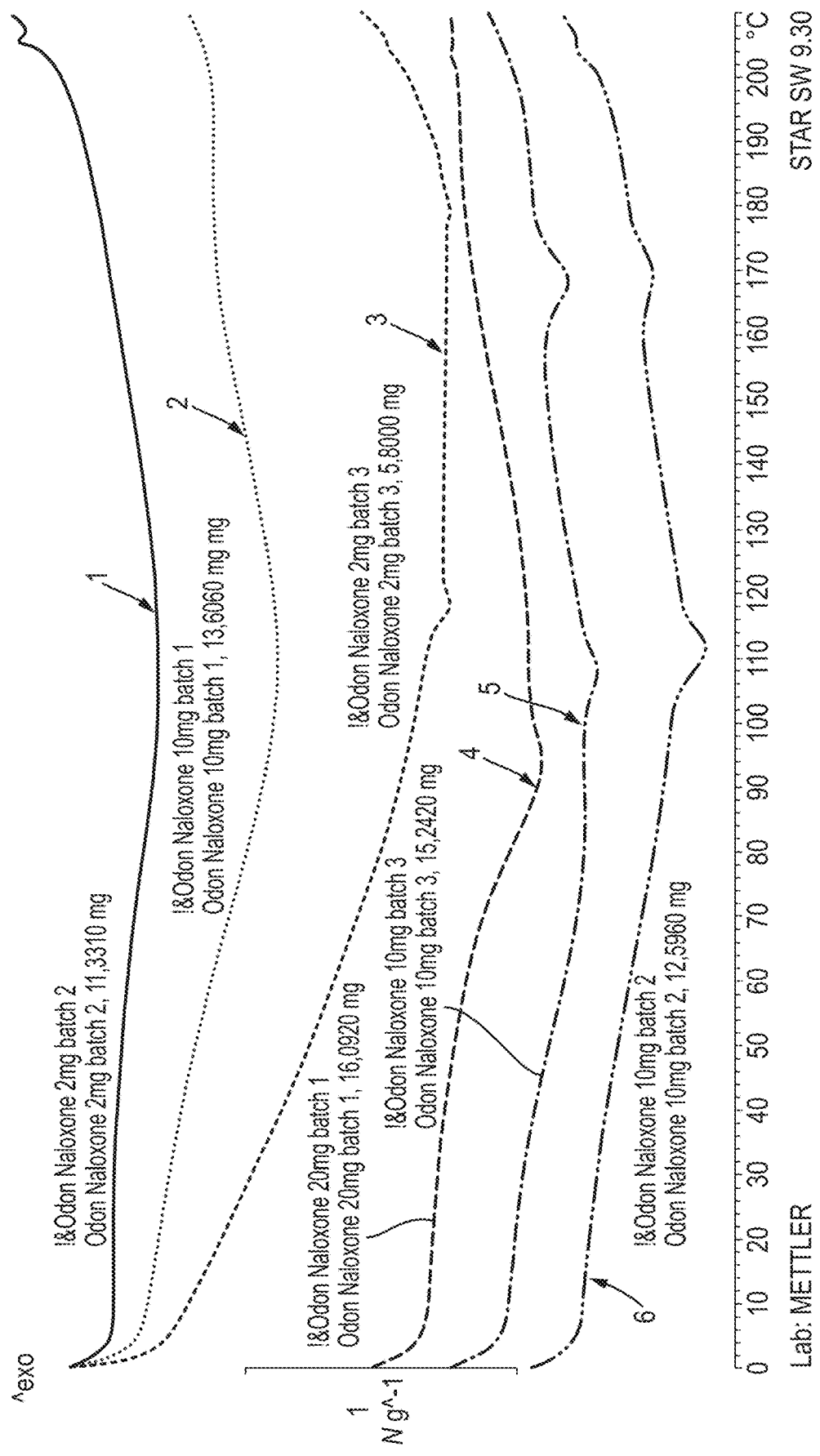
FIG. 3: Differential scanning calorimetry curves for low pH and high pH films containing 2 mg, 10 mg and 20 mg (−)-naloxone. For low pH films, DSC curves are shown for 2 mg (curve 1), 10 mg (curve 2), and 20 mg (curve 4) naloxone films. No melting points are detected in the thermal analysis of these films, suggesting an absence of crystalline particles. For high pH films, DSC curves are shown for a 2 mg (curve 3) and two 10 mg (curves 5 and 6) naloxone films. Melting points corresponding to the melting point for non-ionized naloxone (178° C.) are detected for both 10 mg high pH films, indicating presence of crystalline particles.

As can be seen in FIG. 3, one heat-flow change at temperature close to the melting point for non-ionized naloxone (178° C. according to literature data) is detected for the two analyzed high pH 10 mg naloxone films with DSC (black and red curves in FIG. 3), suggesting presence of crystalline material. (Melting point for naloxone HCl dihydrate is about 200° C., red curve in FIG. 7.)

Dose weight and dosage homogeneity data from high pH 10 mg naloxone films (Table 5) prepared during this study indicate a formulation which is reproducible and gives low variation, both within and between batches.

TABLE 5

Weight, dose and homogeneity data from three batches of high pH 10 mg naloxone films.

| | Weight (mg) | Dose (mg/dose) | Homogeneity (mg Naloxone/mg film) |
|---|---|---|---|
| High pH naloxone 10 mg (batch #12) | | | |
| Average | 43.6 | 9.4 | 0.214 |
| Standard deviation | 1.8 | 0.3 | 0.002 |
| RSD % | 4.1 | 3.4 | 1.0 |
| Number of samples analyzed | | 6 | |
| High pH naloxone 10 mg (batch #17) | | | |
| Average | 43.3 | 8.9 | 0.206 |
| Standard deviation | 0.7 | 0.2 | 0.002 |
| RSD % | 1.6 | 2.3 | 0.9 |
| Number of samples analyzed | | 6 | |
| High pH naloxone 10 mg (batch #26) | | | |
| Average | 44.7 | 9.1 | 0.202 |
| Standard deviation | 2.2 | 0.2 | 0.008 |
| RSD % | 4.9 | 2.7 | 3.8 |
| Number of samples analyzed | | 6 | |

RSD = relative standard deviation.

Evaluation of Films Containing EDTA and Citric Acid

Both low pH and high pH 10 mg naloxone films containing 0.55 mg EDTA/dose could be obtained. At higher quantities of EDTA, some of the naloxone dose appeared to precipitate in the cast during preparation (confirmed by HPLC). The prepared casts were lump free, homogenous and viscous. Air bubbles generated during cast preparation were removed by leaving the cast overnight at room temperature for passive de-aeration prior to coating.

Figure 6A:
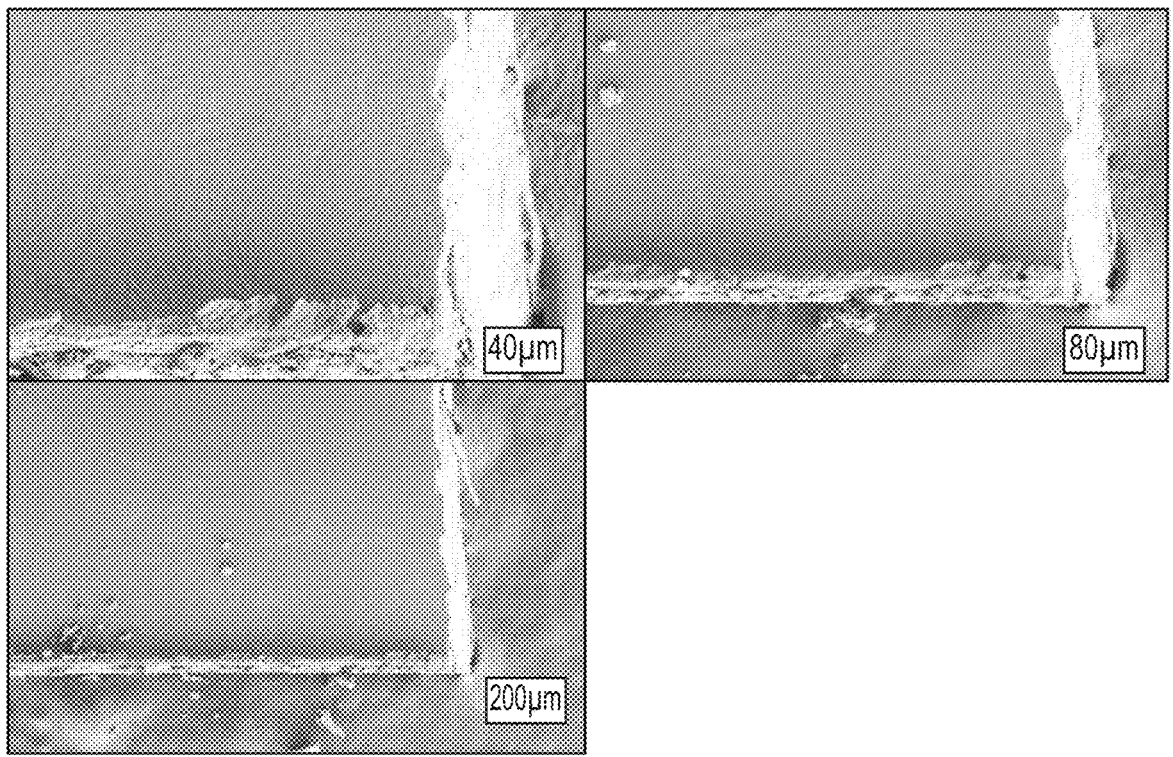
FIGS. 6A-6B: Scanning electron micrograph images of (FIG. 6A) 10 mg low pH (−)-naloxone buccal film containing EDTA (batch #14), and (FIG. 6B) 10 mg high pH (−)-naloxone buccal film containing EDTA (batch #16).
Figure 6B:
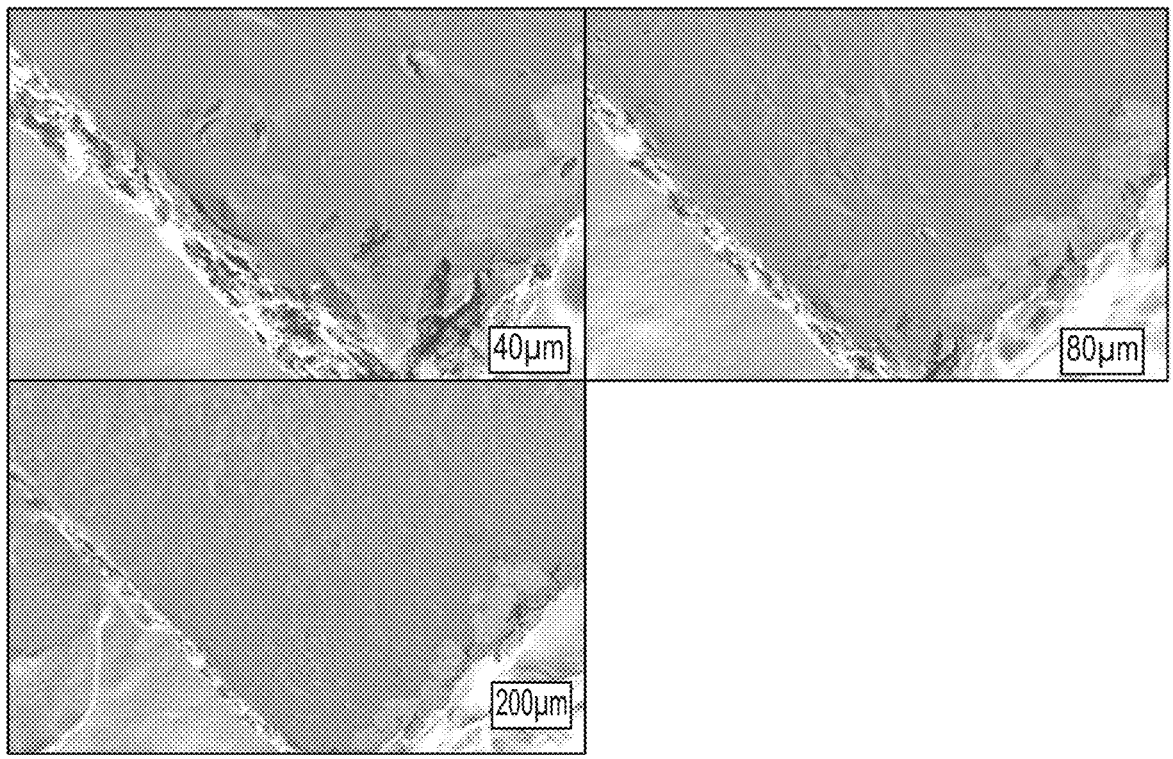

Both preparations generated smooth films with a flat surface structures and flexible properties when dried to a water content of 9-11%. The low pH film was colorless and transparent whilst the high pH film was white. SEM of low pH and high pH naloxone 10 mg films containing 0.55 mg EDTA/dose, batch #14 and batch #16, are shown in FIGS. 6A-6B.

Figure 7:
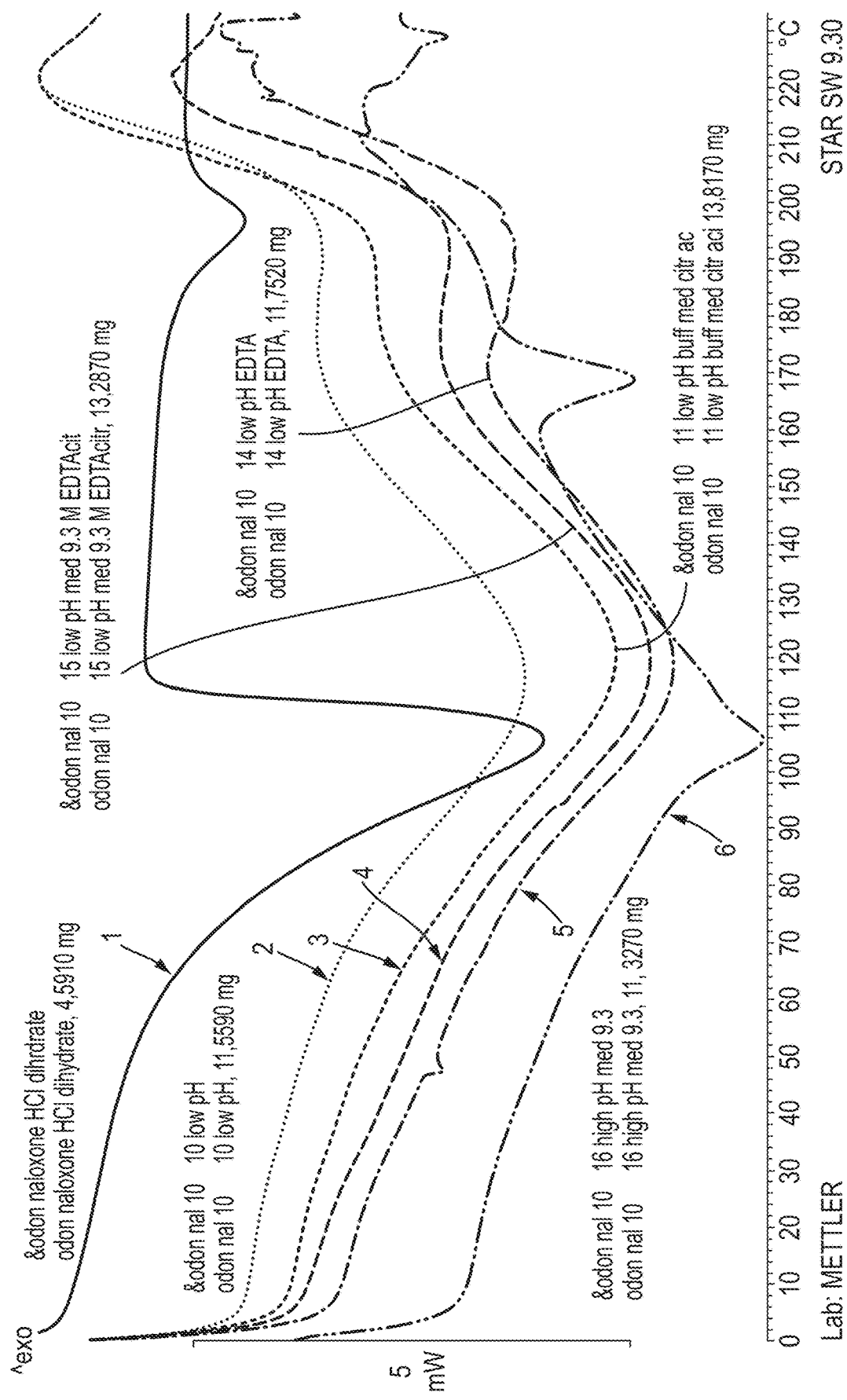
FIG. 7: Differential scanning calorimetry curves for 10 mg naloxone films containing EDTA and/or citric acid. Curve 1: (−)-naloxone HCl dihydrate powder (reference). Curve 2: low pH 10 mg naloxone film. Curve 3: low pH 10 mg naloxone film containing citric acid. Curve 4: low pH 10 mg naloxone film containing EDTA and citric acid. Curve 5: low pH 10 mg naloxone film containing EDTA. Curve 6: high pH 10 mg naloxone film containing EDTA.

One DSC change at a temperature close to the melting point for non-ionized naloxone (178° C.) was detected in the thermal analysis of the high pH film containing EDTA (purple curve in FIG. 7). No crystalline material was detected in the low pH film containing EDTA (brown curve in FIG. 7).

A low pH film with a similar composition to the nasal spray Narcan® was also prepared. Narcan® contains naloxone hydrochloride, EDTA, citric acid and benzalkonium chloride [10]. Citric acid is utilized as a buffer and benzalkonium chloride as an antimicrobial agent and preservative.

Two formulations were prepared: one in which only citric acid was added to the low pH 10 mg naloxone recipe (batch #11), and one containing both EDTA and citric acid (batch #15) as in the recipe for Narcan®. Benzylalcohol was excluded from the recipe. Compositions for these two formulations are provided in Table 6.

TABLE 6

Film composition for batch #11 and batch #15

| | low pH Naloxone 10 mg film with citric acid and EDTA | |
|---|---|---|
| | Batch #11 | Batch #15 |
| Naloxone (mg/dose) | 10 | 10 |
| Citric acid (mg/dose) | 1.2 | 1.2 |
| EDTA (mg/dose) | — | 0.55 |

Figure 8A:
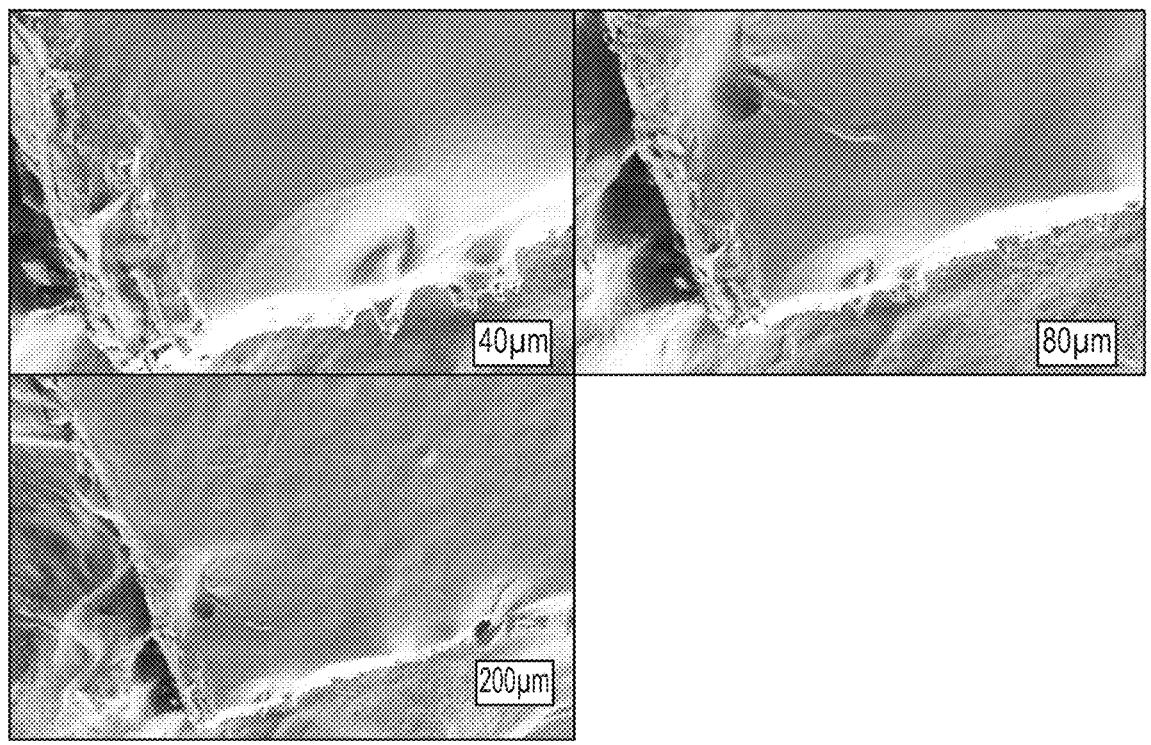
FIGS. 8A-8B: Scanning electron micrograph images of 10 mg low pH (−)-naloxone buccal film, additionally comprising (FIG. 8A) citric acid (batch #11)
Figure 8B:
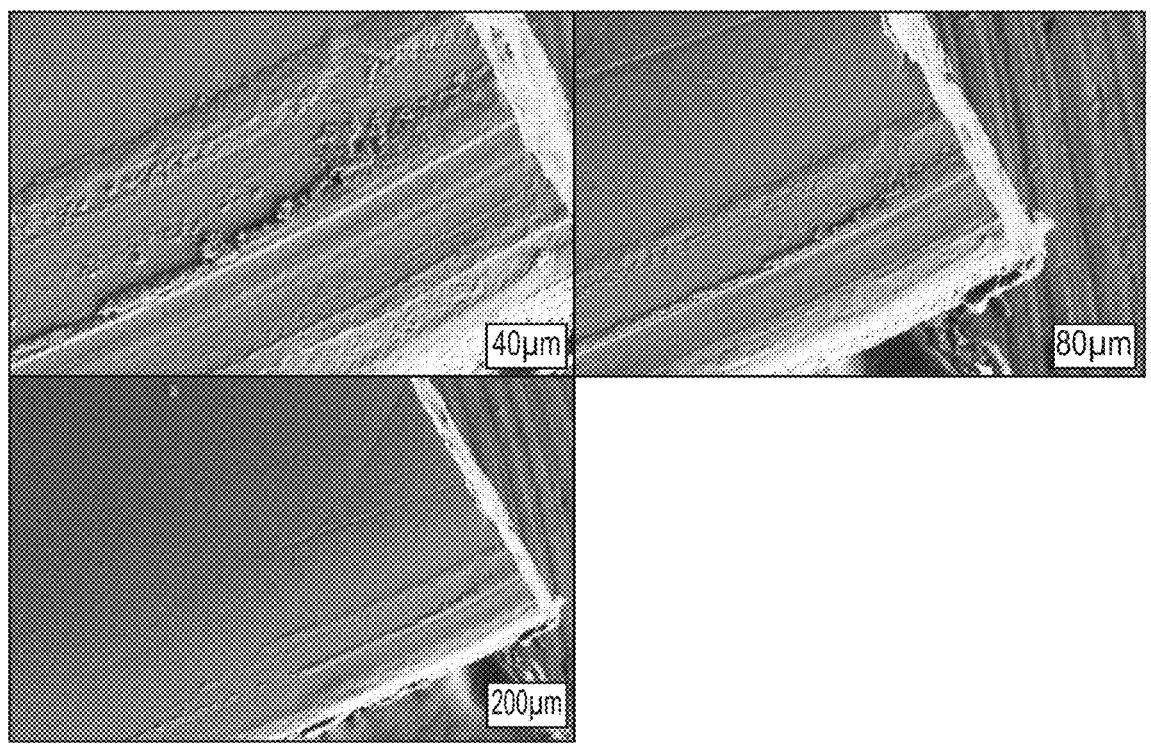

SEM micrographs of the citric acid containing film (batch #11) and the film containing citric acid and EDTA (batch #15), are shown in FIGS. 8A-8B. No change in DSC could be detected, indicating that batch #11 (black curve in FIG. 7) and batch #15 (green curve in FIG. 7) contain no crystalline material.

Dose weight and dosage homogeneity data from 10 mg naloxone films containing EDTA and citric acid are given in Table 7. Data indicates formulations which are reproducible and gives low variation.

TABLE 7

Weight, dose and homogeneity data from four batches of naloxone films containing EDTA and/or citric acid.

| | Weight (mg) | Dose (mg/dose) | Homogeneity (Mg Naloxone/mg film) |
|---|---|---|---|
| Low pH naloxone 10 mg with citric acid. (batch #11) | | | |
| Average | 46.3 | 9.9 | 0.214 |
| Standard deviation | 0.7 | 0.2 | 0.004 |
| RSD % | 1.6 | 2.0 | 1.8 |
| Number of samples analyzed | | 6 | |
| Low pH naloxone 10 mg with EDTA and citric acid (batch #15) | | | |
| Average | 45.4 | 8.9 | 0.195 |
| Standard deviation | 0.6 | 0.3 | 0.008 |
| RSD % | 1.2 | 3.6 | 3.9 |
| Number of samples analyzed | | 6 | |
| Low pH naloxone 10 mg with EDTA (batch #14) | | | |
| Average | 46.4 | 10.3 | 0.221 |
| Standard deviation | 2.0 | 0.3 | 0.004 |
| RSD % | 4.4 | 3.3 | 1.6 |
| Number of samples analyzed | | 6 | |
| High pH naloxone 10 mg with EDTA (batch #16) | | | |
| Average | 42.6 | 8.6 | 0.201 |
| Standard deviation | 2.1 | 0.6 | 0.008 |
| RSD % | 4.9 | 7.2 | 4.1 |
| Number of samples analyzed | | 6 | |

RSD = relative standard deviation.

Evaluation of Films Containing Oleic Acid

Experiments to add oleic acid to the formulation were carried out and oleic acid was integrated in placebo film by the following two methods.

1. Experiments in which oleic acid was included in the formulation at different concentrations were performed. Addition of oleic acid corresponding to c. 5 mg/dose (c. 10 w/w % in dried film) resulted in phase separation in the cast and films with a "greasy" surface appearance when dried.

Attempts were made to form a stable emulsion by including a surfactant, Tween 80, in the formulation containing oleic acid. Several combinations were tested, and phase separation could be avoided when the quantity of oleic acid was reduced to 0.25 mg/dose (c. 0.5 w/w % in dried films). The obtained cast was homogenous but displayed slightly oily surfaces. Dried films obtained were slightly oily, but the oil appeared not to transfer to other surfaces.

2. A formulation with self-nanoemulsifying drug delivery system (SNEDDS) according to Friedl et al. [11] was also evaluated. The SNEDDS composition (formulation 2 in Friedl et al.) consisted of PEG, Labrasol, Chremophore EL and Chremophore RH40. By replacing the latter with oleic acid, an acceptable cast could be prepared. The films prepared by SNEDDS emulsions with 3.75 mg to 5.6 mg oleic acid/dose were, however, greasy and brittle. However, when the quantity of oleic acid was reduced to 1.33 mg/dose a good cast and good films (although slightly greasy) could be achieved.

Low and high pH 10 mg naloxone films were then prepared using two methods to integrate oleic acid.

Figure 9A:
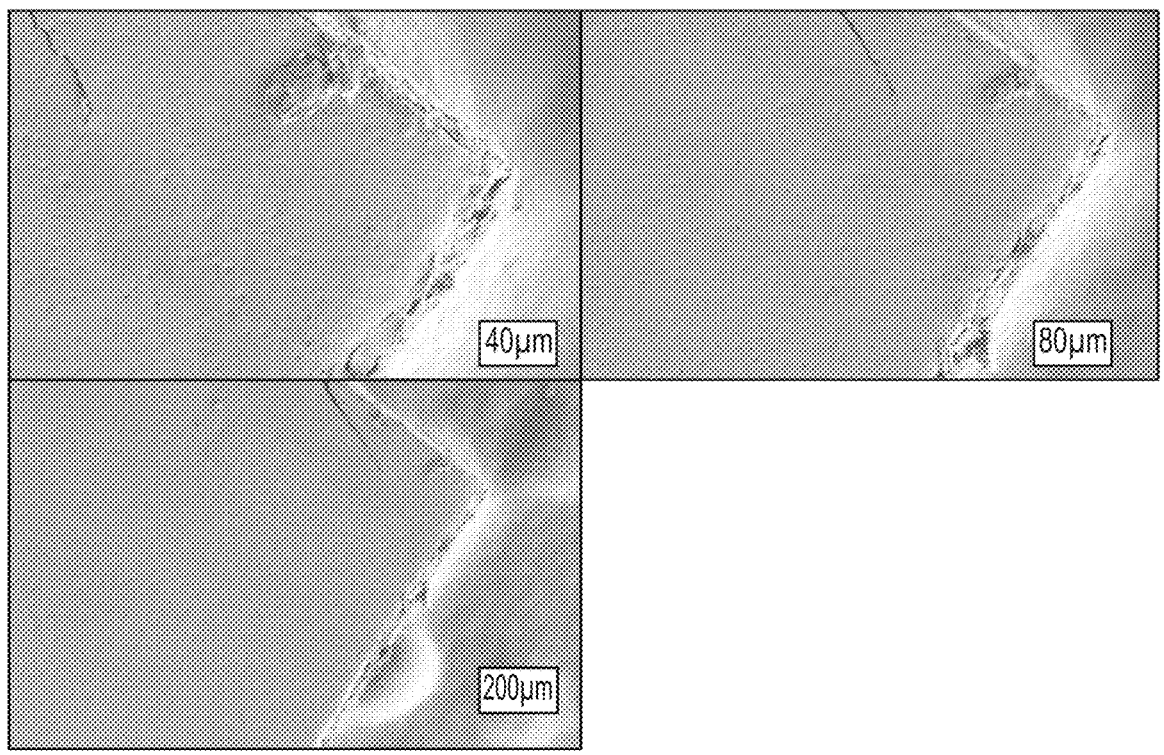
FIGS. 9A-9B: Scanning electron micrograph images of 10 mg low pH (−)-naloxone buccal film, additionally comprising (FIG. 9A) oleic acid as part of SNEDDS (batch #18)
Figure 9B:
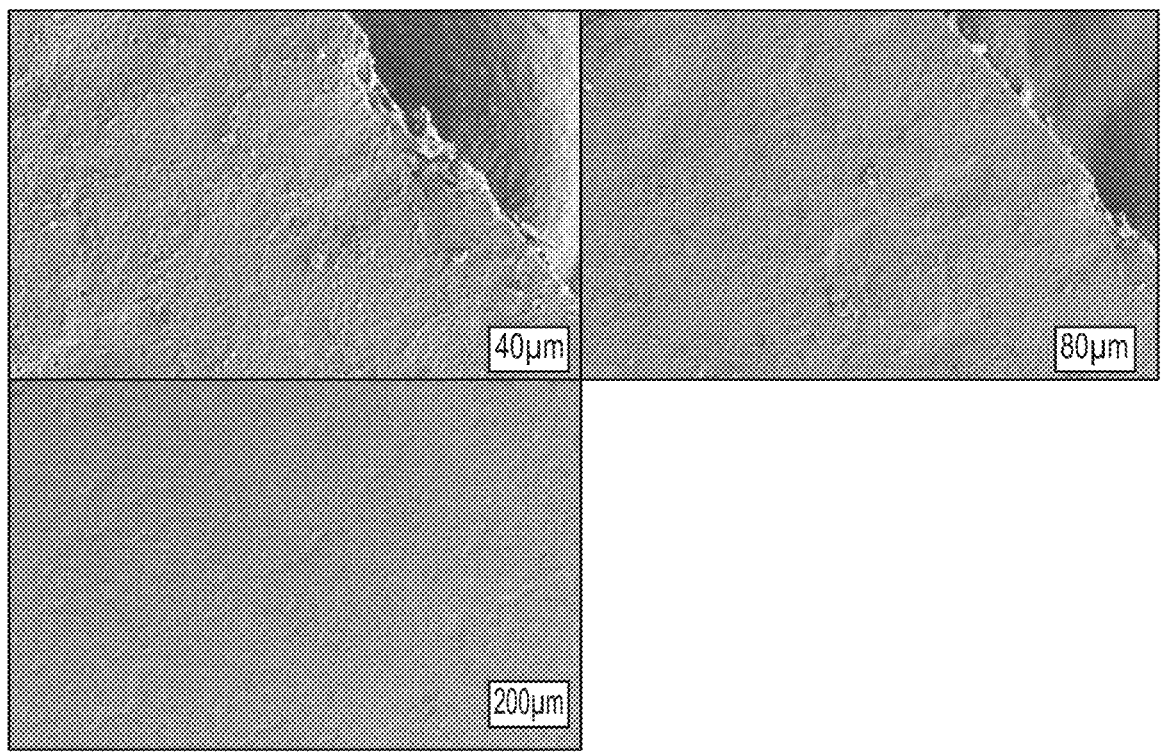
Figure 10:
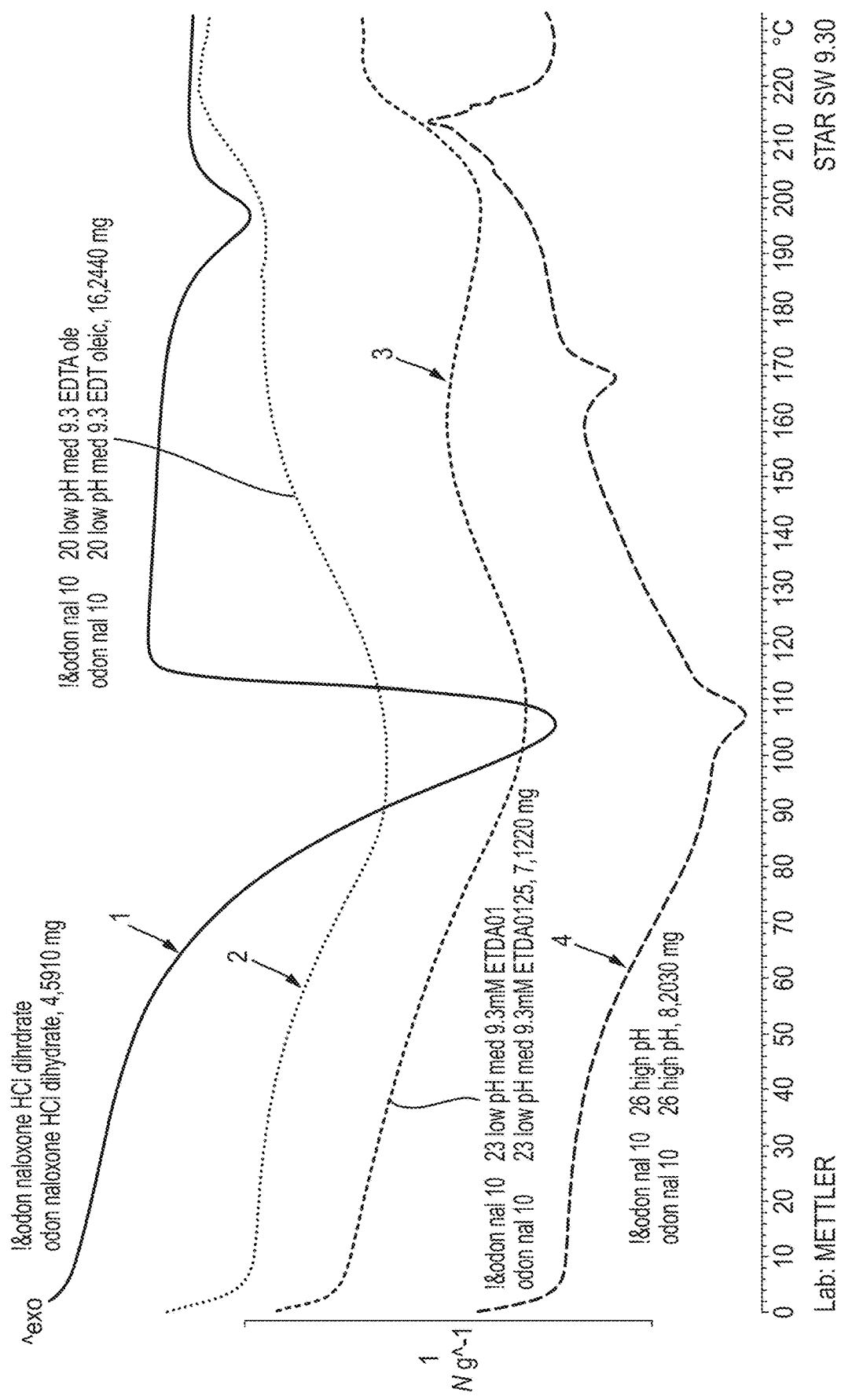
FIG. 10: Differential scanning calorimetry curves for low pH 10 mg naloxone films containing oleic acid. Curve 1: (−)-naloxone HCl dihydrate powder (reference). Curve 2: low pH 10 mg naloxone film containing oleic acid in SNEDD, and EDTA (batch #20). Curve 3: low pH 10 mg naloxone film containing oleic acid, Tween 80 and EDTA (batch #23). Curve 4: high pH 10 mg naloxone film (reference).

Method 1:

A low pH formulation with oleic acid in SNEDDS containing: PEG 400 (0.67 g/100 mL cast), Labrasol (0.33 g/100 mL cast), Chremophor EL (0.33 g/100 mL cast) and oleic acid in a quantity corresponding to 1.33 mg/dose. A low pH formulation with SNEDDS and EDTA was also prepared in a quantity to 0.55 mg/dose. Good films, although slightly greasy, could be prepared from the low pH 10 mg naloxone SNEDDS containing formulation both without (batch #18) and with EDTA (batch #20). SEM micrographs of the films are shown in FIGS. 9A-9B. As expected, no change in DSC was detected in the thermal analysis of batch #20 (black curve in FIG. 10). The high pH 10 mg naloxone formulation containing SNEDDS formed a non-homogenous cast (clumps) during pH adjustment to pH 9, most probably due to "detergent"-forming of the oil at the elevated pH. This formulation was considered to be unsuitable to scale up.

Figure 11:
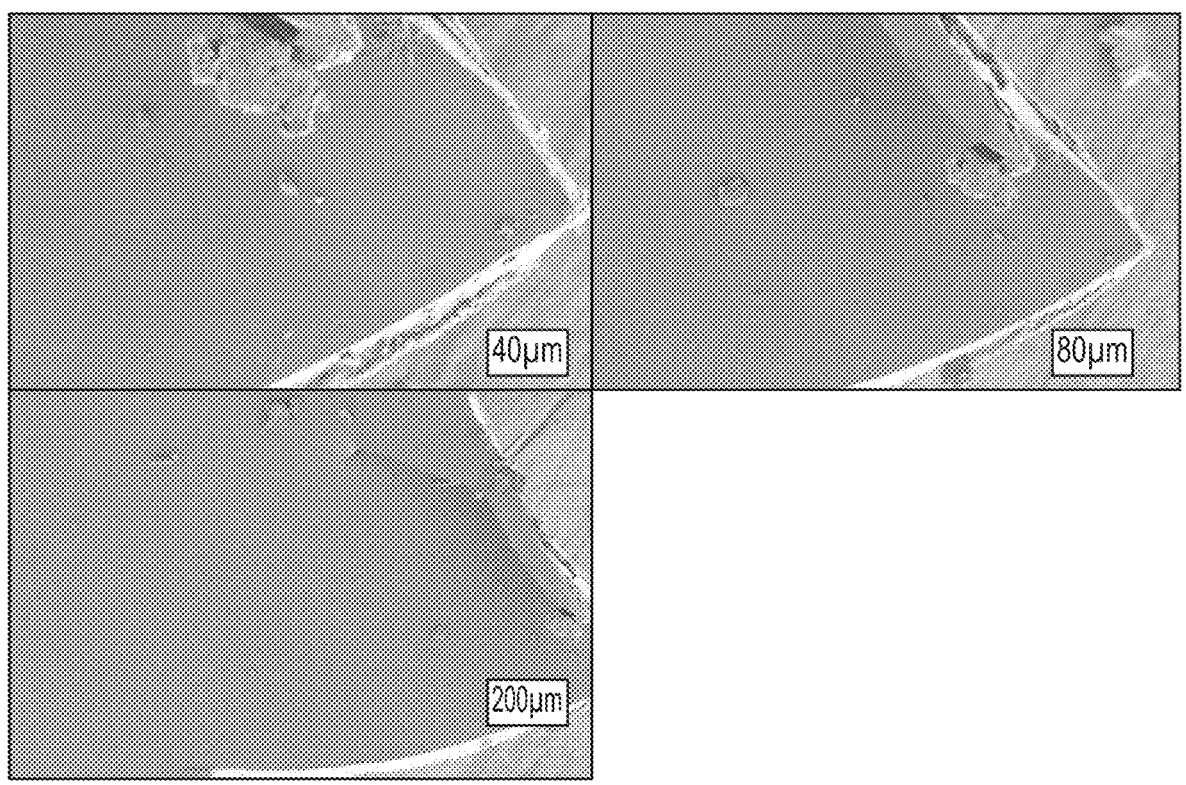
FIG. 11: Scanning electron micrograph images of 10 mg low pH (−)-naloxone buccal film, additionally comprising oleic acid, Tween 80 and EDTA (batch #23).

Method 2:

A batch of a formulation containing Tween 80 (0.11 g/100 mL cast) and oleic acid in a quantity corresponding to 0.25 mg/dose was prepared. Good films could be obtained from a cast with high viscosity, with the low pH 10 mg naloxone formulation containing oleic acid and Tween 80 (batch #23). The films were slightly greasy, but the grease was not transferred to other surfaces. The SEM image (FIG. 11) shows a film with a smooth surface. No crystalline material was detected in the thermal analysis with DSC (blue curve in FIG. 10).

No films could be prepared with the high pH 10 mg naloxone formulation containing oleic acid and Tween 80 since the formed cast became too viscous to coat.

Conclusions

The results in this Example show the possibility to formulate naloxone buccal films with ionized or non-ionized species and presence of permeation enhancers. The main conclusions of this study are summarized below.

Lump free, homogenous viscous cast, free of bubbles were obtained, by allowing the cast to de-aerate for over 15 hours.

Films produced were homogenous and had a smooth and flat surface. They were pliable and flexible and easy to handle and considered as being easy to package and store and administer to a patient.

Results from the study suggests that low pH films with dose strengths up to approximately 20 mg/3 $cm^2$ naloxone can be produced with apparent molecular dispersion of naloxone.

Dose weight variations obtained in this study were considered fully acceptable for production on a lab scale.

Homogeneity data (mg naloxone/mg film) showed very good consistency both within batches but also between tested batches.

Films with target dose strength within ±10% were obtained by using the developed batch formulas and batch protocols.

Both high and low pH film formulations containing EDTA can be prepared fulfilling the set criteria.

A low pH film formulation using a similar formulation as Narcan® nasal spray can be prepared fulfilling the set criteria.

Inclusion of the transcellular permeability enhancer oleic acid in the formulation is possible.

Example 2: In Vitro Permeation of Naloxone from Different Alginate Film Formulations Through Buccal Tissue Constructs The ability of prototype naloxone film formulations to deliver naloxone over the buccal mucosa was investigated using a robust and reproducible cell-based in vitro model. EpiOral™ (MatTek, Inc.) is a model consisting of a tissue construct equivalent to c. nine cell layers of cells based on non-cornified human oral keratinocytes [12]. EpiOral™ tissues have been used as a model to study oral pathologic states, to assess oromucosal irritation and to assess buccal drug absorption. The model has also been used to study the impact of permeation enhancing excipients on drug uptake [13]. The tissue constructs are grown in inserts suitable for use in 6 and 24 well cell culture plates and the larger version can be removed from the insert and mounted in Franz cell permeation apparatuses.

The factors potentially affecting the absorption of naloxone from the studied alginate films include pH (and charge) and permeation enhancing excipients (e.g., EDTA and oleic acid). Naloxone is a base with a $pK_a$ of 7.84 and will therefore be slightly charged at neutral pH and increasingly charged in more acidic solutions [9]. 50% of naloxone is by definition positively charged at its $pK_a$, i.e. at pH 7.84. 90% is charged at pH 6.84 and 99% would be charged at pH 5.84 or lower. While this may be advantageous during film production, a charged naloxone species is likely less efficiently absorbed over the mucosa than the uncharged naloxone free base.

EDTA can potentially increase paracellular absorption by reducing extra and intracellular $Ca^{2+}$ levels which affects the $Ca^{2+}$ dependent proteins in the tight junction complexes. Further the excipient can interact with phospholipids in the cell membrane and increase its fluidity leading to increased transcellular absorption. Oleic acid can also effect on drug permeability over bilayers. An interaction between fatty acids and polar head groups of phospholipids has been demonstrated that increases membrane flexibility and may promote transcellular drug uptake.

EpiOral™ tissues were delivered on day 0 and stored in a refrigerator overnight. Before the experiment, the inserts were inspected and cleaned from any agarose gel residues from the transportation and rinsed using EpiOral™ assay medium. All media used in the experiment (EpiOral™ Assay and Dulbecco's phosphate-buffered saline (DPBS)) were preheated to 37° C. before contact with the tissues.

In total, 6 different naloxone film formulations (Table 8) were tested in triplicate together with control solutions. The buccal films were in this study pre-dissolved in 1 mL DPBS having pH 6.5 or pH 8.0 reflecting the composition (low or high pH) of the formulations. This was done to facilitate application of the dose to the tissues. The control solution was prepared by diluting a DMSO stock in DPBS buffer at pH 7.4 to a final concentration of 600 µM.

TABLE 8

Naloxone film formulations used in the in vitro permeation study.

| Film | Formulation composition | Batch # |
|---|---|---|
| Naloxone formulation A | 10 mg, low pH | 10 |
| Naloxone formulation B | 10 mg, low pH + EDTA | 14 |
| Naloxone formulation C | 10 mg, low pH + EDTA + Oleic acid | 23 |
| Naloxone formulation D | 10 mg, low pH + EDTA + Oleic acid (SNEDDS) | 20 |
| Naloxone formulation E | 10 mg, high pH | 26 |
| Naloxone formulation F | 10 mg, high pH + EDTA | 16 |

Permeation Experiment:

At the beginning (t=0 min) of the experiment, 300 µL of the dissolved films and control solution were placed on the tissues in the donor compartments. At t=5, 15, 30, 60, 90, 120 and 150 min the 300 µL DPBS pH 7.4 receiver solution was removed and replaced with new DPBS. At t=150 min the donor solution was removed and sampled. All samples were pipetted into HPLC vials with glass inserts and stored at −20° C. until analysis. The remainder of the donor solutions were also stored in freezer for analysis. All samples were quantified using LCMS-MS.

Tissue Integrity Assay:

After the 150 minute samples were taken, the tissues were rinsed twice using DPBS and a 100 µM Luciferin yellow solution was added to the donor compartments. After 1 hour the receiver solution was transferred to wells in a 96-well plate for analysis using a plate reader.

Figure 12:
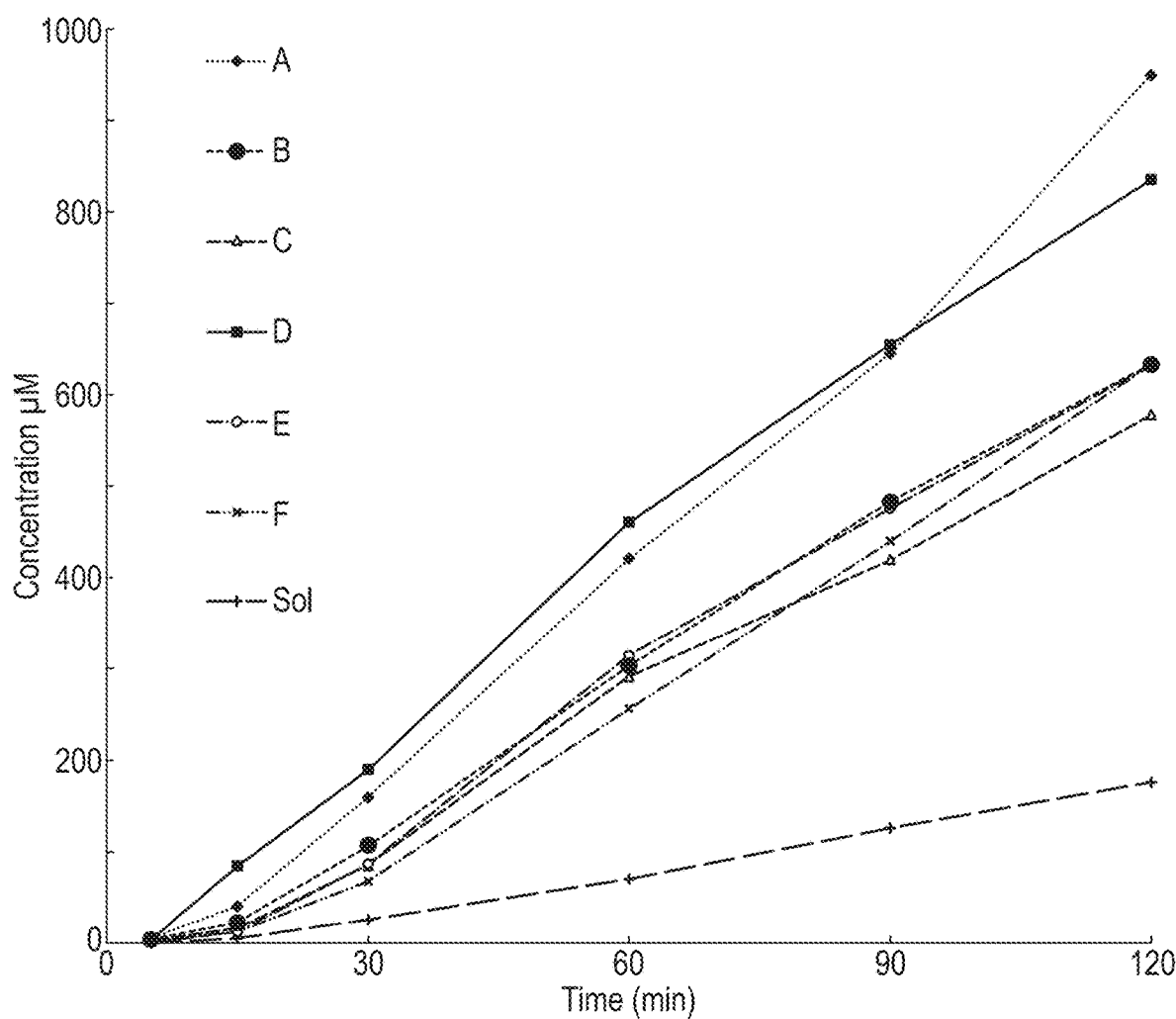
FIG. 12: Cumulative concentration of (−)-naloxone in the basolateral compartment during the permeation experiment. The formulations A-F are as described in Table 8.

Results:

All formulations successfully delivered the naloxone to the tissues and the drug was absorbed in measurable amounts at all measured time-points. The control solution had relatively lower concentration compared to the film formulations resulting in a lower flux (FIG. 12). The effective permeation coefficient (Kp) of the formulation was calculated using Fick's law according to equation 1:

$$Kp = \frac{\text{Average steady state flux}}{C_D - C_R}$$

where average steady state flux was determined to be achieved after 90-120 minutes, $C_D$ is the concentration in the donor (or apical) compartment, and $C_R$ is the concentration in the receiver (or basolateral) compartment. Kp values for each formulation, and the control solution, are shown in FIG. 13.

The integrity assay showed no negative effects of the formulations or the control solution on the tissues.

Example 3: Single-Dose Pharmacokinetics of (−)-Naloxone in Beagle Dogs Following Buccal and Intravenous Administration Four film formulations of naloxone were tested in beagle dogs to compare the buccal film exposures to a single acute intravenous dose of naloxone hydrochloride. The absolute bioavailability of the various buccal film formulations could be measured by comparison with the intravenous dosing experiments.

Among the available preclinical species, dogs and pigs are thought to be the most appropriate for buccal formulation screening, although rabbit has also been used [14]. Although it has been shown that dogs and pigs have a somewhat thicker buccal mucosa than humans, these studies have been designed to give a rank-ordering of formulation performance.

The study employed a randomized cross-over design in which three dogs were administered four different buccal film formulations of (−)-naloxone and a single intravenous dose of naloxone HCl (0.143 mg/kg for a total average dose of approximately 1.95 mg/dog), once a week for five successive weeks.

The three beagle dogs used in the experiment were male, non-naïve beagle dogs, weighing 12.7-13.9 kg, 37-39.5 months old, from CEDS (France) at the first session.

Formulations:

The four (−)-naloxone formulations tested in the present study correspond to those showing the best properties after preliminary formulation tests were conducted. The formulations are those referred to as Batch numbers 10, 16, 20 and 26 in the preceding Examples 1 and 2, and were prepared as described above in Example 1. A summary of the properties of each of these formulations, herein referred to as Formulations 1-4, are provided in Table 9.

TABLE 9

Formulations used in the present study to screen the exposure of Beagle dogs to (−)-naloxone.

| Formulation designation | Batch # | Characteristics of film formulation | Dose |
|---|---|---|---|
| Formulation 1 | Batch 10 | Low pH | 10 mg |
| Formulation 2 | Batch 16 | High pH + EDTA | 10 mg |
| Formulation 3 | Batch 20 | Low pH + EDTA + Oleic Acid | 10 mg |
| Formulation 4 | Batch 26 | High pH | 10 mg |
| Intravenous | — | Naloxone HCl in physiological saline | 0.143 mg/kg |

Treatment Schedule:

Naloxone was evaluated at one dose level via oral buccal film formulations (10 mg/dog) with a crossover design and one dose level by intravenous (I.V.) injection (0.143 mg/kg). The experiment included one group of three dogs, each receiving five administrations with a one-week washout period between each administration, as shown in Table 10.

TABLE 10

Administration schedule of beagle dogs used in the experiment.

| Animal | Test session 1 | Test session 2 | Test session 3 | Test session 4 | Test session 5 |
|---|---|---|---|---|---|
| C10BJ5 | Formulation 1 (1 film/dog) | Formulation 4 (1 film/dog) | Formulation 3 (1 film/dog) | Formulation 2 (1 film/dog) | Naloxone I.V. (0.143 mg/kg) |

TABLE 10-continued

Administration schedule of beagle dogs used in the experiment.

| Animal | Test session 1 | Test session 2 | Test session 3 | Test session 4 | Test session 5 |
|---|---|---|---|---|---|
| C8BK39 | Formulation 2 (1 film/dog) | Formulation 1 (1 film/dog) | Formulation 4 (1 film/dog) | Formulation 3 (1 film/dog) | Naloxone I.V. (0.143 mg/kg) |
| C3BM23 | Formulation 3 (1 film/dog) | Formulation 2 (1 film/dog) | Formulation 1 (1 film/dog) | Formulation 4 (1 film/dog) | Naloxone I.V. (0.143 mg/kg) |

I.V. = intravenous.

Animals were housed individually during each test (PK) session.

Preliminary Training:

Before the first PK session, each dog was familiarized to the oral buccal film application on four occasions. A film containing placebo was applied at the proposed mucosal place, i.e. on the mucosa of upper lip above the upper gingiva at the nearest point to the nose, maintaining the dog mouth closed.

Food Regimen:

On each testing day, the dogs received their daily individual food ration one hour before administration. They were abstained from food and water during one hour after the administration. Apart from that, the animals had free access to water.

Dosing:

In the test sessions 1-4, one oral buccal film was applied to internal buccal mucosa of each dog at the nearest point to the nose, i.e. on the upper lip above the upper gingiva above the canine. The mouth was maintained closed for 5 minutes. In the test session 5, the naloxone solution was intravenously injected into the cephalic vein as a slow bolus (2 mL/kg).

The buccal mucosa was inspected 5 minutes (i.e. at the end of the application) and 1 hour following initial administration of the buccal film, in order to observe any possible local irritation.

Blood Sampling and Sample Shipment:

At each test session, serial blood samples were collected in all dogs at 12 time points: pre-dose, and then 0.083 (5 min), 0.167 (10 min), 0.33 (20 min), 0.5 (30 min), 1, 2, 3, 4, 5, 6 and 8 hours after the initial application, giving therefore a total of 180 blood samples. At each time-point, a blood sample of 2 mL was collected by puncture in a jugual vein in conscious animals using an identified vacuum tube containing K2-EDTA (Greiner Bio-One ref #454047) for plasma preparation. Immediately after collection, the blood sample was gently agitated and stored on ice until centrifugation (within 30 minutes of sampling). The blood samples were centrifuged at 4° C., at 1500 g, for 10 minutes.

The entire resultant plasma was immediately transferred into an identified 1 mL polypropylene screw capped cryotube (1 aliquot of at least 800 µL of plasma) maintained on ice. The tubes were stored upright at approximately −20° C. until shipment to the test site, ABS Laboratories (BioPark, Broadwater Road, Welwyn Garden City, Herts AL7 3AX), for analysis by HPLC-MS (high performance liquid chromatography-mass spectrometry) using a standard separation protocol.

Data Analysis Methods:

Individual concentration (C) versus time (T) curves were analysed for standard pharmacokinetic (PK) parameters using non-compartmental analysis using the SimBiology package of MatLab, Version 2015b. Summary statistics for the total area under the curve for the 0-8 hour time period ($AUC_{0-8hr}$), time to maximum plasma concentration ($T_{max}$), maximum plasma concentration ($C_{max}$) and Bioavailability (F) are given in Table 11. In addition, the mean plasma levels after 5 minutes are given in Table 11 to give a direct comparison of uptake characteristics between the various formulations.

TABLE 11

Summary of mean pharmacokinetic parameters from the four (-)-naloxone buccal film formulations and intravenous naloxone in beagle dogs (n = 3).

| Formulation | Dose | $AUC_{0-8\,hr}$ ng/ml * min | $C_{max}$ ng/ml | $T_{max}$ min | F % | Plasma Conc. at 5 min. |
|---|---|---|---|---|---|---|
| Formulation 1 | 10 mg | 5118.3 | 146.6 | 20 | 80 | 45.5 |
| Formulation 2 | 10 mg | 1304.4 | 39.2 | 11.7 | 20 | 26.0 |
| Formulation 3 | 10 mg | 3844.1 | 113.5 | 15 | 60 | 69.0 |
| Formulation 4 | 10 mg | 1413.9 | 35.5 | 16.7 | 22 | 9.61 |
| Intravenous | 0.143 mg/kg | 1249.7 | 29.4 | 6.7 | — | 28.2 |

Study Results:

Individual time versus plasma naloxone concentration curves are given in FIGS. 1A-1C. Rapid absorption of naloxone is observed with all formulations with individual $T_{max}$ values varying from 5 minutes to 30 minutes. Lower absorption is observed with the high pH formulations (Formulations 2 and 4) compared with the low pH formulations (Formulations 1 and 3).

The differences in the exposure levels of the four different formulations can be more clearly seen by assessing the mean plasma values of the three individual dogs after administration of the various formulations. These results are given in FIG. 15.

Results of the non-compartmental analysis of the present formulation screening study are given in Table 2. The results suggest differences in the extent of absorption between the low and high pH formulations. As seen from the $T_{max}$ values, absorption across the buccal mucosa appears to be rapid with individual dog $C_{max}$ values occurring between 10 and 20 minutes, but more significantly, the 5 minute plasma concentrations in all dogs appeared to be significantly higher than that necessary for a pharmacological effect.

Closer scrutiny of the plasma concentration versus time curve for all doses in the time period 0 to 60 minutes is given in FIG. 16. From these mean curves, it is apparent that the majority of the dose that would be absorbed is absorbed within the first 20 minutes, perhaps with the exception of Formulation 3 which appears to undergo a rise in plasma naloxone concentration at 30 minutes.

Further supporting the conclusion that the majority of the dose is absorbed within the first 30 minutes is the observation that the slope of all the plasma concentration versus time curves in the time period between 60 minutes and 240 minutes after administration are comparable (see FIG. 15), indicating similar levels of clearance between the buccal formulations after the initial absorption phase and, most importantly, similar clearance rates to the intravenous dose.

The following conclusions can therefore be drawn from this study:

Mechanistic conclusions appear to be possible using the dog as a formulation screening model.

In the present study, it appears that low pH formulations displayed a greater uptake than high pH formulations, as determined by the absolute bioavailability, although all films resulted in a plasma concentration of (−)-naloxone in the dogs 5 minutes after administration greater than the amount required for a pharmacological effect.

The films containing EDTA or EDTA and oleic acid delivered similar plasma concentrations of (−)-naloxone within a set time period to films lacking these components.

Rapid absorption is observed with all formulations and it appears that absorption of the 'absorbable fraction' is complete within the first 20 to 30 minutes after application of the buccal film to the dog buccal mucosal surface.

Example 4: Preparation and Evaluation of Low pH Naloxone-Containing Films Comprising an Antioxidant and a Chelating Agent Modified variants of the "low pH" film formulations were produced, in which the pH of the film formulation prior to coating and drying was reduced to less than 4.2, the API was (−)-naloxone hydrochloride dihydrate, 0.3% by weight of EDTA was present as a chelating agent and 0.1% by weight of sodium bisulfite was present as an antioxidant. Batch formulae for these particular film formulations are provided in Table 12 below.

TABLE 12

Batch formulae for production of low pH naloxone films containing EDTA and sodium bisulfite, and having different pH prior to drying and coating.

| Component | Batch formulae for each low pH naloxone buccal film formulation comprising an antioxidant and a chelating agent | | | Function |
|---|---|---|---|---|
| Target pH | 3.8 | 4.0 | 4.2 | Function |
| Naloxone hydrochloride dihydrate (g) | c. 3.5 | c. 3.5 | c. 3.5 | API |
| Water (mL) | 40-50 | 40-50 | 40-50 | Solvent |
| Sorbitol (g) | 5.25 | 5.25 | 5.25 | Plasticizer |
| Glycerol (g) | 4.5 | 4.5 | 4.5 | Plasticizer |
| Xylitol (g) | 7.5 | 7.5 | 7.5 | Plasticizer |
| Titanium dioxide (g) | 0.11 | 0.11 | 0.11 | Colourant |
| Sodium bisulfite (g) | 0.15 | 0.15 | 0.15 | Antioxidant |
| EDTA solution (mL) (c. 62 mg EDTA/mL) | 7.2 | 7.2 | 7.2 | Chelating agent |
| Sodium alginate (g) (Protonal ® LFR 5/60) | 20 | 20 | 20 | Film-forming polymer |
| 50 mM HCl solution (mL) | — | — | 150 | pH adjustment |
| 75 mM HCl solution (mL) | — | 150 | — | pH adjustment |
| 100 mM HCl solution (mL) | 150 | — | — | pH adjustment | c. = approximately.

The films were produced according to the following procedure:

The glycerol, sorbitol, xylitol, titanium dioxide and sodium bisulfite are added to the hydrochloric acid solution and dissolved under mixing at a temperature from 20 to 40° C.

Separately, the naloxone hydrochloride dihydrate is added to the water and dissolved under mixing at a temperature from 20 to 40° C.

The sodium alginate was added to the acidic solution containing the plasticizers, colourant and antioxidant under mixing (in a food processor) for about 10 minutes.

The naloxone-containing aqueous solution was added to the alginate-containing cast under mixing for about 10 minutes or until a lump free dispersion was achieved, resulting in a viscous cast.

The EDTA solution was added to the alginate-containing cast under mixing for about 10 minutes.

The cast was left overnight in the dark for de-aeration.

The cast was poured onto a glass plate and spread out to a thickness of 1 mm by means of an applicator.

The cast layer was dried in a drying cabinet heated to approximately 60° C. for approximately 2 hours until a residual water content of from 9 to 11% by weight was achieved and a solid film was formed.

The solid film was cut into pieces measuring 15×20 mm with a knife.

The films were stored in PET-lined aluminium pouches for eight weeks under three different sets of conditions: one set of films was stored at 25° C. and 60% relative humidity; another was stored at 40° C. and 75% relative humidity; and a third was stored at 50° C. and 75% relative humidity. The amount of total impurities in the films were measured after 0, 2, 4 and 8 weeks of storage and the results are displayed in FIGS. 17-19 (no testing was carried out at the two-week time point for the films stored at 25° C. and 60% relative humidity).

The data clearly show that a low total amount of impurities (<1% by weight) are present in the films after eight weeks of storage, even at 50° C. and 75% relative humidity. Further, it can be seen from these data that reducing the pH of the film formulation prior to coating and drying from 4.2 to 3.8 causes a reduction in the amount of total impurities observed. Thus, it is a surprising finding of the present invention that the formation of impurities in the films can be suppressed in film formulations having a pH of 4.2 or lower prior to coating and drying, and which comprise both an antioxidant and a chelating agent. Without wishing to be bound by any particular theory, it is believed that the amount of the dimer of naloxone having formula (IV) is particularly reduced in these film formulations.

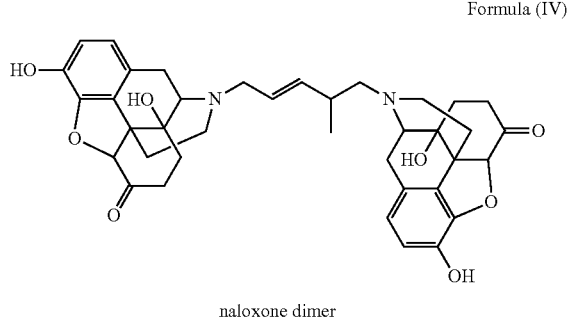 [SMILES: CC(/C=C/CN1CCC23c4c5ccc(O)c4OC2C(=O)CCC3(O)C1C5)CN1CCC23c4c5ccc(O)c4OC2C(=O)CCC3(O)C1C5]

Formula (IV)

naloxone dimer

REFERENCES

[1] Bourassa, P.; Tudashki, H. B.; Pineyro, G.; Grandbois, M.; Gendron, L. Label-free monitoring of μ-opioid receptor-mediated signalling. *Mol Pharmacol*, 2014, 86(2), 138-149.

[2] https://www.drugs.com/naloxone.html (accessed 20 Apr. 2017)

[3] Dowling, J.; Isbister, G. K.; Kirkpatrick, C. M.; Naidoo, D.; Graudins, A. Population pharmacokinetics of intravenous, intramuscular, and intranasal naloxone in human volunteers. *Ther Drug Monit*, 2008, 30(4), 490-496.

[4] Tylleskar, I.; Skulberg, A. K.; Nilsen, T.; Skarra, S.; Jansook, P.; Dale, O. Pharmacokinetics of a new, nasal formulation of naloxone. *Eur J Clin Pharmacol*, 2017, 73, 555-562.

[5] Prachayasittikul, V.; Isarankura-Na-Ayudhya, C.; Tantimongcolwat, T.; Nantasenamat, C.; Galla, H. J. EDTA-induced Membrane Fluidization and Destabilization: Biophysical Studies on Artificial Lipid Membranes. *Acta biochimica et biophysica Sinica*, 2007, 39(11), 901-913.

[6] Managaro, A.; Wertz, P. The effect of permeabilizer on the in vitro penetration of propranolol through porcine buccal epithelium.

[7] Date, A. A.; Desai, N.; Dixit, R.; Nagarsenker, M. Self-nanoemulsifying Drug Delivery Systems: Formulation Insights, Applications and Advances. *Nanomedicine*, 2010, 5(10), 1595-1616.

[8] Pouton, C. W. Formation of poorly water-soluble drugs for oral administration: Physicochemical and physiological issues and the lipid formulation classification system. *European Journal of Pharmaceutical Sciences*, 2006, 29(3-4), 278-287.

[9] https://pubchem.ncbi.nlm.nih.gov/compound/naloxone (accessed 30 May 2017)

[10] U.S. Pat. No. 9,192,570 B2

[11] Friedl, H. et al. Development and evaluation of a novel mucus diffusion test system approved by self-nanoemulsifying drug delivery system. *Pharmaceutics, drug delivery and pharmaceutical technology*, 2013, 102, 4406-4413.

[12] Bachelor, M.; Breyfogle, B.; Klausner, M.; Corporation, M.; Avenue, H. Organotypic Human oral tissue models for evaluation of oral care products presented at Society of Toxicology 2014 annual meeting. 2014, no. 1, pp. 3-7.

[13] Thakur, R. A.; Michniak, B. B.; Meidan, V. M. Transdermal and buccal delivery of methylxanthines through human tissue in vitro. *Drug Dev. Ind. Pharm.*, 2007, 33(5), 513-521.

[14] Squier, C. A.; Wertz, P. W. Structure and function of the oral mucosa and implications for drug delivery. In: *Oral mucosal drug delivery*. Rathbone M. J., editor. Marcel Dekker, 1996, pp. 1-25.

What is claimed is:

1. A film suitable for administration to an oral cavity comprising:
   (i) an alginate salt of a monovalent cation or a mixture of alginate salts containing at least one alginate salt of a monovalent cation; and
   (ii) an active pharmaceutical ingredient (API) which is naloxone, a 3-O-ester derivative of naloxone, a 3-O-carbamyl derivative of naloxone, or a pharmaceutically acceptable salt thereof;
   wherein the film is configured to achieve a peak plasma concentration of naloxone in a patient greater than 1 ng/mL within 60 minutes from adhesion of the film to the mucosa of the oral cavity.

2. The film according to claim 1, wherein the API is naloxone, the free base form of naloxone or a pharmaceutically acceptable salt thereof.

3. The film according to claim 1, wherein the API is (−)-naloxone or a pharmaceutically acceptable salt thereof.

4. The film according to claim 1, wherein the film comprises an opioid or a pharmaceutically acceptable salt thereof, in addition to the API.

5. The film according to claim 4, wherein the opioid is selected from morphine, dimorphine, fentanyl, tramadol, 2,4-dinitrophenylmorphine, 6-MDDM, chlornaltrexamine, desomorphine, dihydromorphine, hydromorphinol, methyldesorphine, N-phenethylnormorphine, RAM-378, acetylpropionylmorphine, dihydroheroin, dibenzoylmorphine, dipropanoylmorphine, heroin, nicomorphine, codeine, 6-MAC, benzylmorphine, codeine methylbromide, dihydroheterocodeine, ethylmorphine, heterocodeine, pholcodine, myrophine, 14-cinnamoyloxycodeinone, 14-ethoxymetopon, 14-methoxymetopon, PPOM, 7-spiroindanyloxymorphone, acetylmorphone, codeinone, conorphone, codoxime, thebacon, hydrocodone, hydromorphone, metopon, morphinone, N-phenethyl-14-ethoxymetopon, oxycodone, oxymorphone, pentamorphone, semorphone, chloromorphide, 14-hydroxydihydrocodeine, acetyldihydrocodeine, dihydrocodeine, nalbuphine, nicocodeine, nicodicodeine, oxymorphazone, 1-iodomorphine, M6G, 6-MAM, norcodeine, normorphine, morphine-N-oxide, cyclorphan, DXA, levorphanol, levophenacylmorphan, levomethorphan, norlevorphanol, oxilorphan, phenomorphan, furethylnorlevorphanol, xorphanol, butorphanol, cyprodime, drotebanol, 7-PET, acetorphine, BU-48, buprenorphine, cyprenorphine, dihydroetorphine, etorphine, norbuprenorphine, or combinations thereof.

6. The film according to claim 1, wherein the alginate salt of a monovalent cation is selected from a sodium alginate, a potassium alginate or an ammonium alginate.

7. The film according to claim 1, wherein the film comprises from 25% to 99% by weight of the alginate salt of a monovalent cation or the mixture of alginate salts containing at least one alginate salt of a monovalent cation, from 0% to 20% by weight of water, and from 0.001% to 75% by weight of the API, or wherein the film comprises from 29% to 93% by weight of the alginate salt of a monovalent cation or the mixture of alginate salts containing at least one alginate salt of a monovalent cation, from 5% to 15% by weight of water, and from 0.15% to 50% by weight of the API.

8. The film according to claim 1, wherein the film further comprises:
   at least one plasticizer which is selected from sorbitol, glycerol, or a combination thereof; and
   a basifying agent which is aqueous sodium hydroxide, or an acidifying agent which is phosphoric acid.

9. The film according to claim 1, wherein the film further comprises:
   a permeation enhancer selected from EDTA, oleic acid, or combinations thereof;
   optionally, a buffering component which is citric acid or sodium dihydrogen phosphate;
   optionally, a self-nanoemulsifying drug delivery system (SNEDDS); and
   optionally, a chelating agent.

10. The film according to claim 1, wherein the film further comprises:
    at least one plasticizer which is selected from sorbitol, glycerol, xylitol or a combination thereof;
    an antioxidant selected from ascorbic acid, citric acid, sodium bisulfite, sodium metabisulfite, or butyl hydroxitoluene;
    a chelating agent selected from ethylenediaminetetraacetic acid (EDTA), ethylene glycol-bis((β-aminoethyl ether)-N,N,N',N'-tetraacetic acid (EGTA), 1,2-bis (orthoaminophenoxy) ethane-N,N,N',N'-tetraacetic acid (BAPTA), citric acid, phosphonic acid, glutamic acid, histidine, or malate;
    an acidifying agent; and
    optionally, titanium dioxide.

11. The film according to claim 7, wherein the film further comprises from 0% to 40% by weight of sorbitol, and from 0% to 40% by weight of glycerol.

12. A method of treating the effects of acute opioid overdose or reducing the risk of opioid abuse in a human patient, wherein said method comprises administration of at least one film according to claim 1 to said human patient.

13. The method according to claim 12, wherein the film is administered to the oral cavity of the human patient.

14. A method of manufacturing a film according to claim 1, said method comprising:
    (A) either:
        (a) optionally, mixing one or more preservatives in water;
        (b) either: (i) mixing the API and, optionally, at least one buffering component in water, or in the solution obtained in (a), and subsequently adjusting the pH of the resultant solution to the desired level by addition of an appropriate acid or base, typically a diluted aqueous acid or alkali; or
            (ii) adjusting the pH of water, or the solution obtained in (a), to the desired level by addition of an appropriate acid or base, typically a diluted aqueous acid or alkali, and subsequently mixing the API and, optionally, at least one buffering component in the pH-adjusted solution;
        (c) optionally, adding further water and/or one or more plasticizers under further mixing; and
        (d) adding the alginate salt of monovalent cation under suitable conditions to result in the formation of a viscous cast;
        or alternatively:
        (i) mixing one or more excipients and one or more preservatives in an acidic aqueous solution;
        (ii) separately, dissolving the API in water;
        (iii) mixing the solution obtained in (i) with the alginate salt of monovalent cation;
        (iv) adding the solution obtained in (ii) to the solution obtained in (iii) under suitable conditions to result in the formation of a viscous cast; and
        (v) optionally, adding a chelating agent to the cast;
    (B) optionally, leaving the cast to de-aerate;
    (C) pouring the cast onto a surface and spreading the cast out to the desired thickness;
    (D) drying the cast layer, typically at a temperature of from 40 to 70° C. until the residual water content of the film is from 5 to 15% by weight and a solid film is formed; and
    (E) optionally, cutting the solid film into pieces of the desired size, further optionally placing these pieces into pouches, sealing the pouches and further optionally, labelling them.

15. The method of claim 14, wherein:
    optional (A)(a) is omitted, and wherein (A)(b) consists of mixing the API and, optionally, at least one buffering component in water, and subsequently adjusting the pH of the solution to the desired level by addition of an appropriate acid or base, typically a diluted aqueous acid or alkali; or
    wherein (A)(a) consists of mixing one or more preservatives in water, and wherein (A)(b) consists of adjusting the pH of the solution to the desired level by addition of an appropriate acid or base, typically a diluted aqueous acid or alkali and subsequently mixing the API and, optionally, at least one buffering component in the pH-adjusted solution; or
    wherein after the viscous cast is poured onto a surface, it is first spread out to a thickness of about 2 mm by means of an applicator with a slit height of about 2 mm, and is then subsequently spread out to a thickness of about 1 mm by means of an applicator with a slit height of about 1 mm.

16. The film according to claim 1, wherein the alginate salt of a monovalent cation comprises from 25 to 35% by weight of β-D-mannuronate and/or from 65 to 75% by weight of α-L-guluronate.

17. The film according to claim 1, wherein the alginate has a mean molecular weight of from 20,000 g/mol to 90,000 g/mol.

18. The method according to claim 12, wherein the human patient possesses an opioid dependency.

19. The film according to claim 3, wherein the API is (−)-naloxone, the free base form of (−)-naloxone, (−)-naloxone hydrochloride, (−)-naloxone hydrochloride dehydrate, or combinations thereof.

20. The film according to claim 6, wherein the alginate salt of a monovalent cation is a sodium alginate.

* * * * *